US007251513B2

(12) United States Patent
Kondoh et al.

(10) Patent No.: US 7,251,513 B2
(45) Date of Patent: Jul. 31, 2007

(54) METHOD OF MEASURING BIOLOGICAL INFORMATION USING LIGHT AND APPARATUS OF MEASURING BIOLOGICAL INFORMATION USING LIGHT

(75) Inventors: Kazuya Kondoh, Osaka (JP); Shinji Uchida, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 404 days.

(21) Appl. No.: 10/473,099

(22) PCT Filed: Jan. 23, 2003

(86) PCT No.: PCT/JP03/00586

§ 371 (c)(1),
(2), (4) Date: Mar. 24, 2004

(87) PCT Pub. No.: WO03/063704

PCT Pub. Date: Aug. 7, 2003

(65) Prior Publication Data

US 2004/0152962 A1      Aug. 5, 2004

(30) Foreign Application Priority Data

Jan. 25, 2002 (JP) ............................. 2002-016548
Apr. 26, 2002 (JP) ............................. 2002-126811
Oct. 29, 2002 (JP) ............................. 2002-314842

(51) Int. Cl.
*A61B 5/00* (2006.01)
(52) U.S. Cl. ..................................... 600/310
(58) Field of Classification Search ................ 600/310, 600/316, 335, 344
See application file for complete search history.

(56) References Cited

U.S. PATENT DOCUMENTS

| 4,927,264 | A | * | 5/1990 | Shiga et al. ................. 600/322 |
| 5,057,695 | A | * | 10/1991 | Hirao et al. ................. 600/310 |
| 6,016,435 | A | | 1/2000 | Maruo et al. |
| 6,026,313 | A | | 2/2000 | Kexin |

(Continued)

FOREIGN PATENT DOCUMENTS

EP        1 013 219 A1     6/2000

(Continued)

OTHER PUBLICATIONS

International Search Report for PCT/JP03/00586 dated Mar. 18, 2003.

(Continued)

*Primary Examiner*—Eric F. Winakur
(74) *Attorney, Agent, or Firm*—RatnerPrestia

(57) ABSTRACT

A compact apparatus of measuring biological information using light capable of measuring biological information with high reproducibility and accuracy is provided. The apparatus of measuring biological information using light comprises a light source part irradiating an organism, a light receiving part receiving light propagating from the light source part through the inside of the organism and outgoing from the surface of the organism, a forming part forming the surface of the organism into a predetermined shape by applying a pressure thereto, and a calculation part calculating information of the relation between the amount of received light and the biological information of the organism previously determined based on the amount of light received in the light receiving part.

19 Claims, 33 Drawing Sheets

U.S. PATENT DOCUMENTS 6,078,828 A * 6/2000 Yasuda et al. .............. 600/310
6,449,500 B1 9/2002 Asai et al.
6,618,615 B1 9/2003 Kimura et al.

FOREIGN PATENT DOCUMENTS

| JP | 11-070101 | 3/1999 |
| JP | 11-123196 | 5/1999 |
| JP | 2000-155091 | 6/2000 |
| JP | 2000-237195 A | 9/2000 |
| JP | 2001-029333 | 2/2001 |
| JP | 2001-037741 | 2/2001 |
| JP | 2001-95806 A | 4/2001 |

OTHER PUBLICATIONS

Form PCT/ISA/210 English Translation of ISR for PCT/JP03/00586 dated Mar. 18, 2003.

* cited by examiner

AMOUNT OF RECEIVED LIGHT FOR MEASUREMENT (W)

Fig. 26 (a)
Fig. 26 (b)
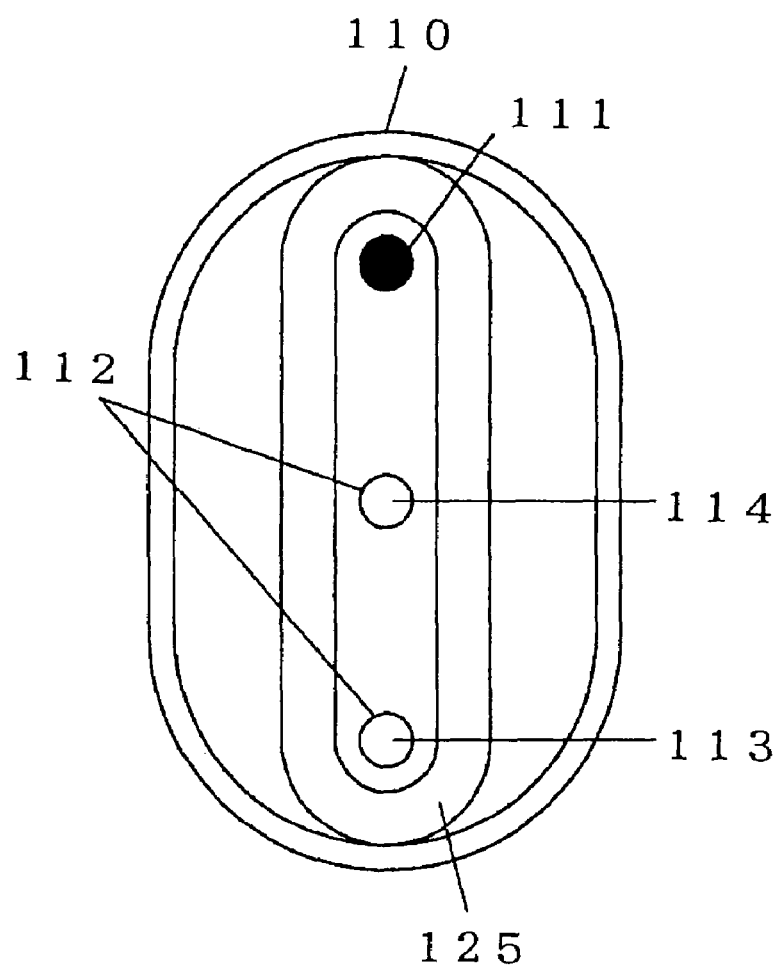
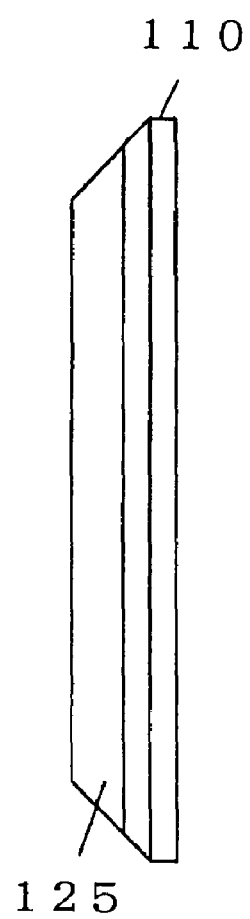

METHOD OF MEASURING BIOLOGICAL INFORMATION USING LIGHT AND APPARATUS OF MEASURING BIOLOGICAL INFORMATION USING LIGHT

This application is a U.S. national phase application of PCT International Application PCT/JP03/00586.

TECHNICAL FIELD

The present invention relates to a method and apparatus of measuring biological information using light capable of optically measuring biological information including the thickness of subcutaneous fat, the percent of body fat, the concentration of glucose in an organism and concentration of oxygen in an organism.

BACKGROUND ART

A method has been known in which light enters an organism from a light source placed on the surface of the organism. The light appears again on the surface of the organism after propagating through the inside of the organism while being scattered and absorbed. The light received on the surface is used to measure the concentration of an absorbing material in the organism or the thickness of a tissue. FIG. 38 shows a positional relation between a light source and a light receiving element and an organism in a subcutaneous fat thickness measuring apparatus described in Japanese Patent Laid-Open No. 2000-155091 as one example of the method. The disclosure of Japanese Patent Laid-Open No. 2000-155091 is incorporated herein by reference in its entirety. A light source 302 and a measuring light receiving element 303 are placed on the surface of an organism 301. Given that the organism has a structure of a parallel flat plate having three layers of a skin 305, a subcutaneous fat 306 and a muscle 307 as shown in FIG. 38, light 308 received by the measuring light receiving element 303 has a correlation with the thickness of the subcutaneous fat 306 due to a difference in absorption and scattering characteristics between organic tissues. However, the amount of light 308 received by the measuring light receiving element 303 varies under significant influences of changes in blood flows of the skin 305 and the subcutis. Therefore, a correcting light receiving element 304 is placed near the light source 302 (1 to 6 mm from the light source 302), and light 308 received by the measuring light receiving element 303 is corrected by the amount of light 309 received by the correcting light receiving element 304, thereby making it possible to measure the thickness of subcutaneous fat with high accuracy.

However, because the organic tissue is not strictly a parallel flat plate as shown in FIG. 39, and arms and legs have cylindrical shapes as shown in FIG. 40, the measurement accuracy is compromised by a local change in thickness.

Also, because the organic tissue is soft and hence highly deformable, the shape of the surface of the organism 301 varies for each measurement even in the same person and the same site, and therefore the amount of received light is varied to compromise reproducibility.

Also, in the case where the subcutaneous fat 306 is thick, the distance between the light source 302 and the measuring light receiving element 303 should be increased for receiving light propagated through a deeper part in the organism by the measuring light receiving element 303. Therefore, there is a disadvantage that the measuring apparatus is scaled up.

Also, in the case where the subcutaneous fat 306 is thick, the distance between the light source 302 and the measuring light receiving element 303 is increased, and therefore the amount of light received in the measuring light receiving element 303 is reduced to compromise the measurement accuracy.

Also, in the case where the subcutaneous fat 306 is thick, the light reception sensitivity in the measuring light receiving element 303 should be improved, and therefore the accuracy and sensitivity of the measuring light receiving element 303 should be enhanced, thus raising a disadvantage that expensive parts are required.

Also, in the case where the subcutaneous fat 306 is thick, light incident from sources other than the light source 302 such as sunlight into the organism is measured even if the sensitivity of the measuring light receiving element 303 is improved, and therefore the surface of the organism 301 should be shielded sufficiently.

Also, in the conventional subcutaneous fat thickness measuring apparatus, the thickness of the subcutaneous fat 306 is changed in association with the variation in contact pressure applied to the organism by the light source 302 and the measuring light receiving element 303 on the surface of the organism, and therefore the thickness of the subcutaneous fat 306 varies for each measurement to compromise measurement reproducibility. This problem is significant particularly when the subcutaneous fat is thick.

In addition, the subcutaneous fat 306 is deformed due to the contact pressure, and therefore the amount of blood in the subcutaneous fat 306 is changed to cause a variation in absorption characteristics by the blood in the subcutaneous fat 306. Consequently, the amount of light received in the measuring light receiving element 303 fluctuates to compromise measurement reproducibility.

DISCLOSURE OF THE INVENTION

In consideration of the problems described above, the present invention provides, as its object, a compact method of measuring biological information using light and apparatus of measuring biological information using light capable of measuring biological information such as the thickness of subcutaneous fat and the percent of body fat with high reproducibility and accuracy.

Also, in consideration of the problems described above, the present invention provides, as its object, a method of measuring biological information using light and an apparatus of measuring biological information using light capable of measuring the thickness of subcutaneous fat with high reproducibility and accuracy.

To solve the above problems, a first aspect of the present invention is a method of measuring biological information comprising:

a first step of forming the surface of an organism into a predetermined shape by applying a pressure thereto;

a second step of irradiating said organism with light;

a third step of receiving said light propagating through the inside of said organism and outgoing from the surface of said organism; and a fourth step of calculating biological information of said organism using information of the relation between the amount of said received light and the biological information of said organism previously determined based on the amount of said light received in said third step.

A second aspect of the present invention is the method of measuring biological information according to the first aspect of the present invention, wherein in said fourth step, the biological information of said organism is calculated using information of the relation between the amount of said received light and the biological information of said organism after said pressure reaches a level equal to or greater than predefined value, previously determined based on the amount of said received light after said pressure reaches a level equal to or greater than a predefined value.

A third aspect of the present invention is the method of measuring biological information according to the first aspect of the present invention, comprising a fifth step of measuring said pressure,
wherein in said fourth step, the biological information of said organism is calculated using information of the relation between the amount of said received light and said pressure and the biological information of said organism previously determined based on the amount of said light received in said third step and said pressure measured in said fifth step.

A fourth aspect of the present invention is the method of measuring biological information according to the second aspect of the present invention, wherein the predefined value of said pressure is about 7 kPa or greater.

A fifth aspect of the present invention is the method of measuring biological information according to the first aspect of the present invention, wherein the central wavelength of said light applied in said second step is a wavelength of about 500 nm to 1000 nm.

A sixth aspect of the present invention is the method of measuring biological information according to the first aspect of the present invention, wherein in said fourth step, the biological information of said organism is calculated at a time when a predetermined amount of time passes after said pressure reaches a predetermined pressure.

A seventh aspect of the present invention is the method of measuring biological information according to the sixth aspect of the present invention, comprising a sixth step of detecting that said pressure reaches said predefined value,
wherein in said fourth step, the biological information of said organism is calculated based on the amount of said light received in said third step at a time when a predetermined amount of time passes after it is detected that said pressure reaches said predefined value in said sixth step.

An eighth aspect of the present invention is the method of measuring biological information according to the seventh aspect of the present invention, wherein said predetermined amount of time is about 200 ms or greater.

A ninth aspect of the present invention is the method of measuring biological information according to the first aspect of the present invention, wherein in said fourth step, the biological information of said organism is calculated after the amount of said received light is stabilized.

A tenth aspect of the present invention is the method of measuring biological information according to the ninth aspect of the present invention, comprising a sixth step of detecting that said pressure reaches said predefined value,
wherein in said fourth step, variations in the amount of said light received in said third step are monitored when it is detected that said pressure reaches said predefined value in said sixth step, and the biological information of said organism is calculated based on the amount of said received light acquired when the variations in said amount of received light are within a predetermined value.

An eleventh aspect of the present invention is the method of measuring biological information according to the tenth aspect of the present invention, wherein the variations in said amount of received light being within a predetermined value means the variations in said amount of received light being within about ±10%.

A twelfth aspect of the present invention is an apparatus of measuring biological information using light comprising:
a light source part irradiating an organism;
a light receiving part receiving light propagating from said light source part through the inside of said organism and outgoing from the surface of said organism;
a forming part forming the surface of said organism into a predetermined shape by applying a pressure thereto; and
a calculation part calculating biological information of said organism using information of the relation between the amount of said received light and the biological information of said organism previously determined based on the amount of said light received in said light receiving part.

A thirteenth aspect of the present invention is the apparatus of measuring biological information using light according to the twelfth aspect of the present invention, comprising a pressure detecting part detecting that the pressure applied to the surface of said organism by said forming part reaches a level equal to or greater than a predefined value,
wherein said calculation part calculates the biological information of said organism based on the amount of said received light when it is detected that said pressure reaches a level equal to or greater than said predefined value.

A fourteenth aspect of the present invention is the apparatus of measuring biological information using light according to the twelfth aspect of the present invention, comprising a pressure measuring part measuring the pressure applied to the surface of said organism by said forming part,
wherein the biological information of said organism is calculated based on the amount of said light received in said receiving part and said pressure measured in said pressure measuring part.

A fifteenth aspect of the present invention is the apparatus of measuring biological information using light according to the twelfth aspect of the present invention, wherein the face of the forming part contacting the surface of the organism is substantially flat.

A sixteenth aspect of the present invention is the apparatus of measuring biological information using light according to the twelfth aspect of the present invention, wherein a protrusion part is provided on the face of the forming part contacting the surface of the organism, and
the light source part and the light receiving part are provided on said protrusion part.

A seventeenth aspect of the present invention is the apparatus of measuring biological information using light according to the twelfth aspect of the present invention, wherein said light source part has a plurality of light sources.

An eighteenth aspect of the present invention is the apparatus of measuring biological information using light according to the seventeenth aspect of the present invention, wherein said light source part has said light source provided so that the distance between said light source and said light receiving part is a first distance of about 15 mm to 30 mm, and said light source provided so that the distance between said light source and said light receiving part is a second-distance of about 35 mm to 80 mm, and
if the amount of light received in said light receiving part from said light source with said first distance equals Y1, and the amount of light received in a light receiving element from said light source with said second distance equals Y2, said calculation part calculates the biological information of said organism using the ratio between said Y2 and said Y1.

A nineteenth aspect of the present invention is the apparatus of measuring biological information using light according to the twelfth aspect of the present invention, wherein said light receiving part has a plurality of light receiving elements.

A twentieth aspect of the present invention is the apparatus of measuring biological information using light according to the nineteenth aspect of the present invention, wherein said light receiving part has said light receiving element provided so that the distance between said light source part and said light receiving element is a first distance of 15 mm to 30 mm, and said light receiving element provided so that the distance between said light source part and said light receiving element is a second distance of 35 mm to 80 mm, and if the amount of light received in said light receiving element with said first distance equals Y1, and the amount of light received in said light receiving element with said second distance equals Y2, said calculation part calculates the biological information of said organism using the ratio between said Y2 and said Y1.

A twenty-first aspect of the present invention is the apparatus of measuring biological information using light according to the twelfth aspect of the present invention, comprising:

a display part displaying said biological information of said organism calculated in said calculation part;

a communication part communicating said biological information of said organism to and from external apparatuses; and an input part for inputting measurement conditions of said organism.

BRIEF DESCRIPTION OF THE DRAWINGS

FIG. 26(a) is a top view of the forming part of the apparatus of measuring the thickness of subcutaneous fat using light in which the forming part is different in shape from a protrusion part in Embodiment 9 of the present invention, seen from the side on which it contacts the surface of the organism;

FIG. 26(b) is a side view of the forming part of the apparatus of measuring the thickness of subcutaneous fat using light in which the forming part is different in shape from the protrusion part in Embodiment 9 of the present invention, seen from the side on which it contacts the surface of the organism;

Figure 1:
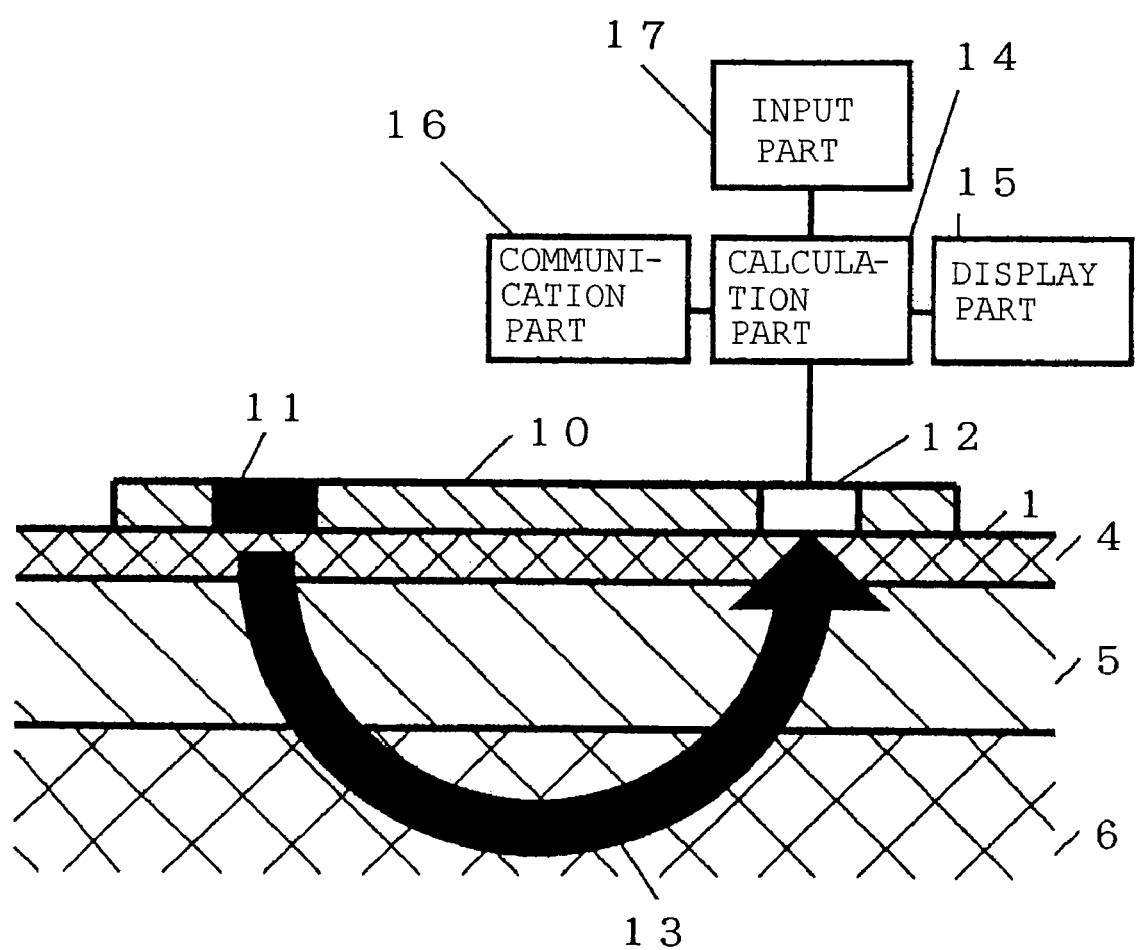
FIG. 1 is a block diagram of an apparatus of measuring biological information using light in Embodiment 1 of the present invention.

DESCRIPTION OF SYMBOLS 1 surface of organism
2 light source
3 measuring light receiving element
4 skin
5 subcutaneous fat
6 muscle
7 light received by measuring light receiving element
8 correcting light receiving element
9 light received by correcting light receiving element
10 forming part
11 light source part
12 light receiving part
13 light received in light receiving part
14 calculation part
15 display part
16 communication part
17 input part
18 protrusion part
19 first light source part
20 second light source part
21 first light receiving part
22 second light receiving part
23 third light receiving part
24, 26 light received in third light receiving part
25 light received in first light receiving part
27 light received in second light receiving part
101 surface of organism
102 light source
103 measuring light receiving element
104 correcting light receiving element
105 skin
106 subcutaneous fat
107 muscle
108 light received by measuring light receiving element
109 light received by correcting light receiving element
110 forming part
111 light source (light source part)
112 light receiving part
113 measuring light receiving element
114 correcting light receiving element
115 pressure measuring unit
116 measuring light source element
117 correcting light source element
118 light received by correcting light receiving element (light from correcting light source element)
119 light received by measuring light receiving element (light from measuring light source element)
120 calculation part
121 display part
122 communication part
123 input part
124 pressure detecting part
125 protrusion part
201 surface of organism
202 light source
203 measuring light receiving element
204 correcting light receiving element
205 skin 206 subcutaneous fat
207 muscle
208 light received by measuring light receiving element
209 light received by correcting light receiving element
210 forming part
211 light source (light source part)
212 light receiving part
213 measuring light receiving element
214 correcting light receiving element
215 pressure detecting part
216 measuring light source element
217 correcting light source element
218 light from correcting light source element
219 light from measuring light source element
220 calculation part
221 display part
222 communication part
223 input part

BEST MODE FOR CARRYING OUT THE INVENTION

Embodiments of the present invention will be described below with reference to the drawings.

The apparatus of measuring biological information using light of the present invention comprises a light source part of irradiating an organism, a light receiving part of receiving light outgoing from the surface of the organism after propagating from the light source part through the inside of the organism, a forming part of forming the surface of the organism into a predetermined shape, and a calculation part of calculating biological information of the organism based on the amount of light received in the light receiving part.

The face of the forming part contacting the surface of the organism is preferably flat.

Also, the degree of reflection of the face of the forming part contacting the surface of the organism is preferably substantially 0.

Also, a protrusion part is preferably provided on the face of the forming part contacting the surface of the organism.

Here, the protrusion part may be provided between the light source part and the light receiving part. In this case, the protrusion part is preferably located at a distance of about 3 to 30 mm from the light source part.

Also, the light source part or/and light receiving part may be provided in the protrusion part.

Here, the protrusion part has preferably a shape such that the organism is deformed so that an area of the surface of the organism having a longitudinal dimension of about 3 to 10 mm and a lateral dimension of 3 to 50 mm is concaved to the depth of about 2 to 20 mm.

Also, there may be a plurality of light source parts or/and light receiving parts.

Also, the apparatus of measuring biological information using light of the present invention preferably has the light source part comprising a first light source part provided at a first predetermined location of the forming part and a second light source part provided at a second predetermined location of the protrusion part, and the light receiving part comprising a first light receiving part provided at a third predetermined location of the forming part opposite to the first predetermined location with the protrusion part therebetween and a second light receiving part provided at a fourth predetermined location of the protrusion.

In addition, the light receiving part preferably comprises a third light receiving part provided at a fifth predetermined location between the second predetermined location and the fourth predetermined location.

Here, it is preferable that the distance between the first predetermined location and the protrusion part is in the range of from about 1 to 20 mm, and the distance between the protrusion part and the third predetermined location is in the range of from about 1 to 20 mm. Also, it is preferable that the distance between the second predetermined location and the fifth predetermined location is in the range of from 1 to 20 mm, and the distance between the second predetermined location and the fourth predetermined location is in the range of from 20 to 50 mm.

Also, the third light receiving part may be provided at the fifth predetermined location between the first predetermined location and the third predetermined location.

Also, preferably, the apparatus of measuring the thickness of subcutaneous fat using light of the present invention further comprises a display part displaying biological information calculated by the calculation part, a communication part communicating the biological information to and from external apparatuses, and an input part for inputting measurement conditions.

In the present invention, the biological information includes the level of subcutaneous fat, the concentration of glucose in an organism and the concentration of oxygen in an organism. Here, the central wavelength of light emitted from the light source part is preferably in the range of from about 450 nm to 1000 nm if the biological information is the concentration of glucose in the organism, and the central wavelength of light emitted from the light source part is preferably in the range of from about 1000 nm to 2000 nm if the biological information is the concentration of oxygen in the organism.

EMBODIMENT 1

FIG. 1 is a block diagram of an apparatus of measuring biological information using light in Embodiment 1 of the present invention.

The apparatus of measuring biological information using light in this embodiment has a light source part 11 and a light receiving part 12 placed in a forming part 10 forming the surface of an organism 1 into a flat shape. Here, it is preferable that the forming part 10 is a rectangle being 25 mm long and 40 mm wide, and the area of the forming part 10 is about 1000 mm² or greater, for example, although not specifically limited. However, the forming part 10 is not necessarily a rectangle. The material of the forming part 10 may be any material having a degree of strength such that the shape of the forming part 10 is not changed when it is contacted against the surface of the organism 1.

The forming part 10 is made of material such as black ABS in which the degree of reflection of the face contacting the surface of the organism 1 is substantially 0 in the range of wavelengths of light emitted from the light source part 11. "Substantially 0" in this case refers to a degree of reflection of about 2% or smaller. Furthermore, as another method, the forming part 10 may be coated or painted with a material with the degree of reflection of 2% or smaller.

A light source such as an LED light source, laser light source or bulb is incorporated in the light source part 11. The central wavelength of light outputted from the light source part 11 is in the range of from about 500 nm to 1000 nm or from about 1000 nm to 2000 nm. Also, the light source part 11 may have a configuration in which the light source is separated from the surface of the organism 1, and the light is guided from the light source of the surface of the organism 1 by optical fibers or the like.

The light receiving part 12 comprises a light receiving sensor such as a photodiode, avalanche photodiode or CdS cell. Also, light may be guided between the surface of the organism 1 and the light receiving sensor by optical fibers or the like.

The calculation part 14 calculates the thickness of subcutaneous fat according to the amount of light 13 received in the light receiving part 12, and the display part 15 displays biological information determined by the calculation part 14 such as the thickness of subcutaneous fat. Also, the communication part 16 communicates biological information determined by the calculation part 14 such as information of the thickness of subcutaneous fat and control data for start of measurement to and from external apparatuses. Also, by the input part 17, measurement conditions such as the measured site, sex, age, height and weight of a subject may be inputted, and control for start of measurement may be performed.

Operations of the apparatus of measuring biological information using light in this embodiment will now be described.

Figure 2:
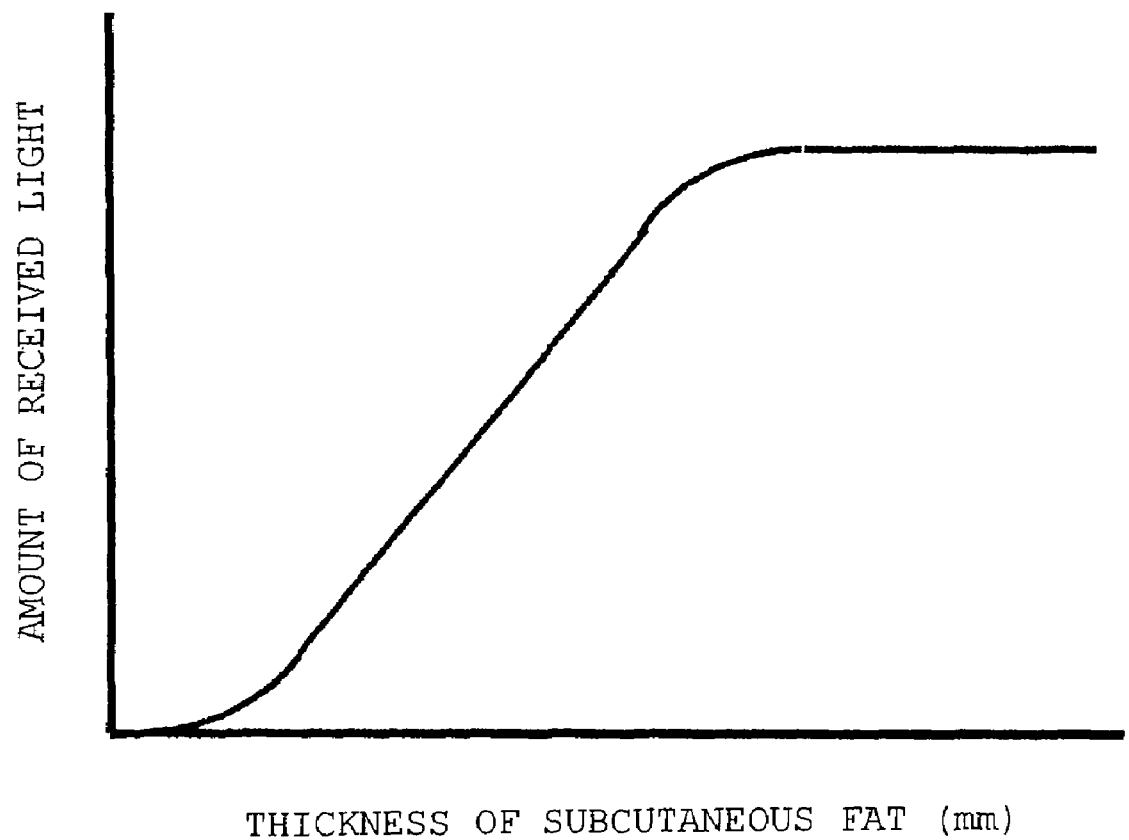
FIG. 2 shows a graph showing a relation between the amount of received light and the thickness of subcutaneous fat in the apparatus of measuring biological information using light of Embodiment 1 of the present invention.

Light emitted from the light source part 11 propagates through a skin 4, a subcutaneous fat 5 and a muscle 6 in the organism while it is scattered and absorbed. Of light propagating through the inside of the organism, the amount of light 13 received in the light receiving part 12 increases with the thickness of the subcutaneous fat 5 due to differences in light absorption and light scattering characteristics between the skin 4 and the subcutaneous fat 5 and the muscle 6. The relation between the thickness of the subcutaneous fat 5 and the amount of received light is shown in FIG. 2. A graph of relation shown in FIG. 2 is previously determined and stored in the calculation part 14, whereby the thickness of subcutaneous fat can be determined in the calculation part 14, using the amount of light 13 received in the light receiving part 12. In the calculation part 14, the percent of body of the subject can be calculated from measurement conditions and the thickness of subcutaneous fat inputted by the input part 17 and the communication part 16. Also, a plurality of measurement conditions may be stored in advance.

Figure 3:
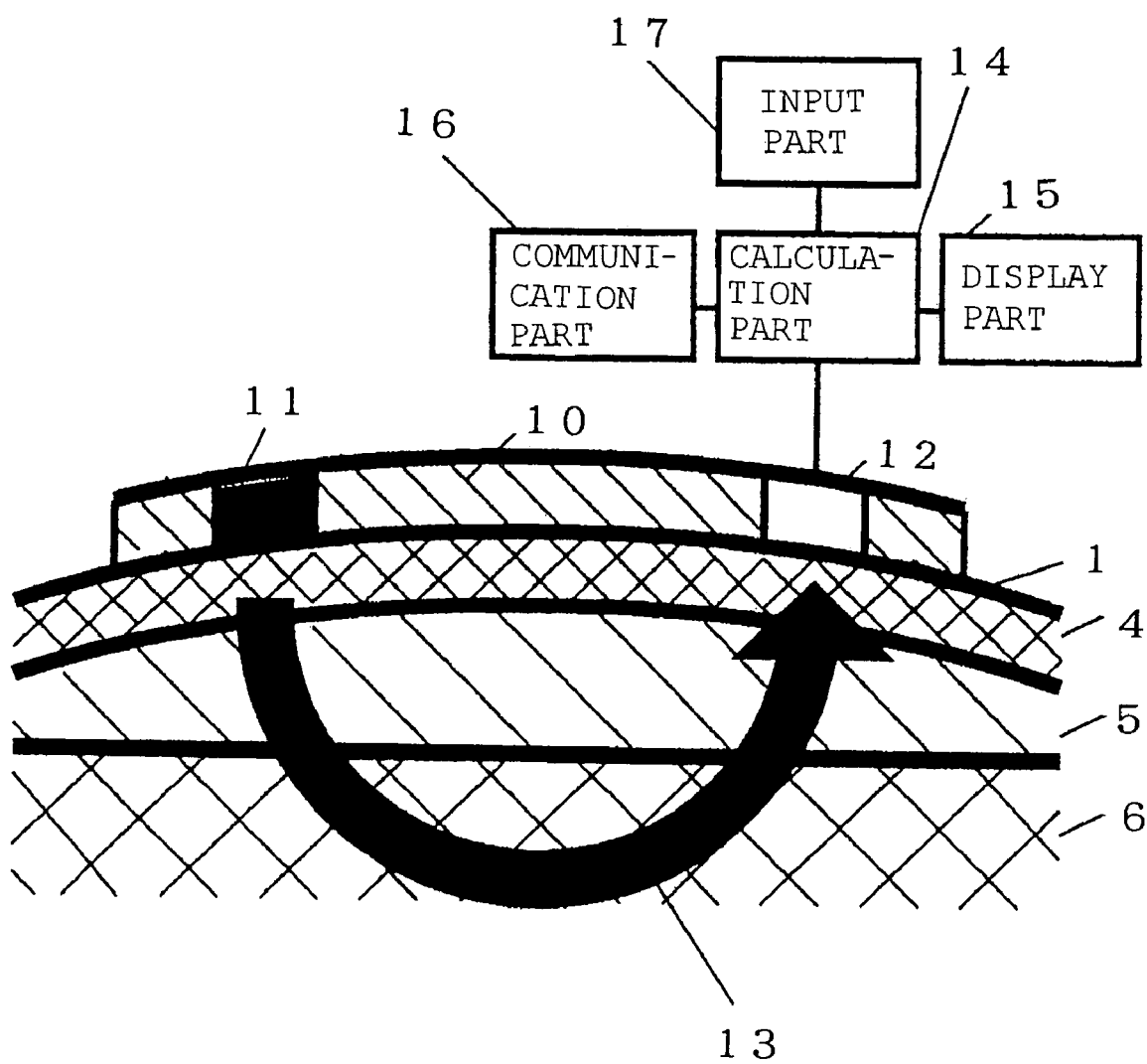
FIG. 3 is a block diagram of the apparatus of measuring biological information using light having a different shape of a forming part in Embodiment 1 of the present invention.

In this operation, the surface of the organism 1 is formed into a flat shape by the forming part 10, whereby a change in propagation of light in association with a local change in shape of the surface of the organism 1 can be controlled. Also, the area of the forming part 10 has a certain area that allows the force exerted by abutting the forming part 10 against the surface of the organism 1 to be scattered over the area, thus preventing a situation in which the organism is deformed for each measurement due to variations in the force exerted by the forming part 10 being contacted against the surface of the organism 1. By these effects, the shape of the organism can be kept constant, and therefore variations in the shape of the organism for each measurement can be prevented, thus making it possible to carry out measurements with high accuracy. Furthermore, it is not necessarily required to form the surface of the organism 1 into a flat shape, and even if the area of the forming part 10 contacting the organism is concaved as shown in FIG. 3 for example, the shape of the organism can be kept constant, and therefore measurements can be carried out with high reproducibility.

Also, the degree of reflection of the face of the forming part 10 contacting the surface of the organism 1 is almost 0, thereby making it possible to prevent a situation in which light going out of the organism through the surface of the organism 1 goes back into the organism. Thus, of light 13 received in the light receiving part 12, the amount of component propagating through a shallow area in the organism, can be reduced, and therefore correlation between the amount of received light and the thickness of subcutaneous fat is improved.

Also, the wavelength of the light source part 11 can be selected to meet the absorption band of a substance of interest, and light reception characteristics of the light receiving part 12 can be selected to meet the absorption band of the substance of interest, thereby making it possible to measure the concentration of oxygen in the organism and the concentration of glucose in the organism by the amount of received light. In the case of the concentration of oxygen in the organism, the light source part 11 having a light source element of two wavelengths: a wavelength of about 450 nm to 800 nm and a wavelength of about 800 nm to 1000 nm is used, or the light receiving part 12 comprising two or more light receiving sensors having sensitivity characteristics in two wavelengths: a wavelength of about 450 nm to 800 nm and a wavelength of about 800 nm to 1000 nm is provided, thereby making it possible to measure the concentration of oxygen in the organism with high accuracy as in the case of the subcutaneous fat 5. Also, as for the concentration of glucose in the organism, the light source part 11 constituted by a light source element of a wavelength of about 1000 nm to 2000 nm and the light receiving part 12 constituted by a light receiving sensor having a sensitivity in a wavelength of about 1000 nm to 2000 nm are used, thereby making it possible to carry out measurements with high accuracy.

EMBODIMENT 2

Figure 4:
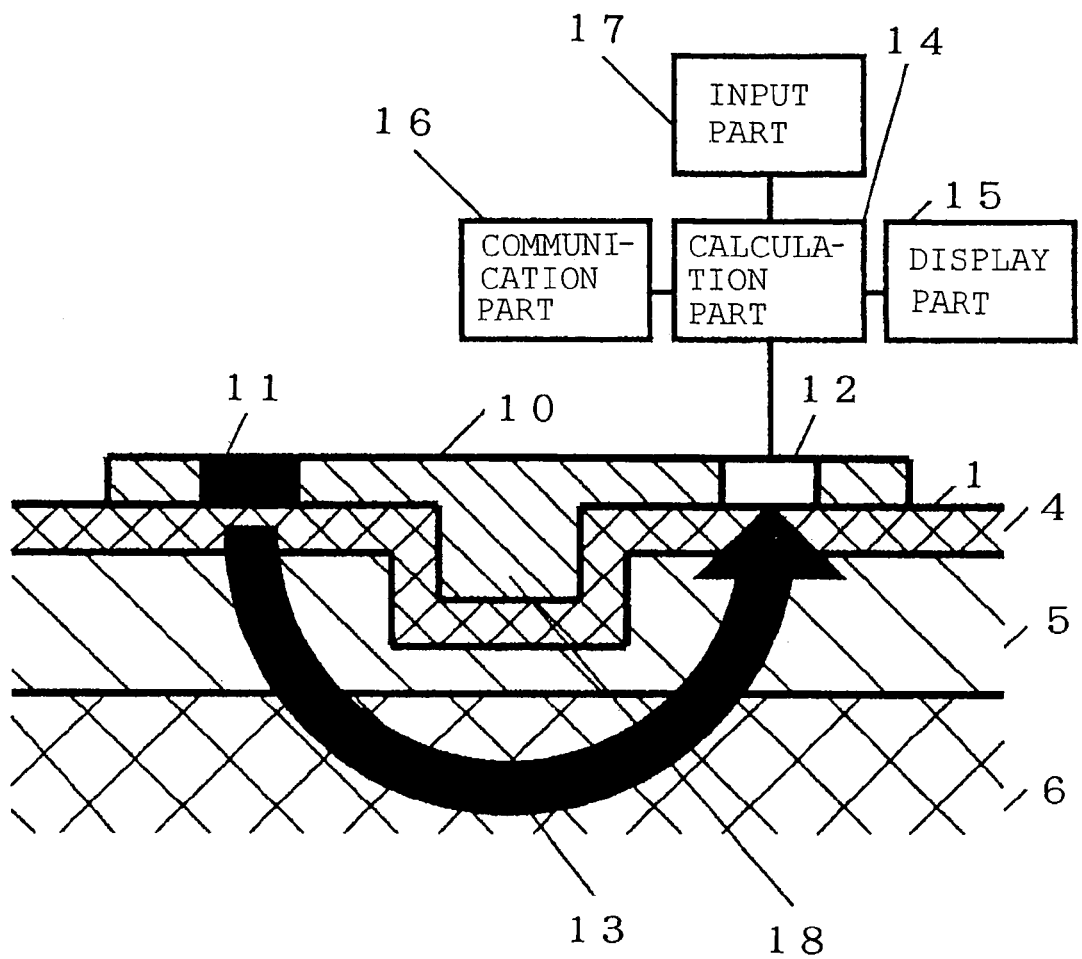
FIG. 4 is a block diagram of the apparatus of measuring biological information using light in Embodiment 2 of the present invention.
Figure 5:
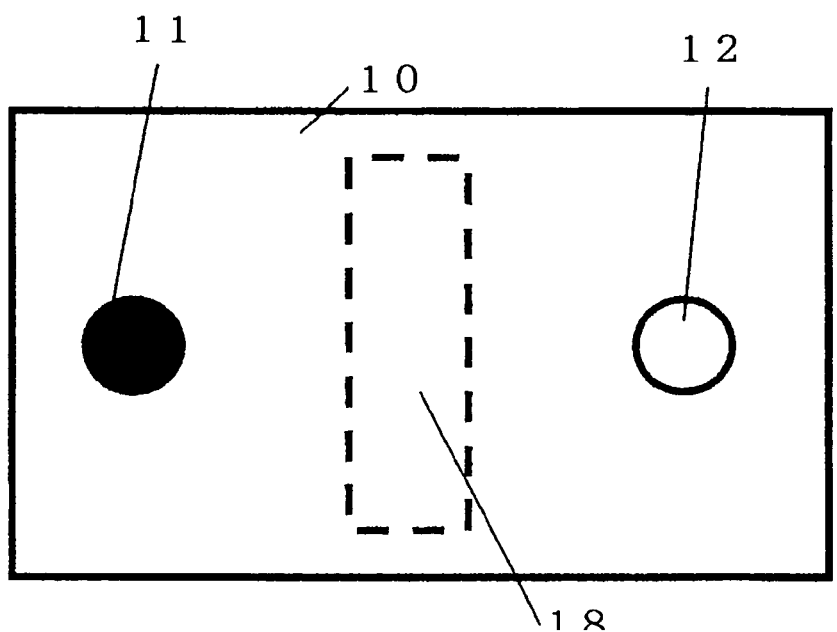
FIG. 5 is a top view showing the forming part of the apparatus of measuring biological information using light in Embodiment 2 of the present invention.

FIG. 4 is a block diagram of the apparatus of measuring biological information using light in Embodiment 2 of the present invention. Also, FIG. 5 shows the forming part 10 seen from the above. The protrusion part 18 that is 5 mm wide, 50 mm long and 5 mm high is provided between the light source part 11 and the light receiving part 12 on the forming part 10 flatting the surface of the organism 1.

Here, it is preferable that the forming part 10 is a rectangle being about 25 mm long and 40 mm wide, and the area of the forming part 10 is 1000 $mm^2$ or greater, for example, although not specifically limited. However, the forming part 10 is not necessarily a rectangle. The longitudinal, lateral and vertical dimensions of the protrusion part 18 are not necessarily limited to the above values.

The forming part 10 and the protrusion part 18 are made of material such as black ABS in which the degree of reflection of the face contacting the surface of the organism 1 is substantially 0 in the range of wavelengths of light emitted from the light source part 11. "Substantially 0" in this case refers to a degree of reflection of about 2% or smaller. Furthermore, as another method, the forming part 10 may be coated or painted with a material with the degree of reflection of about 2% or smaller.

The surface of the organism 1 is deformed because it is pressed by the forming part 10 and the protrusion part 18. However, because the width of the protrusion part 18 is small, the surface of the organism 1 is deformed such that only the portion just below the protrusion part 18 of the subcutaneous fat 5, which is the softest of organic tissues, is pushed out to the area where the protrusion part 18 does not exist as shown in FIG. 4, and only the thickness of the subcutaneous fat 5 is locally changed in the organism.

The light source part 11, the light receiving part 12, the calculation part 14, the display part 15, the communication part 16 and the input part 17 of the apparatus of measuring biological information using light in this embodiment have configurations and functions similar to those of the apparatus of measuring biological information using light in Embodiment 1.

According to the apparatus of measuring biological information using light in this embodiment, because the surface of the organism 1 is formed into a flat shape by the forming part 10, and the degree of reflection of the face of the forming part 10 contacting the surface of the organism 1 is almost 0, the same effects as those of the apparatus of measuring biological information using light in Embodiment 1 can be obtained.

In addition, in the example of prior art, the distance between the light source part 11 and the light receiving part 12 should be increased for obtaining information of a deeper area in the organism, but in this embodiment, light that has propagated through a shallow area near the surface of the organism 1 is prevented from propagating to the light receiving part 12 by the protrusion part 18, and therefore a larger amount of component of light that has propagated through a deeper area in the organism is received in the light receiving part 12 compared to the case where the protrusion part 18 is not provided. Consequently, the light received in the light receiving part 12 has a larger amount of information of the thickness of the subcutaneous fat 5 compared to the case where the protrusion part 18 is not provided. Thus, only the light that has propagated through a deeper area in the organism can be received without increasing the distance between the light source part 11 and the light receiving part 12. As a result, the measurement optical system can be downsized. In addition, the area of the organism to be measured decreases, and thereby the influence of local variations in thickness of tissues can be alleviated, resulting in improved measurement accuracy. In other words, the area through which light passes decreases, and thereby the measurement accuracy is improved.

Also, as in the case of Embodiment 1, the wavelength of the light source part 11 can be selected to meet the absorption band of a substance of interest, and light reception characteristics of the light receiving part 12 can be selected to meet the absorption band of the substance of interest, thereby making it possible to measure the concentration of oxygen in the organism and the concentration of glucose in the organism by the amount of received light.

EMBODIMENT 3

Figure 6:
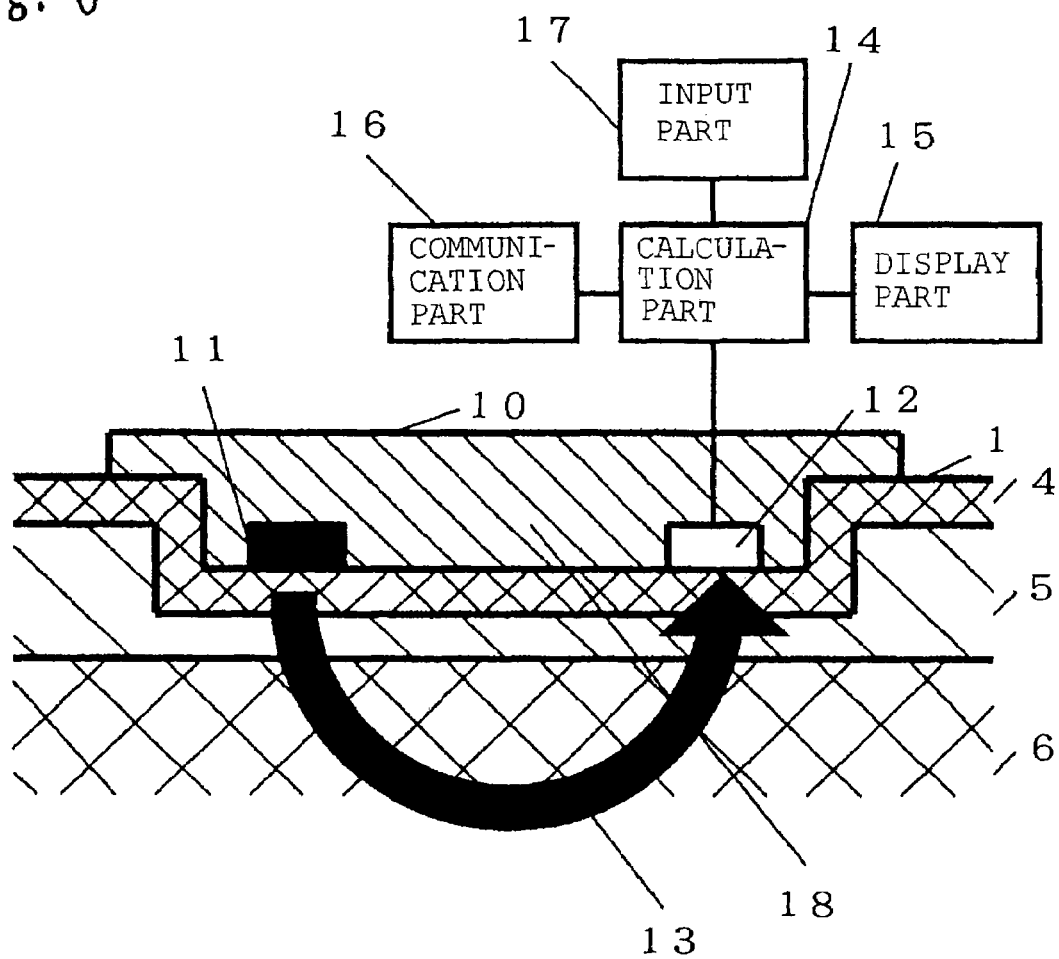
FIG. 6 is a block diagram of the apparatus of measuring biological information using light in Embodiment 3 of the present invention.
Figure 7:
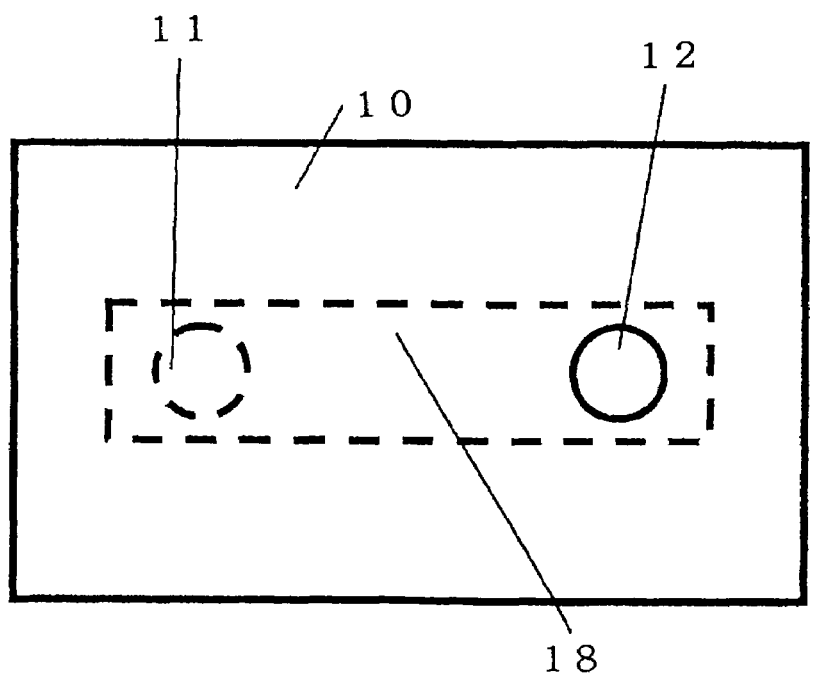
FIG. 7 is a top view showing the forming part of the apparatus of measuring biological information using light in Embodiment 3 of the present invention.

FIG. 6 is a block diagram of the apparatus of measuring biological information using light in Embodiment 3 of the present invention. Also, FIG. 7 shows the forming part 10 seen from the above. The apparatus of measuring biological information using light in this embodiment has the protrusion part 18 being 5 mm long, 50 mm wide and 5 mm high on the forming part 10 forming the surface of the organism 1 into a flat shape.

Here, it is preferable that the forming part 10 is a rectangle being about 25 mm long and 40 mm wide, and the area of the forming part 10 is 1000 mm$^2$ or greater, for example, although not specifically limited. However, the forming part 10 is not necessarily a rectangle. The longitudinal, lateral and vertical dimensions of the protrusion part 18 are not necessarily limited to the above values. The light source part 11 and the light receiving part 12 are placed in the protusion part 18.

The surface of the organism is deformed because it is pressed by the forming part 10 and the protrusion part 18. However, because the width of the protrusion part 18 is small, the surface of the organism 1 is deformed such that only the softest portion just below the protrusion part 18 of the subcutaneous fat 5 is pushed out to the area where the protrusion part 18 does not exist as shown in FIG. 6, and only the thickness of the subcutaneous fat 5 is locally changed.

The forming part 10 and the protrusion part 18 are made of material such as black ABS in which the degree of reflection of the face contacting the surface of the organism 1 is substantially 0 in the range of wavelengths of light emitted from the light source part. "Substantially 0" in this case refers to a degree of reflection of 2% or smaller. Furthermore, as another method, the forming part 10 may be coated or painted with a material with the degree of reflection of 2% or smaller.

The light source part 11, the light receiving part 12, the calculation part 14, the display part 15, the communication part 16 and the input part 17 of the apparatus of measuring biological information using light in this embodiment have configurations and functions similar to those of the apparatus of measuring biological information using light in Embodiment 1.

According to the apparatus of measuring biological information using light in this embodiment, because the surface of the organism 1 is formed into a flat shape by the forming part 10, and the degree of reflection of the face of the forming part 10 contacting the surface of the organism 1 is almost 0, the same effects as those of the apparatus of measuring biological information using light in Embodiment 1 can be obtained.

In addition, due to the presence of the light source part 11 and the light receiving part in the protrusion part 18, the thickness of the subcutaneous fat 5 through which light substantially propagates is reduced compared to the actual thickness by a level equivalent to the height of the protrusion part 18. As the thickness of the subcutaneous fat 5 to be measured increases, the distance between the light source part 11 and the light receiving part 12 should be increased, and therefore conversely, by making the subcutaneous fat 5 thinner, the distance between the light source 11 and the light receiving part 12 can be reduced. Then, the original thickness of subcutaneous fat can be calculated by adding a thickness equivalent to the protrusion part 18 to the measured thickness of subcutaneous fat. That is, the distance between the light source part 11 and the light receiving part 12 can be reduced compared to the case where the protrusion part 18 is not provided. As a result, the measurement optical system can be downsized. In addition, the area of the organism to be measured decreases, and thereby the influence of local variations in thickness of tissues can be alleviated, resulting in improved measurement accuracy.

Also, as in the case of Embodiment 1, the wavelength of the light source part 11 can be selected to meet the absorption band of a substance of interest, and light reception characteristics of the light receiving part 12 can be selected to meet the absorption band of the substance of interest, thereby making it possible to measure the concentration of oxygen in the organism and the concentration of glucose in the organism by the amount of received light.

EMBODIMENT 4

Figure 8:
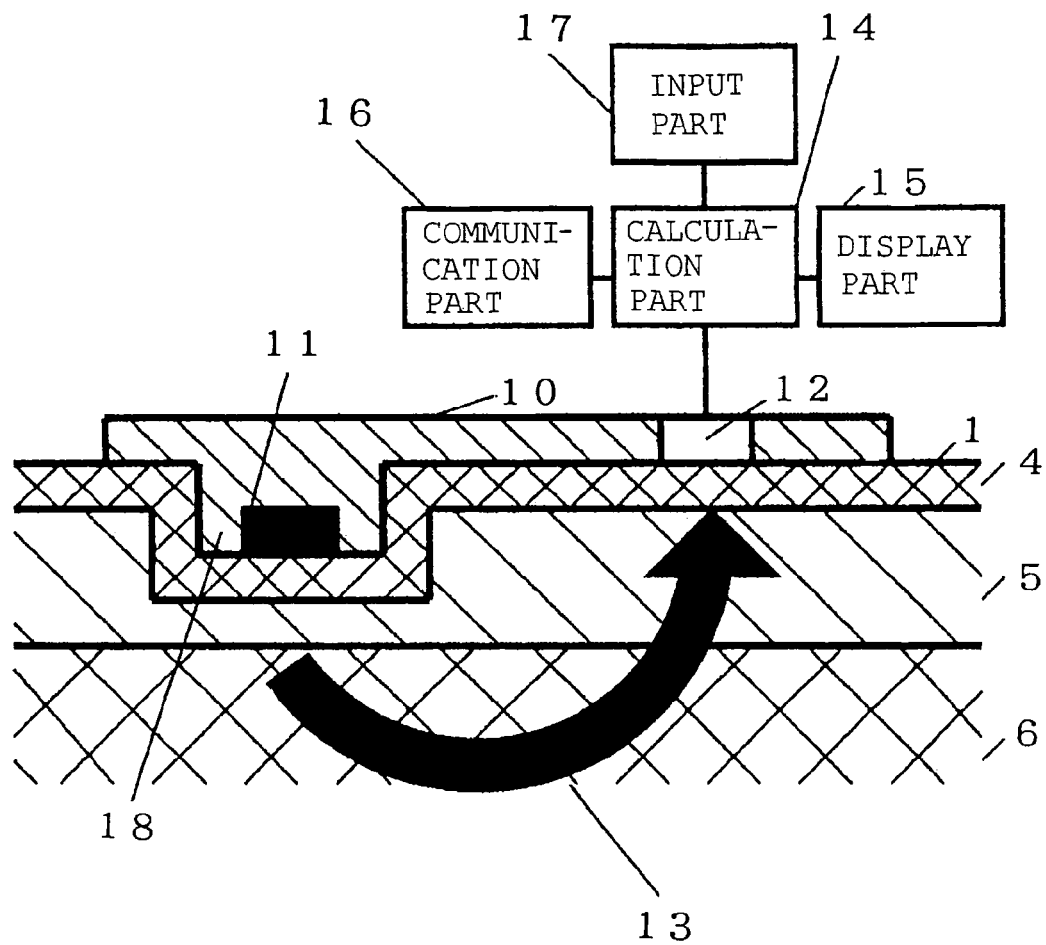
FIG. 8 is a block diagram of the apparatus of measuring biological information using light in Embodiment 4 of the present invention.
Figure 9:
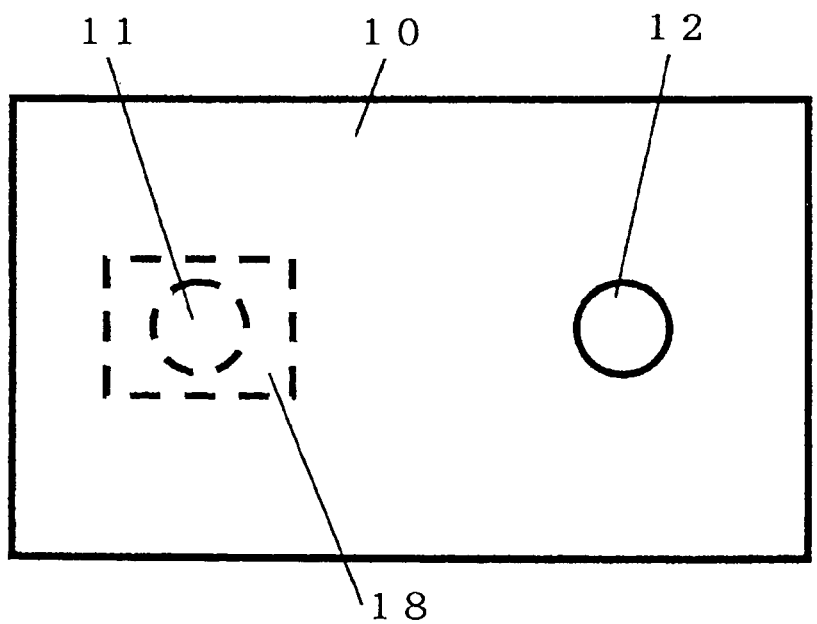
FIG. 9 is a top view showing the forming part of the apparatus of measuring biological information using light in Embodiment 4 of the present invention.

FIG. 8 is a block diagram of the apparatus of measuring biological information using light in Embodiment 4 of the present invention. Also, FIG. 9 shows the forming part 10 seen from the above. The apparatus of measuring biological information using light in this embodiment has the protrusion part 18 being 5 mm long, 5 mm wide and 5 mm high and the light receiving part 12 on the forming part 10 forming the surface of the organism 1 into a flat shape.

Here, it is preferable that the forming part 10 is a rectangle being about 25 mm long and 40 mm wide, and the area of the forming part 10 is 1000 mm² or greater, for example, although not specifically limited. However, the forming part 10 is not necessarily a rectangle. The longitudinal, lateral and vertical dimensions of the protrusion part 18 are not necessarily limited to the above values. The light source part 11 is placed in the protrusion part 18.

The surface of the organism 1 is deformed because it is pressed by the forming part 10 and the protrusion part 18. However, because the width of the protrusion part 18 is small, the surface of the organism 1 is deformed such that only the portion just below the protrusion part 18 of the subcutaneous fat 5 is pushed out to the area where the protrusion part 18 does not exist as shown in FIG. 8, and only the thickness of the subcutaneous fat 5 is locally changed.

The forming part 10 and the protrusion part 18 are made of material such as black ABS in which the degree of reflection of the face contacting the surface of the organism 1 is substantially 0 in the range of wavelengths of light emitted from the light source part. "Substantially 0" in this case refers to a degree of reflection of about 2% or smaller. Furthermore, as another method, the forming part 10 may be coated or painted with a material with the degree of reflection of about 2% or smaller.

The light source part 11, the light receiving part 12, the calculation part 14, the display part 15, the communication part 16 and the input part 17 of the apparatus of measuring biological information using light in this embodiment have configurations and functions similar to those of the apparatus of measuring biological information using light in Embodiment 1.

According to the apparatus of measuring biological information using light in this embodiment, because the surface of the organism 1 is formed into a flat shape by the forming part 10, and the degree of reflection of the face of the forming part 10 contacting the surface of the organism 1 is almost 0, the same effects as those of the apparatus of measuring biological information using light in Embodiment 1 can be obtained.

In addition, due to the presence of the light source part 11 in the protrusion part 18, the depth of the area in the organism through which light substantially propagates is increased by a level equivalent to the height of the protrusion part 18. Thus, a larger amount of component of light that has propagated through a deeper area in the organism is received in the light receiving part 12, compared to the case where the protrusion part 18 is not provided. Consequently, the light received in the light receiving part 12 has a larger amount of information of the thickness of the subcutaneous fat 5 compared to the case where the protrusion part 18 is not provided. Therefore, only the light that has propagated through a deeper area in the organism can be received without increasing the distance between the light source part 11 and the light receiving part 12, thus making it possible to downsize the measurement optical system. In addition, the area of the organism to be measured decreases, and thereby the influence of local variations in thickness of tissues can be alleviated, resulting in improved measurement accuracy.

Also, as in the case of Embodiment 1, the wavelength of the light source part 11 can be selected to meet the absorption band of a substance of interest, and light reception characteristics of the light receiving part 12 can be selected to meet the absorption band of the substance of interest, thereby making it possible to measure the concentration of oxygen in the organism and the concentration of glucose in the organism by the amount of received light.

EMBODIMENT 5

Figure 10:
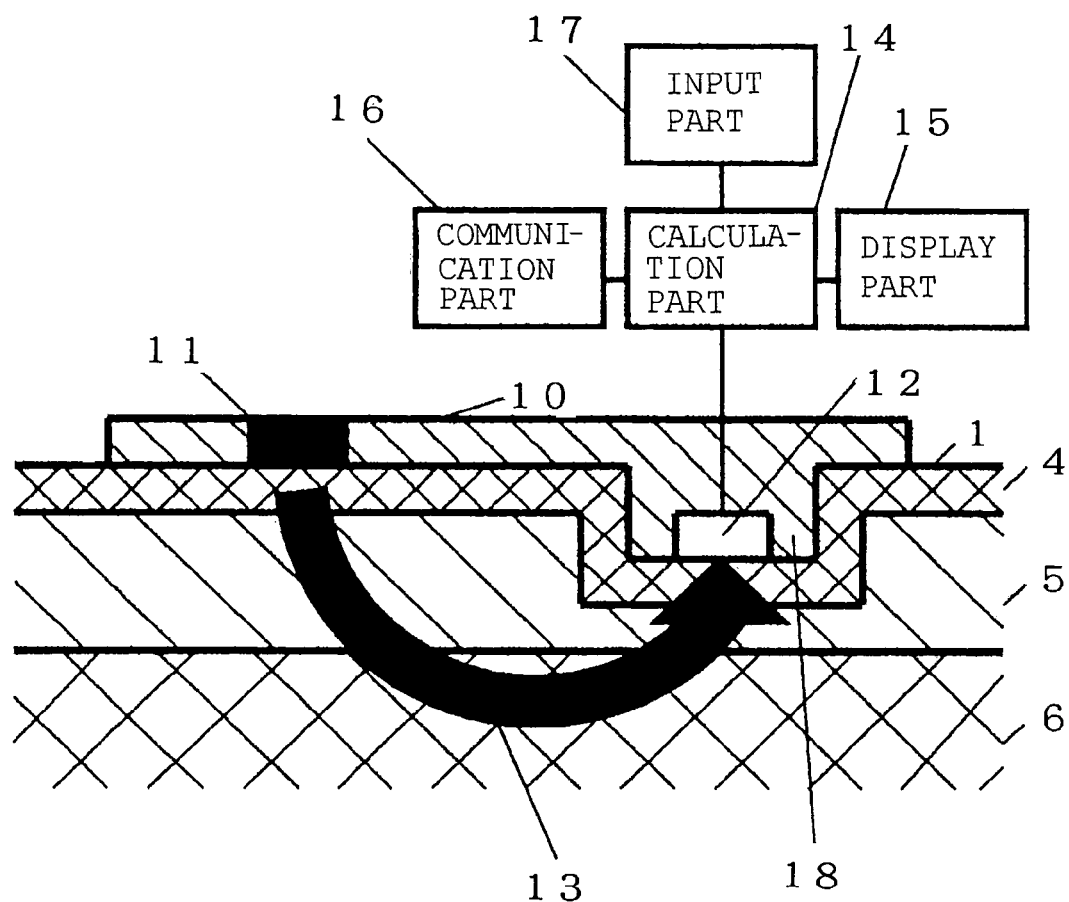
FIG. 10 is a block diagram of the apparatus of measuring biological information using light in Embodiment 5 of the present invention.
Figure 11:
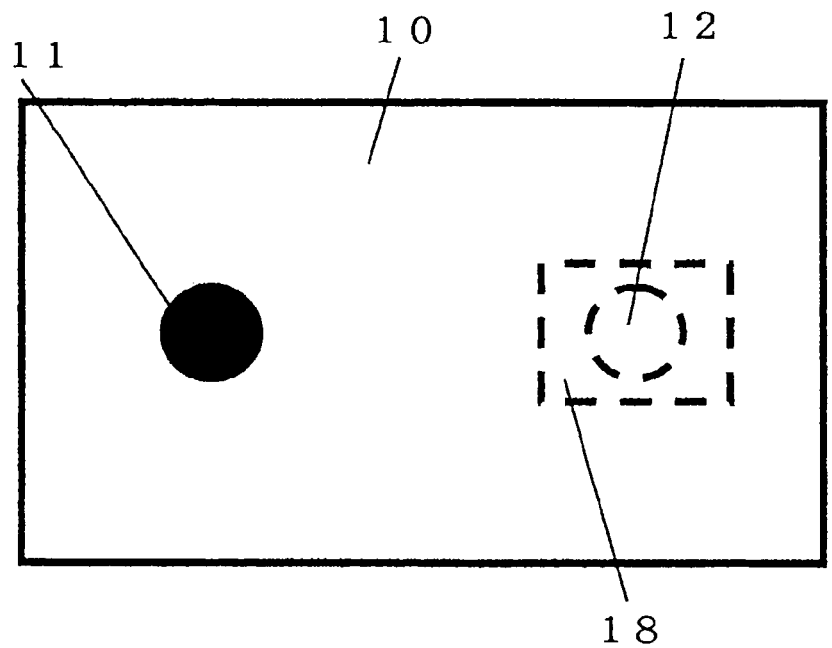
FIG. 11 is a top view showing the forming part of the apparatus of measuring biological information using light in Embodiment 5 of the present invention.

FIG. 10 is a block diagram of the apparatus of measuring biological information using light in Embodiment 5 of the present invention. Also, FIG. 11 shows the forming part 10 seen from the above. Here, it is preferable that the forming part 10 is a rectangle being 25 mm long and 40 mm wide, and the area of the forming part 10 is about 1000 mm² or greater, for example, although not specifically limited. However, the forming part 10 is not necessarily a rectangle. In addition, the protrusion part 18 being about 5 mm long, 5 mm wide and 5 mm high and the light source part 11 are provided on the forming part 10 forming the surface of the organism 1 into a flat shape. The longitudinal, lateral and vertical dimensions of the protrusion part 18 are not necessarily limited to the above values. Also, the light receiving part 12 is placed on the protrusion part 18.

The surface of the organism is deformed because it is pressed by the forming part 10 and the protrusion part 18. However, because the width of the protrusion part 18 is small, the surface of the organism 1 is deformed such that only the softest portion just below the protrusion part 18 of the subcutaneous fat 5 is pushed out to the area where the protrusion part 18 does not exist as shown in FIG. 10, and only the thickness of the subcutaneous fat 5 is locally changed.

The forming part 10 and the protrusion part 18 are made of material such as black ABS in which the degree of reflection of the face contacting the surface of the organism 1 is substantially 0 in the range of wavelengths of light emitted from the light source part. "Substantially 0" in this case refers to a degree of reflection of about 2% or smaller. Furthermore, as another method, the forming part 10 may be coated or painted with a material with the degree of reflection of about 2% or smaller.

The light source part 11, the light receiving part 12, the calculation part 14, the display part 15, the communication part 16 and the input part 17 of the apparatus of measuring biological information using light in this embodiment have configurations and functions similar to those of the apparatus of measuring biological information using light in Embodiment 1.

According to the apparatus of measuring biological information using light in this embodiment, because the surface of the organism 1 is formed into a flat shape by the forming part 10, and the degree of reflection of the face of the forming part 10 contacting the surface of the organism 1 is almost 0, the same effects as those of the apparatus of measuring biological information using light in Embodiment 1 can be obtained.

In addition, due to the presence of the light receiving part 12 in the protrusion part 18, the depth of the area in the organism through which light substantially propagates is increased by a level equivalent to the height of the protrusion part 18. Thus, a larger amount of component of light that has propagated through a deeper area in the organism is received in the light receiving part 12, compared to the case where the protrusion part 18 is not provided. Consequently, the light received in the light receiving part 12 has a larger amount of information of the thickness of the subcutaneous fat 5 compared to the case where the protrusion part 18 is not provided. Therefore, only the light that has propagated through a deeper area in the organism can be received without increasing the distance between the light source part 11 and the light receiving part 12, thus making it possible to downsize the measurement optical system. In addition, the area of the organism to be measured decreases, and thereby the influence of local variations in thickness of tissues can be alleviated, resulting in improved measurement accuracy.

Also, as in the case of Embodiment 1, the wavelength of the light source part 11 can be selected to meet the absorption band of a substance of interest, and light reception characteristics of the light receiving part 12 can be selected to meet the absorption band of the substance of interest, thereby making it possible to measure the concentration of oxygen in the organism and the concentration of glucose in the organism by the amount of received light.

EMBODIMENT 6

Figure 12:
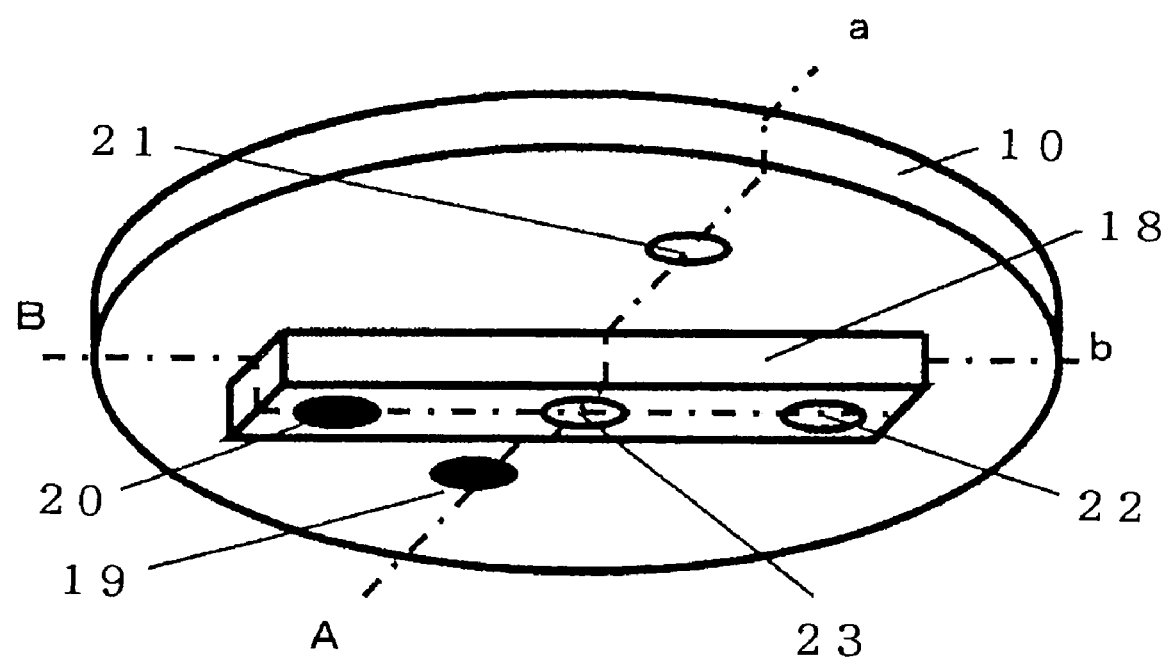
FIG. 12 is a perspective view showing the forming part of the apparatus of measuring biological information using light in Embodiment 6 of the present invention.

FIG. 12 is a perspective view of the forming part 10 of the apparatus of measuring biological information using light in Embodiment 5 of the present invention.

The forming part 10 is substantially flat, and the protrusion part 18 is placed at almost the center thereof. The forming part 10 has a circular shape with the diameter of about 60 mm. The protrusion part 18 is about 5 mm long, 50 mm wide and 5 mm high. Here, the forming part 10 does not necessarily have a circular shape, and its area is preferably about 1000 mm² or greater. Also, the longitudinal, lateral and vertical dimensions of the protrusion part 18 are not necessarily limited to the above values.

A first light source part 19 is placed on an area of the forming part 10 excluding the protrusion part 18 and at a distance of about 15 mm from the center of the protrusion part 18 (at first predetermined location), and a second light source part 20 is placed at one end of the protrusion part 18 and at a distance of about 15 mm from the center of the protrusion part 18 (second predetermined location). A first light receiving part 21 is placed at a distance of about 15 mm from the center of the protrusion part 18 (at third predetermined location) on the side opposite to the first light source part 19, a second light receiving part 22 is placed on the side opposite to the second light source on the protrusion part 18 and at a distance of about 15 mm from the center of the protrusion part 18 (at fourth predetermined location), and a third light receiving part 23 is placed at the center of the protrusion part 18 (at fifth predetermined location). Here, the locations of the light source parts and the light receiving parts are not necessarily limited to the above values.

Figure 13:
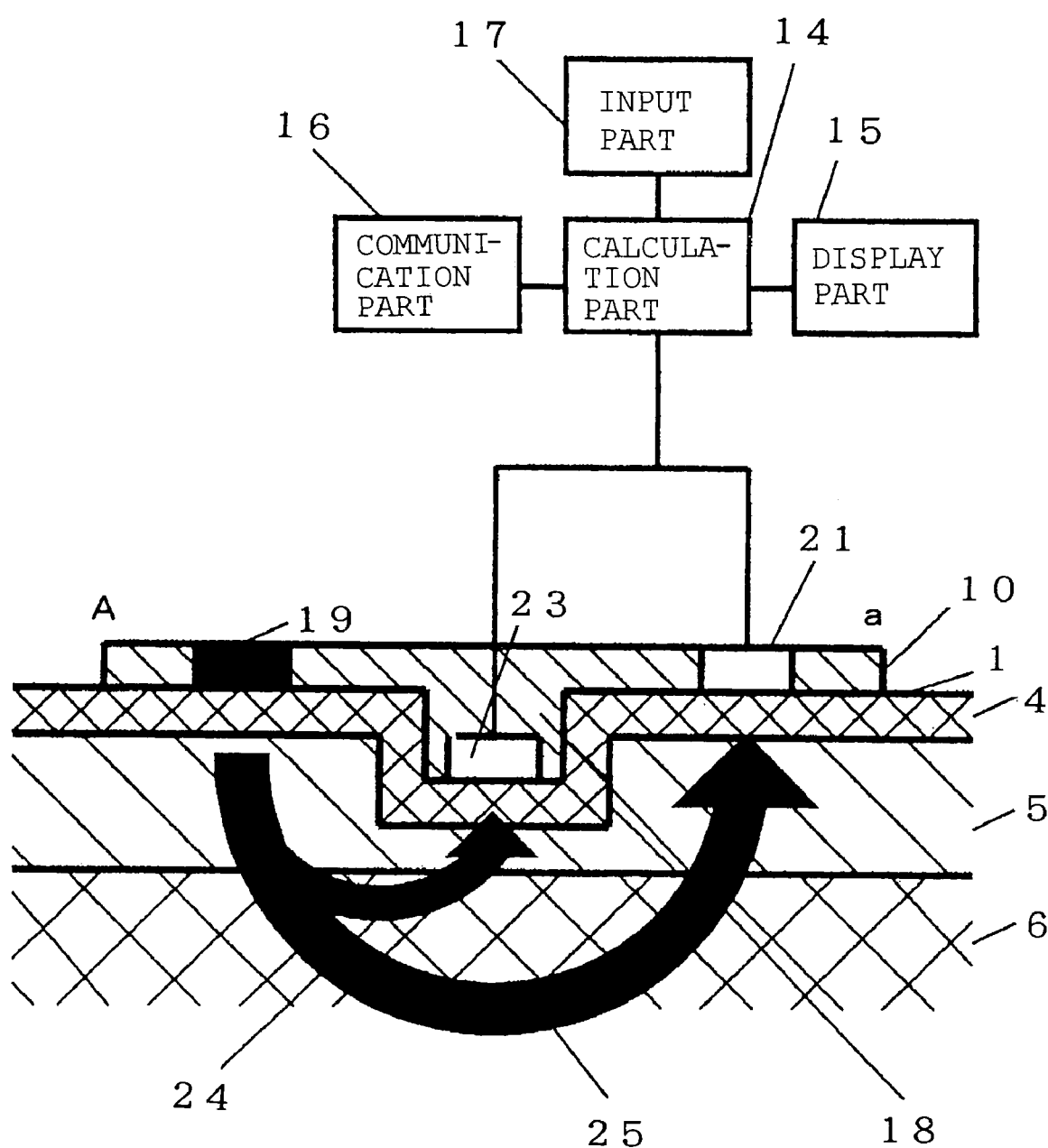
FIG. 13 is a block diagram of the apparatus of measuring biological information using light in Embodiment 6 of the present invention.
Figure 14:
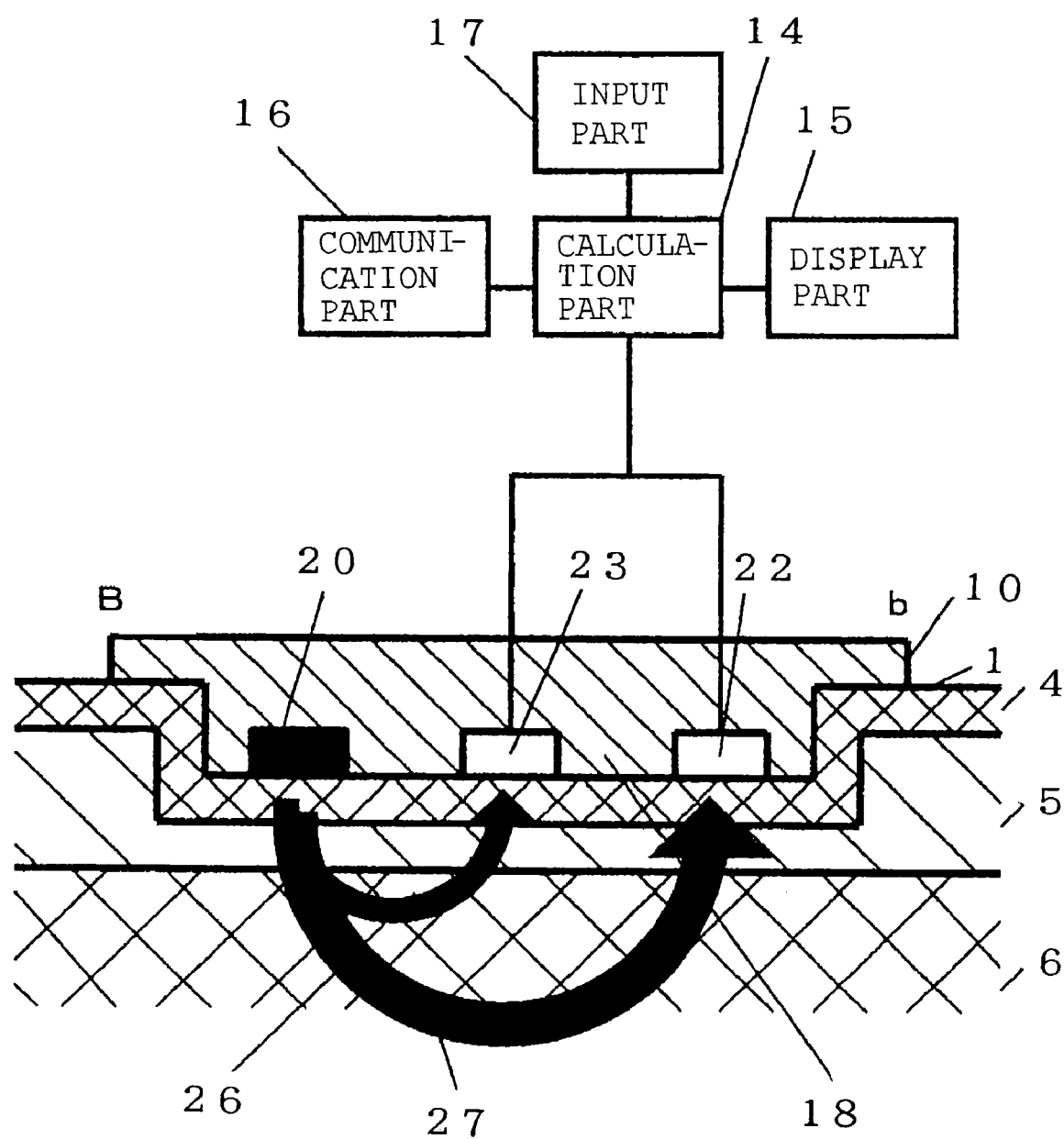
FIG. 14 is a block diagram showing a different cross-section of the apparatus of measuring biological information using light in Embodiment 6 of the present invention.

Also, FIGS. 13 and 14 are block diagrams of the apparatus of measuring biological information using light in this embodiment. FIG. 13 is a sectional view taken along the A-a line when the forming part 10 is contacted against the surface of the organism 1, and similarly FIG. 14 is a sectional view taken along the B-b line when the forming part 10 is contacted against the surface of the organism 1.

The surface of the organism 1 is deformed because it is pressed by the forming part 10 and the protrusion part 18. However, because the width of the protrusion part 18 is small, the surface of the organism 1 is deformed such that only the portion just below the protrusion part 18 of the subcutaneous fat 5 is pushed out to the area where the protrusion part 18 does not exist as shown in FIGS. 13 and 14, and only the thickness of the subcutaneous fat 5 is locally changed.

The forming part 10 and the protrusion part 18 are made of material such as black ABS in which the degree of reflection of the face contacting the surface of the organism 1 is substantially 0 in the range of wavelengths of light emitted from the first light source part 19 and the second light source part 20. "Substantially 0" in this case refers to a degree of reflection of 2% or smaller. Furthermore, as another method, the forming part 10 may be coated or painted with a material with the degree of reflection of about 2% or smaller.

A light source such as an LED light source, laser light source or bulb is incorporated in each of the first light source part 19 and second light source part 20. The central wavelength of light outputted from the first light source part 19 and the second light source part 20 is in the range of from about 500 nm to 1000 nm or from about 1000 nm to 2000 nm. Also, the first light source part 19 and the second light source part 20 may have a configuration in which the light source is separated from the surface of the organism 1, and light is be guided from the light source to the surface of the organism 1 by the optical fibers or the like.

The first light receiving part 21, the second light receiving part 22 and the third light receiving part 23 each comprise a light receiving sensor such as a photodiode, avalanche photodiode or CdS cell. Also, each of the light receiving parts may have a configuration in which light is guided between the surface of the organism 1 and the light receiving sensor by optical fibers or the like.

The calculation part 14 calculates the thickness of subcutaneous fat according to the amount of light received in the light receiving part 21, the light receiving part 22 and the third light receiving part 23, and the display part 15 displays the thickness of subcutaneous fat or the like as biological information determined by the calculation part 14. Also, the communication part 16 communicates information of the thickness of subcutaneous fat as biological information determined by the calculation part 14 and control data such as start of measurement to and from external apparatuses. Also, by the input part 17, measurement conditions such as the measured site, sex, age, height and weight of a subject may be inputted, and control such as start of measurement may be performed.

Operations of the apparatus of measuring biological information using light in this embodiment will be described.

In FIG. 13, light emitted from the first light source part 19 propagates through the skin 4, the subcutaneous fat 5 and the muscle 6 while it is scattered and absorbed. By carrying out measurements using an amount of light 24 received in the third light receiving part 23, of light that has propagated through the inside of the organism, the same effects as those of Embodiment 5 can be obtained. Also, by using an amount of light 25 received in the first light receiving part 21, of light that has propagated through the inside of the organism, only the light that has propagated through a deeper area in the organism can be received without increasing the distance between the first light source part 19 and the first light receiving part 21 as in the case of Embodiment 2, thus making it possible to downsize the measurement optical system. In addition, the area of the organism to be measured decreases, and thereby the influence of local variations in thickness of tissues can be alleviated, resulting in improved measurement accuracy. In addition, by making corrections in the same manner as the example of prior art using light received in the third receiving part 23 provided in the protrusion part 18, measurements can be carried out with high accuracy.

In FIG. 14, light emitted from the second light source part 20 propagates through the skin 4, the subcutaneous fat 5 and the muscle 6 while it is scattered and absorbed. Speaking of amounts of light 26 received in the third light receiving part 23 and light 27 received in the second light receiving part 22, of light that has propagated through the inside of the organism, only the light that has propagated through a deeper area in the organism can be received without increasing the distance between the second light source part 20 and the third and second light receiving parts 23 and 22 as in the case of Embodiment 3, thus making it possible to downsize the measurement optical system. In addition, the area of the organism to be measured decreases, and thereby the influence of local variations in thickness of tissues can be alleviated, resulting in improved measurement accuracy. In addition, by making corrections in the same manner as the example of prior art using light received in the third receiving part 23 provided in the protrusion part 18, measurements can be carried out with high accuracy.

Also, by averaging in the calculation part 14 the thicknesses of subcutaneous fat determined by carrying out these two measurements at the same time, more accurate measurements can be carried out.

Also, as in the case of Embodiment 1, the wavelengths of the first light source part 19 and the second light source part 20 can be selected to meet the absorption band of a substance of interest, and light reception characteristics of the light receiving part 21, the second light receiving part 22 and the third light receiving part 23 can be selected to meet the substance of interest, thereby making it possible to measure the concentration of oxygen in the organism and the concentration of glucose in the organism by the amount of received light.

The method of measuring the thickness of subcutaneous fat using light in one embodiment of the present invention is characterized by comprising a step A of shaping the surface of an organism into a predetermined shape by applying a pressure thereto, a step B of measuring the pressure, a step C of irradiating the organism with light, a step D of receiving light propagating through the inside of the organism and outgoing from the surface of the organism, and a step E of calculating the thickness of subcutaneous fat of the organism based on the amount of light received in the step D and the pressure measured in the step B. In this way, influences based on the change in the thickness of subcutaneous fat and the change in the amount of blood in the subcutaneous fat by the pressure applied to the surface of the organism are eliminated, thereby making it possible to measure the thickness of subcutaneous fat with high reproducibility and accuracy.

Also, the method of measuring the thickness of subcutaneous fat using light in another embodiment of the present invention is characterized by comprising a step A of shaping the surface of an organism into a predetermined shape by applying a pressure thereto, a step B of detecting that the pressure reaches a predefined value, a step C of irradiating the organism with light, a step D of receiving light propagating through the inside of the organism and outgoing from the surface of the organism when it is detected in the step B that the pressure reaches the predefined value, and a step E of calculating the thickness of subcutaneous fat of the organism based on the amount of light received in the step D. The thickness of subcutaneous fat decreases as the pressure applied to the surface of the organism increases, but the thickness converges at a certain value. When the pressure at which the thickness of subcutaneous fat converges is defined as the predefined value, by applying a pressure equal to or greater than the predefined value, measurements can be carried out while thickness of subcutaneous fat is kept stable, and therefore the thickness of subcutaneous fat can be measured with high reproducibility and accuracy.

Here, if the predefined value in the step B is equal to or greater than about 1 kg, the thickness of subcutaneous fat is advantageously stabilized.

Also, if the central wavelength of light applied in the step C is in the range of from about 500 nm to 1000 nm, differences in absorption and scattering characteristics are advantageously large between respective tissues of skin and subcutaneous fat and muscle.

The apparatus of measuring the thickness of subcutaneous fat using light in one embodiment of the present invention is characterized by comprising a light source part irradiating an organism, a light receiving part receiving light propagating from the light source part through the inside of the organism and outgoing from the surface of the organism, a forming part forming the surface of the organism into a predetermined shape, a pressure measuring part measuring a pressure applied to the surface of the organism by the forming part, and a calculation part calculating the thickness of subcutaneous fat of the organism based on the amount of light received in the light receiving part and the pressure measured in the pressure measuring part. In this way, influences based on the change in the thickness of subcutaneous fat and the change in the amount of blood in the subcutaneous fat by the pressure applied to the surface of the organism are eliminated, thereby making it possible to measure the thickness of subcutaneous fat with high reproducibility and accuracy.

Also, the apparatus of measuring the thickness of subcutaneous fat using light in another embodiment of the present invention is characterized by comprising a light source part irradiating an organism, a light receiving part receiving light propagating from the light source part through the inside of the organism and outgoing from the surface of the organism, a forming part forming the surface of the organism into a predetermined shape, a pressure detecting part detecting that the pressure applied to the surface of the organism by the forming part reaches a predefined value, and a calculation part calculating the thickness of subcutaneous fat of the organism based on the amount of light received in the light receiving part when the pressure detecting part detects that the pressure reaches the predefined value. In this way, the pressure at which the thickness of subcutaneous fat converges is defined as a predefined value, and a pressure equal to or greater than the predefined value is applied to the surface of the organism, whereby measurements can be carried out while the thickness of subcutaneous fat is kept stable, thus making it possible to measure the thickness of subcutaneous fat with high reproducibility and accuracy.

Here, if the face of the forming part contacting the surface of the organism is almost flat, the pressure is advantageously applied uniformly to the surface of the organism which is the area to be measured.

Also, it is preferable that a protrusion part is provided on the face of the forming part contacting the surface of the organism, and the light source part and the light receiving part are provided in the protrusion part.

Also, a plurality of light sources are preferably provided in the light source part. Also, a plurality of light receiving elements may be provided in the light receiving part.

Also, if there area light source and a light receiving element provided so that the distance between the light source and the light receiving element is a first distance of about 15 mm to 30 mm, and a light source and a light receiving element provided so that the distance between the light source and the light receiving element is a second distance of about 35 mm to 80 mm, and the amount of received light in the light receiving element located at the first distance from the light source equals Y1, and the amount of received light in the light receiving element located at the second distance from the light source equals Y2, the thickness of subcutaneous fat of the organism is preferably calculated using the value of Y2/Y1 in the calculation part. In this way, influences of blood flows in the skin and the subcutis can be eliminated, thus making it possible to measure the thickness of subcutaneous fat with higher reproducibility and accuracy.

The method of measuring the thickness of subcutaneous fat of the present invention and the apparatus for use in the method will be described in detail below using the drawings.

EMBODIMENT 7

Figure 15:
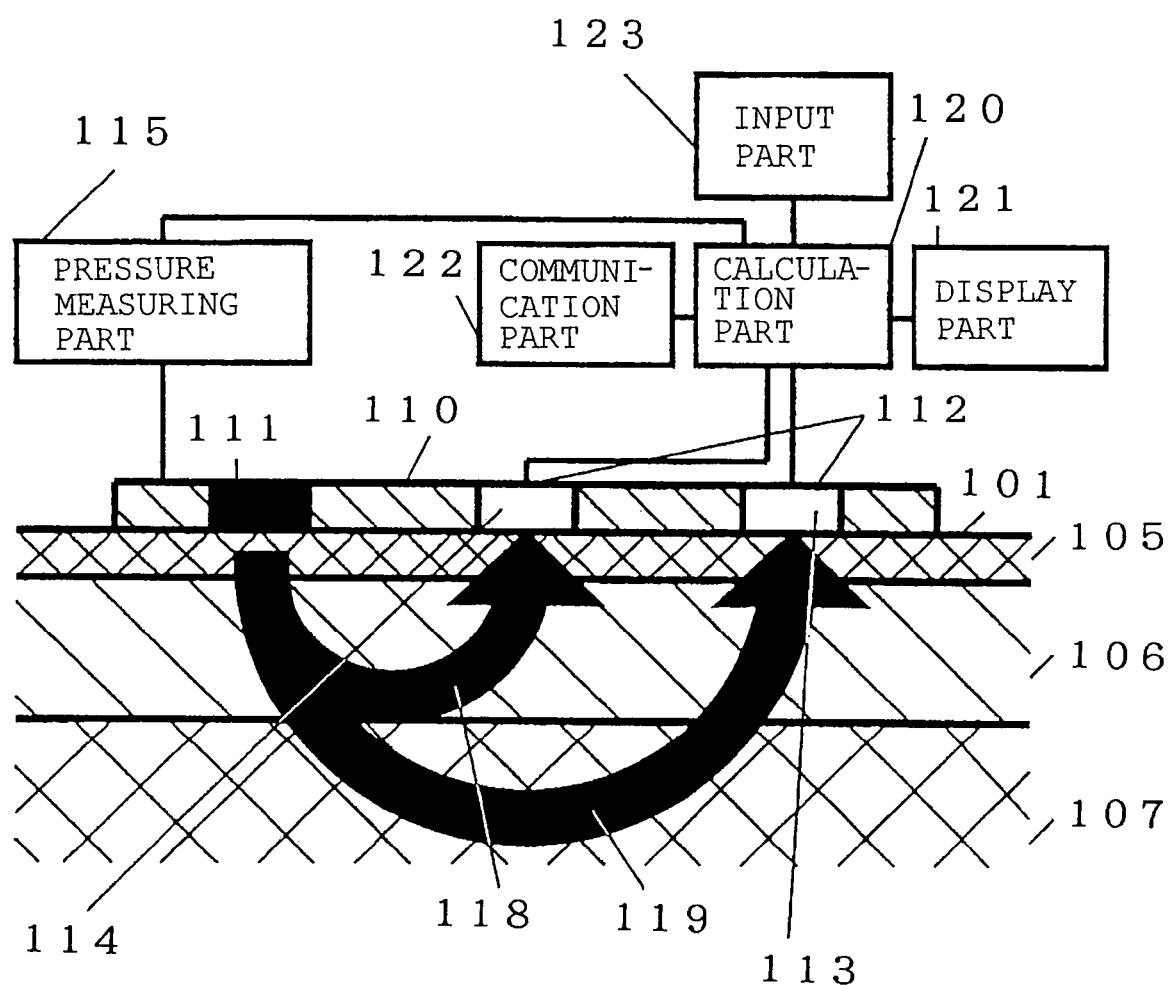
FIG. 15 is a block diagram of an apparatus of measuring the thickness of subcutaneous fat using light in Embodiment 7 of the present invention.
Figure 16:
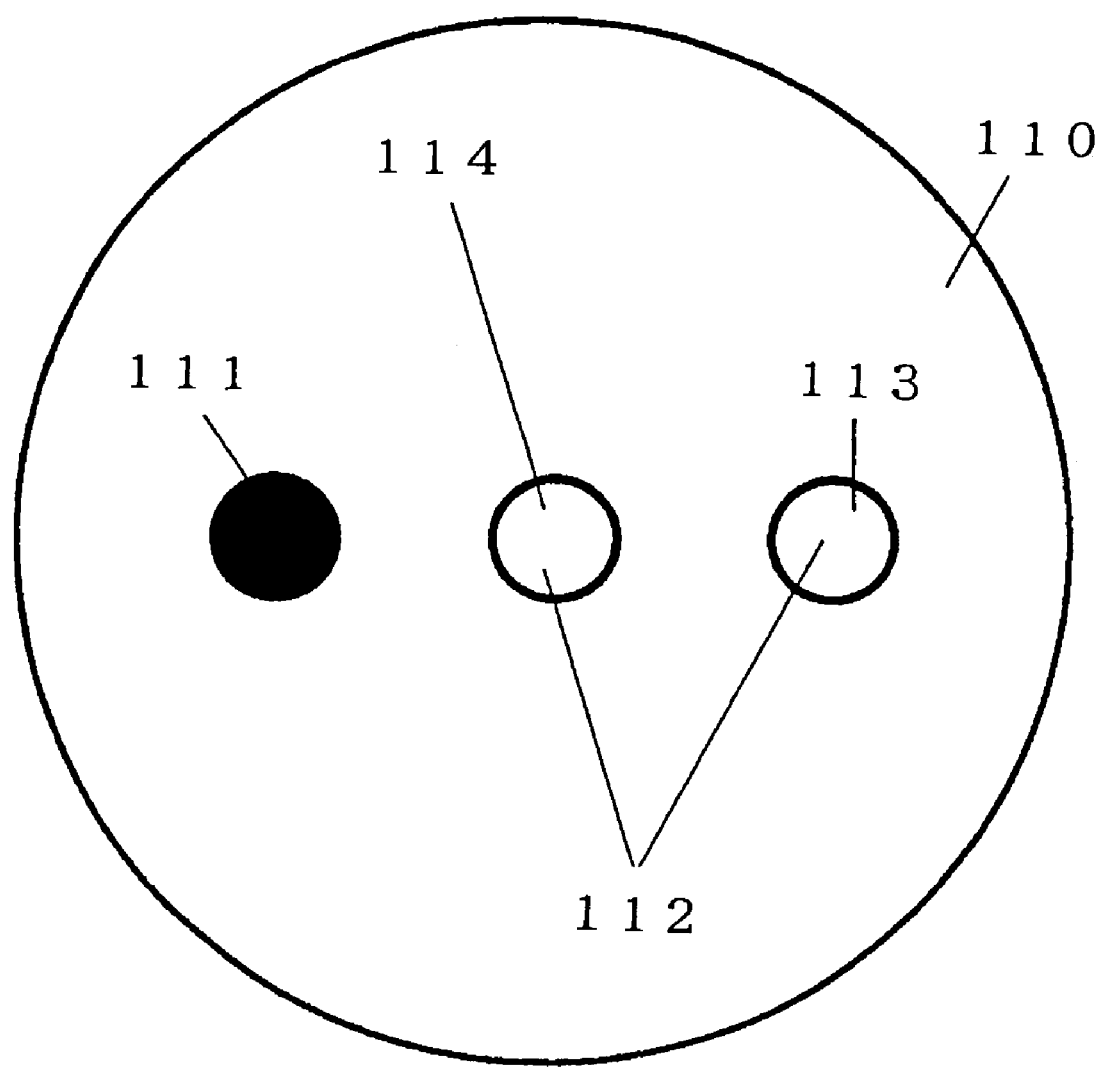
FIG. 16 is a top view of a forming part of the apparatus of measuring the thickness of subcutaneous fat using light in Embodiment 7 of the present invention, seen from the side on which it contacts the surface of the organism.

FIG. 15 is a block diagram of the apparatus of measuring the thickness of subcutaneous fat using light in Embodiment 7 of the present invention, and FIG. 16 is a top view of a forming part 110 of the apparatus of measuring the thickness of subcutaneous fat using light, seen from the side on which the forming part 110 contacts the surface of an organism 101.

The forming part 110 forming the surface of the organism 101 into a flat shape is provided on the surface of the organism 101 constituted by three layers of a skin 105, a subcutaneous fat 106 and a muscle 107. The forming part 110 has a disk shape with the diameter of 60 mm, and is made of black ABS. Furthermore, the material of the forming part 110 is not limited as long as it has a low degree of reflection of light from the light source. The forming part 110 has each corner rounded to prevent a situation in which a sharp-pointed portion abuts against the surface of the organism. Furthermore, the forming part 110 may have an oval shape or a shape of a flat plate whose corner is chamfered that is about 40 mm long and 60 mm wide.

A light source part constituted by a light source 111 and a light receiving part 112 are provided in the forming part 110. The light receiving part 112 is composed of a measuring light receiving element 113 and a correcting light receiving element 114. The distance between the measuring light receiving element 113 and the light source 111 is about 45 mm, and the distance between the correcting light receiving element 114 and the light source 111 is about 22.5 mm. The emission orifice of light emitted from the light source 111 has a diameter of about 1.5 mm$\phi$, and the incident orifice of light of the measuring light receiving element 113 and correcting light receiving element 114 has a diameter of 1.5 mm$\phi$. Furthermore, the distance between the measuring light receiving element 113 and the light source 111 is preferably in the range of from about 35 mm to 80 mm (second distance), and the distance between the correcting light receiving element 114 and the light source 111 (first distance) is preferably in the range of from about 15 mm to 30 mm. When the light source 111 is litup, an amount of received light for correction (amount of received light in the first distance Y1) is received in the correcting light receiving element 114, and an amount of received light for measurement (amount of received light in the second distance Y2) is received in the measuring light receiving element 113.

Here, the light source 111 uses a laser diode with the central wavelength about 785 nm as a light source element. Furthermore, the light source element is preferably a light source element such as a laser diode or LED with the central wavelength of about 500 nm to 1000 nm. In addition, if a light guide component such as optical fibers is used for guiding light from the light source element to the surface of the organism, heat generated in the light source element is advantageously prevented from being transferred to the surface of the organism.

The light receiving part 112 uses a photodiode as a light receiving element. Furthermore, the light receiving element may be a photoelectric conversion element such as CdS. Also, a light guide component such as optical fibers may be used for guiding light from the surface of the organism to the light receiving element.

A pressure measuring part 115 measuring a pressure applied to the surface of the organism 101 is connected to the forming part 110.

The calculation part 120 calculates the thickness of the subcutaneous fat 106 based on the amount of received light determined in the light receiving part 112 and the pressure determined in the pressure measuring part 115. The calculated thickness of the subcutaneous fat 106 is displayed on a display part 121, and is transmitted through a communication part 122 to other apparatuses as data.

Also, by inputting data such as the height, the weight, the age, the sex and the site to be measured directly from an input part 123 or from other apparatus through the communication part 122, the percent of body fat correlative with the thickness of the subcutaneous fat 6 can be calculated in the calculation part 120 and displayed on the display part 121, and data can be transferred to other apparatuses by the communication part.

The procedure of measurement will now be described. As a first operation, the forming part 110 is contacted against the surface of the organism 101 while the light source 111 is unlit.

As a second operation, if the amount of light received in the light receiving part 112 is about 100 pW or smaller, and the value of a contact force measured in the pressure measuring part 115 is about 0.1 kg or greater (about 0.35 kPa or greater when converted to pressure because the forming part 111 has a disk shape with the diameter of about 60 mm), the light source 111 is lit up when it is ensured that the entire light receiving part 112 contacts the surface of the organism and the forming part 110 is contacted against the surface of the organism, and in this state, a signal for start of measurement is inputted from the communication part 122 or input part 123.

As a third operation, the amount of received light for correction (Y1) is determined by measuring light 118 arriving at the correcting light receiving element 114, and the amount of received light for measurement (Y2) is determined by measuring light 119 arriving at the measuring light receiving element 113.

Figure 19:
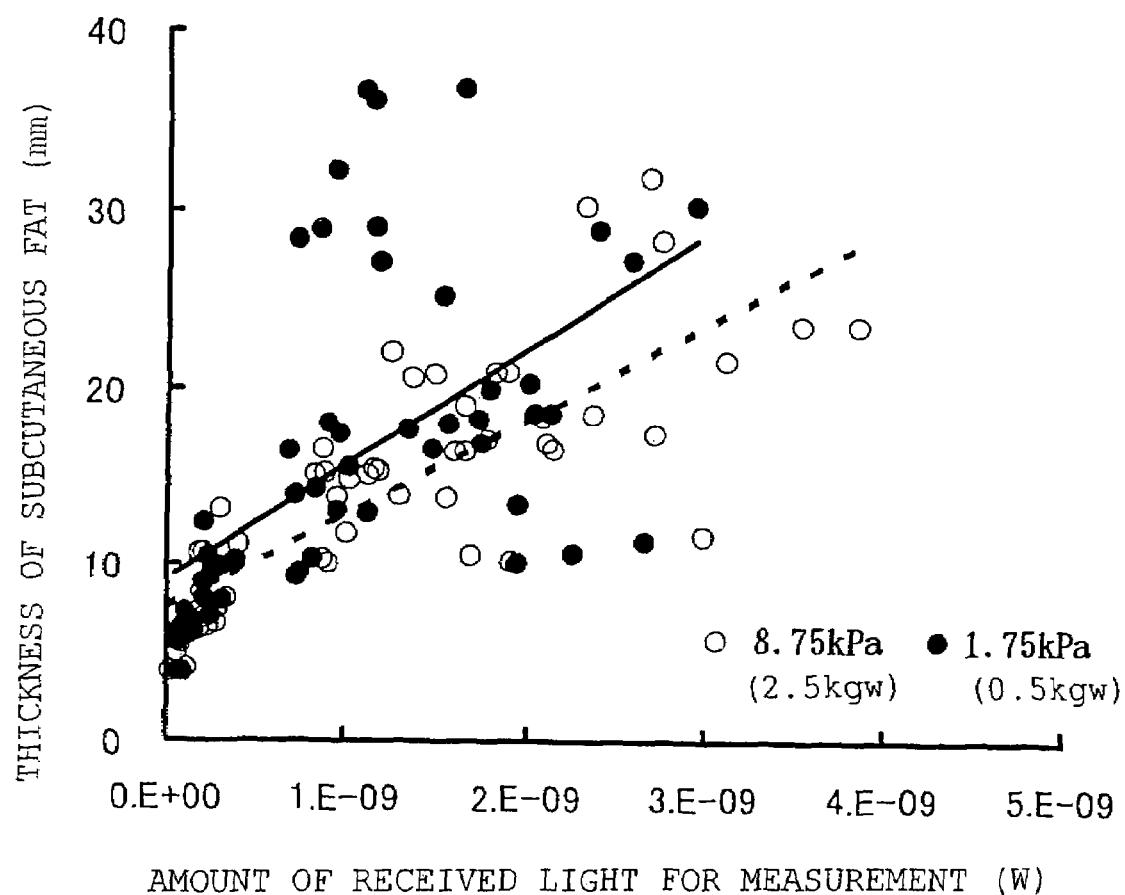
FIG. 19 shows a graph showing a relation between the amount of received light for measurement and the thickness of subcutaneous fat determined by the apparatus of measuring the thickness of subcutaneous fat using light in Embodiment 7 of the present invention.

The method for calculating the thickness of the subcutaneous fat 106 in the calculation part 120 will now be described. The relation between the amount of received light for measurement and the thickness of the subcutaneous fat 106 at contact forces of about 0.5 kg (about 1.75 kPa or greater when converted to pressure because the forming part 110 has a disk shape with the diameter of about 60 mm) and about 2.5 kg (8.75 kPa or greater when converted to pressure because the forming part 110 has a disk shape with the diameter of about 60 mm) is shown in FIG. 19. In FIG. 19, the black circle shows the relation between the amount of received light for measurement and the thickness of the subcutaneous fat 106 at about 1.75 kPa, and the white circle shows the relation between the amount of received light for measurement and the thickness of the subcutaneous fat 106 at about 8.75 kPa. Also, the solid line is a primary regression line for the pressure of about 1.75 kPa, and the dotted line is a primary regression line for the pressure of about 8.75 kPa.

Here, the thickness of subcutaneous fat in FIG. 19 refers to the thickness of subcutaneous fat when the subcutaneous fat is pushed by the forming part 110 and consequently crushed. However, the thickness of subcutaneous fat in FIG. 19 does not necessarily refer to the thickness of subcutaneous fat when the subcutaneous fat is pushed by the forming part 110 and consequently crushed. The thickness of subcutaneous fat may refer to the thickness of subcutaneous fat when the subcutaneous fat is not pushed by the forming part 110, namely the thickness of subcutaneous fat in a natural state. That is, if the relation between the amount of received light and the thickness of subcutaneous fat in a natural state is determined in advance, the thickness of the subcutaneous fat remaining in a natural state can be determined from the amount of received light. In addition, in Embodiments other than Embodiment 7, the thickness of subcutaneous fat refers to the thickness of subcutaneous fat when the subcutaneous fat is pushed by the forming part and consequently crushed, but the thickness of subcutaneous fat in a natural state may be shown as the thickness of subcutaneous fat by determining in advance the relation between the thickness of subcutaneous fat in a natural state and the amount of received light. Thus, the thickness of subcutaneous fat in Embodiment 7 and in Embodiments other than Embodiment 7 refers to the thickness of subcutaneous fat when the subcutaneous fat is pushed by the forming part and consequently crushed, but may refer to the thickness of subcutaneous fat in a natural state without being limited thereto.

As apparent from the figure, the line showing the relation between the amount of received light for measurement and the thickness of the subcutaneous fat 106 varies depending on the difference in pressure applied to the surface of the organism. Thus, a plurality of primary regression lines showing the relation between the amount of received light for measurement and the thickness of subcutaneous fat are determined in advance for a plurality of cases with different pressures applied to the surface of the organism, a primary regression line appropriate to the value of pressure measured in the pressure measuring part 115 is selected from the plurality of primary regression lines, and the selected primary regression line and the measured amount of received light for measurement are used, whereby the thickness of subcutaneous fat can be measured with high reproducibility and accuracy.

However, influences of variations in scattering and absorption in the skin 105 are included in the amount of received light for measurement as error factors. The amount of received light for correction is used for correcting the influences of the skin 105.

Figure 20:
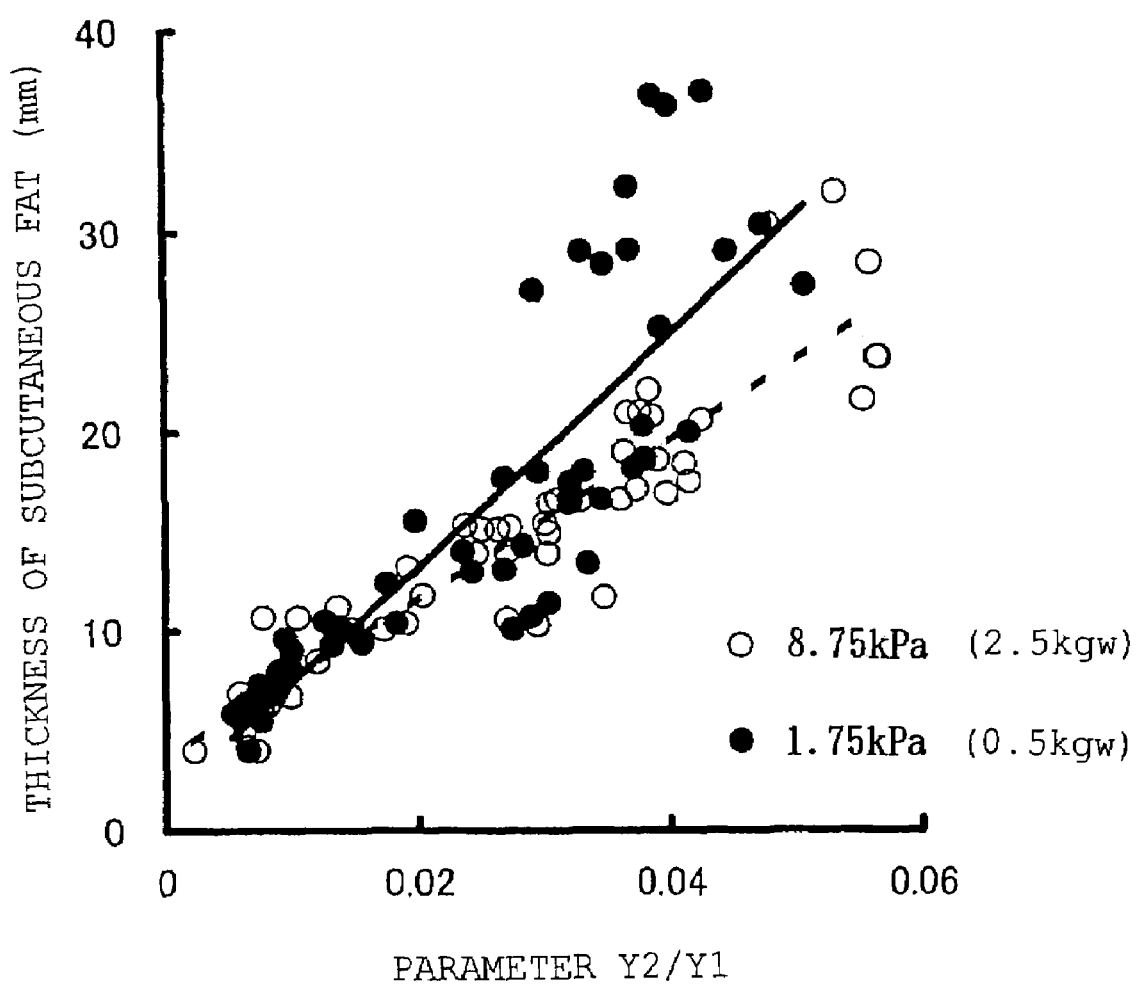
FIG. 20 shows a graph showing a relation between a parameter Y2/Y1 and the thickness of subcutaneous fat determined by the apparatus of measuring the thickness of subcutaneous fat using light in Embodiment 7 of the present invention.

The relation between a parameter Y2/Y1 with the amount of received light for measurement (amount of received light in the second distance Y2) divided by the amount of received light for correction (amount of received light in the first distance Y1) and the thickness of the subcutaneous fat 106 is shown in FIG. 20. In FIG. 20, the black circle shows the relation between Y2/Y1 and the thickness of the subcutaneous fat 106 at about 1.75 kPa, and the white circle shows the relation between Y2/Y1 and the thickness of the subcutaneous fat 106 at about 8.75 kPa. Also, the solid line is a primary regression line for the pressure of about 1.75 kPa, and the dotted line is a primary regression line for the pressure of about 8.75 kPa.

When compared with FIG. 19, variations are apparently alleviated, and it can be thus understood that the amount of received light for correction brings about a certain effect of correction. Also, as in the case of FIG. 19, the line showing the relation between Y2/Y1 and the thickness of the subcutaneous fat 106 varies depending on the difference in pressure. Thus, as in the case of using only the amount of received light for measurement, a plurality of primary regression lines each showing the correlation between Y2/Y1 and the thickness of subcutaneous fat are determined in advance for a plurality of cases of different pressures applied to the surface of the organism, a primary regression line appropriate to the value of pressure measured in the pressure measuring part 115 is selected from the plurality of primary regression lines, and by using the selected primary regression line and the Y2/Y1 influences of the skin 105 and influences of pressure applied to the surface of the organism can be corrected, thus making it possible to measure the thickness of subcutaneous fat with higher reproducibility and accuracy.

Figure 17:
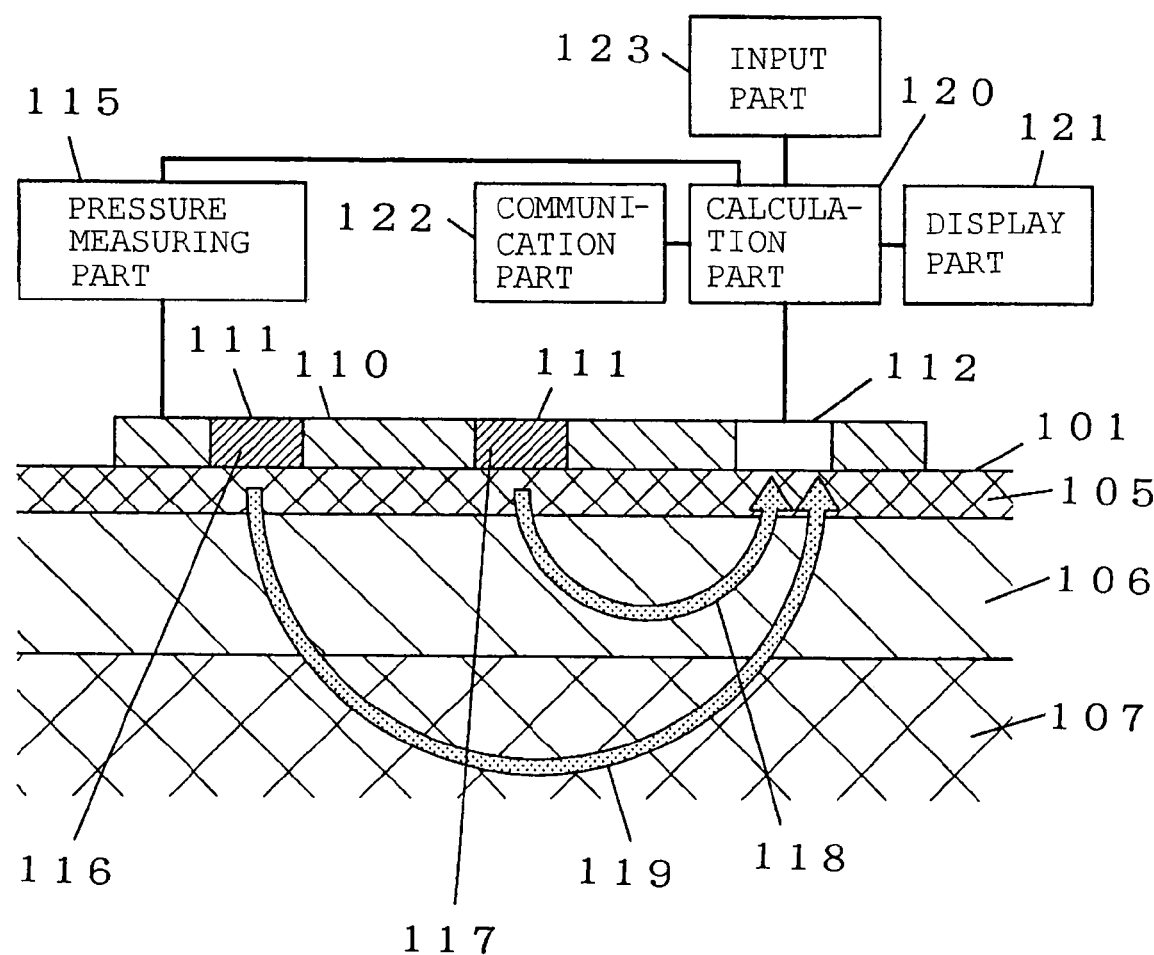
FIG. 17 is a block diagram of the apparatus of measuring the thickness of subcutaneous fat using light in which a light source part is different in configuration from a light receiving part in Embodiment 7 of the present invention.
Figure 18:
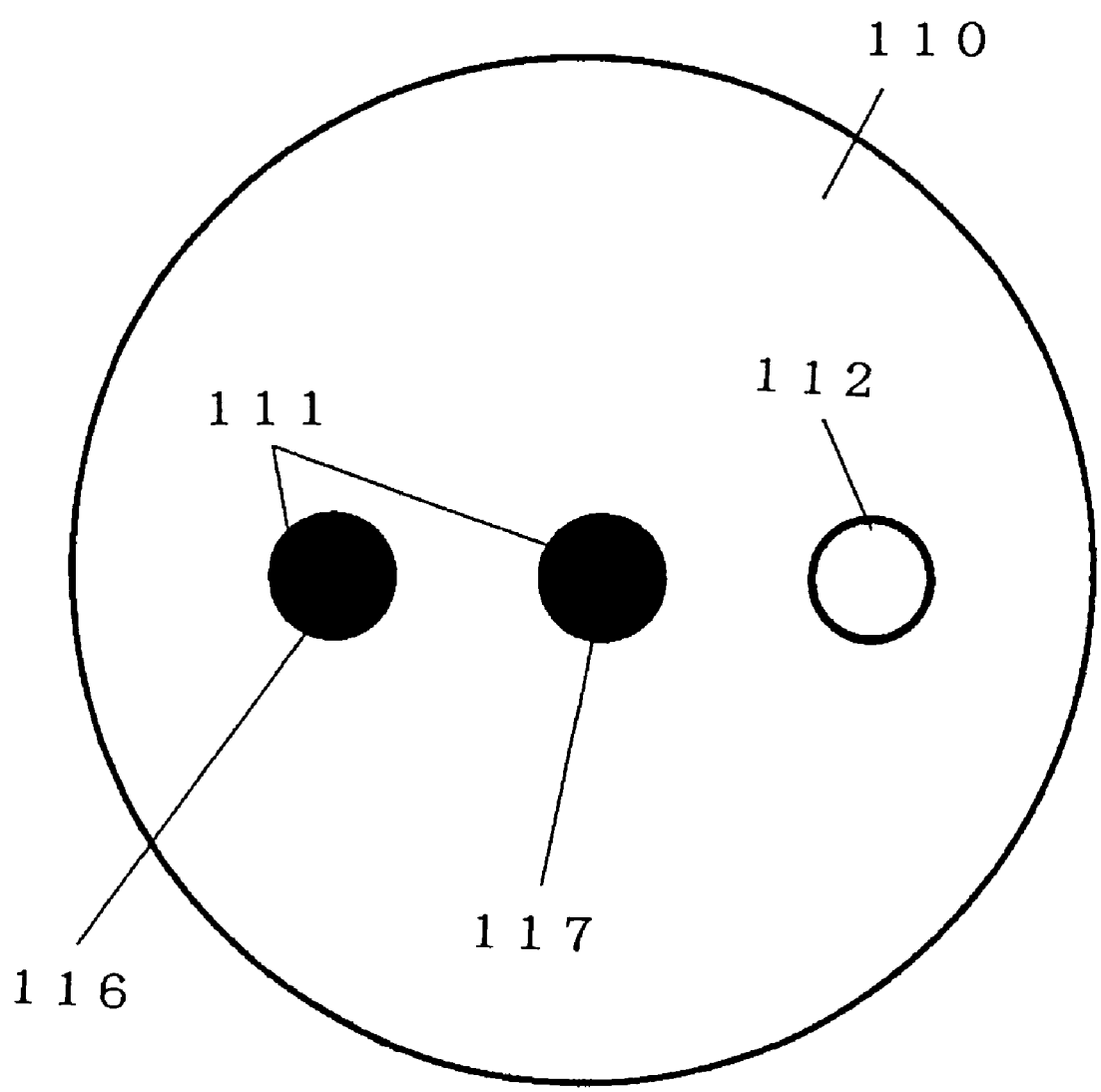
FIG. 18 is a top view of the forming part of the apparatus of measuring the thickness of subcutaneous fat using light in Embodiment 7 of the present invention, seen from the side on which it contacts the surface of the organism.

Here, the light source part is constituted by one light source 111, and the light receiving part 112 is constituted by the measuring light receiving element 113 and the correcting light receiving element 114, but as shown in the block diagram of FIG. 17 and the top view of the forming part 110 of FIG. 18, the light receiving part 112 maybe constituted by one light receiving element, and the light source part 111 may be constituted by a measuring light source element 116 and a correcting light source element 117. In this case, when the correcting light source element 117 is lit and the measuring light source element 116 is unlit, the amount of light (light from the correcting light source element) 118 received in the light receiving part 112 is the amount of received light for correction (amount of received light in the first distance Y1), and when the correcting light source element 117 is unlit and the measuring light source element 116 is lit, the amount of light (light from the measuring light source element) 119 received in the light receiving part 112 is the amount of received light for measurement (amount of received light in the second distance Y2).

EMBODIMENT 8

Figure 21:
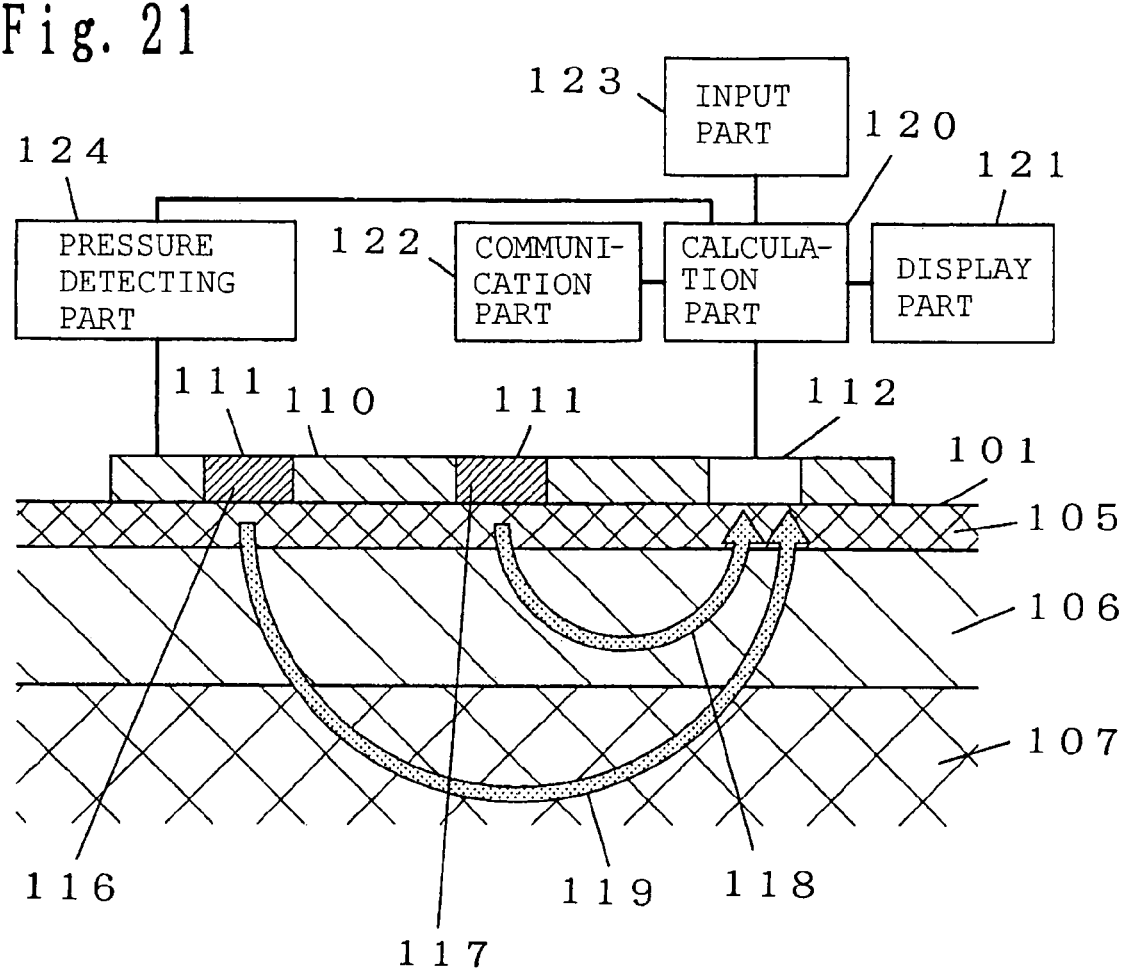
FIG. 21 is a block diagram of the apparatus of measuring the thickness of subcutaneous fat using light in Embodiment 8 of the present invention.

FIG. 21 is a block diagram of the apparatus of measuring the thickness of subcutaneous fat using light in Embodiment 8 of the present invention. It differs from the apparatus of measuring the thickness of subcutaneous fat using light in Embodiment 7 shown in FIG. 17 in that a pressure detecting part 124 detecting that the pressure applied to the surface of the organism 101 by the forming part 110 reaches a level equal to or greater than a predefined value is connected to the forming part 110 in place of the pressure measuring part. Other aspects of configuration are same as those of the apparatus of measuring the thickness of subcutaneous fat using light in Embodiment 7, and therefore descriptions thereof are not presented here.

If the pressure applied to the forming part 110 is increased while the forming part 110 is contacted against the surface of the organism, the thickness of the subcutaneous fat 106 is compressed and its thickness is reduced, but the thickness converges at a certain value. When the pressure at which the thickness of subcutaneous fat converges is defined as the predefined value, by applying a pressure equal to or greater than the predefined value to the surface of the organism 101, measurements can be carried out while the thickness of the subcutaneous fat 106 is kept stable. Also, the subcutaneous fat 106 is compressed and thereby its thickness is reduced, whereby individual differences due to variations in the amount of blood in the subcutaneous fat 106 are reduced. If the predefined value of contact force is about 2 kg or greater (about 7 kPa or greater when converted to pressure because the forming part 110 has a disk shape with the diameter of about 60 mm), the thickness of the subcutaneous fat 106 is advantageously stabilized. In this embodiment, the predefined value of pressure is about 8.75 kPa.

The procedure of measurement will now be described. As a first operation, the forming part 110 is contacted against the surface of the organism 101 while the light source 111 is unlit.

As a second operation, if the amount of light received in the light receiving part 112 is 100 pW or smaller, and a pressure equal to or greater than 8.75 kPa is detected in the pressure detecting part 124, the light source element 117 is lit up when it is ensured that the entire light receiving part 112 contacts the surface of the organism and the forming part 110 is contacted against the surface of the organism with a sufficient pressure, and in this state, a signal for start of measurement is inputted from the communication part 122 or input part 123.

As a third operation, the received amount of light 118 propagating from the correcting light source element 117 through the inside of the organism and arriving at the light receiving part 112, namely the amount of received light for correction (amount of received light in the first distance Y1) is measured.

Then, as a fourth operation, the received amount of light 119 propagating from the measuring light source element 116 through the inside of the organism and arriving at the light receiving part 112, namely the amount of received light for measurement (amount of received light in the second distance Y2) while the correcting light source element 117 is unlit and the measuring light source element 116 is lit.

Figure 22:
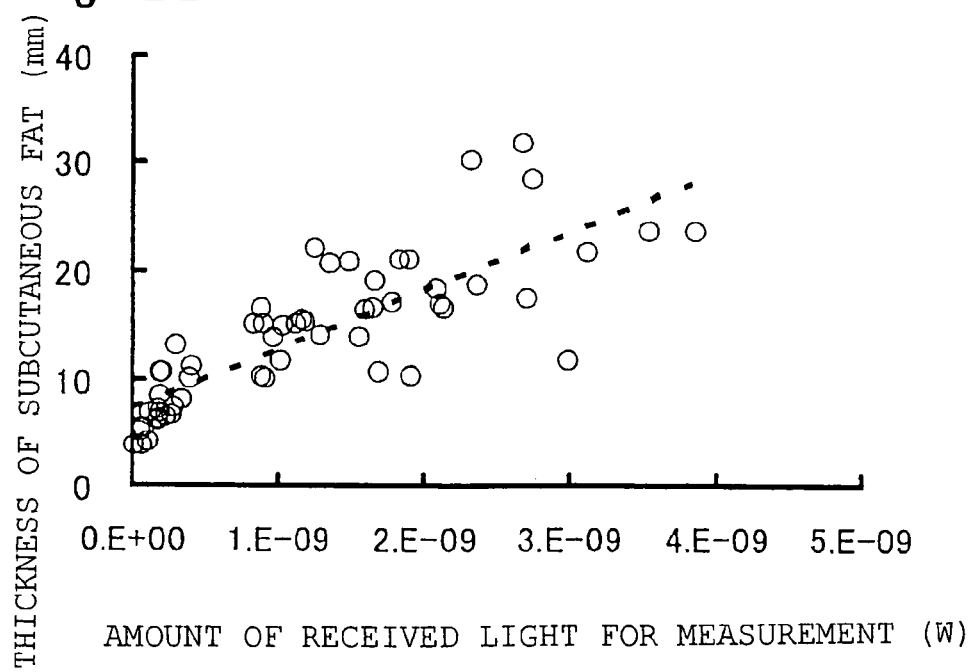
FIG. 22 shows a graph showing a relation between the amount of received light for measurement and the thickness of subcutaneous fat determined by the apparatus of measuring the thickness of subcutaneous fat using light in Embodiment 8 of the present invention.

How the thickness of the subcutaneous fat 106 is calculated in the calculation part 120 will now be described. The relation between the amount of received light for measurement and the thickness of the subcutaneous fat 106 is shown in FIG. 22. In FIG. 22, the white circle shows the relation between the amount of received light for measurement and the thickness of the subcutaneous fat 106, and the dotted line is its primary regression line. Thus, by using a relational expression of this primary regression line and the measured amount of received light for measurement, the thickness of subcutaneous fat can be determined. According to this measurement method, measurements are carried out while the thickness of the subcutaneous fat 106 is kept stable, thus making it possible to measure the thickness of subcutaneous fat with high reproducibility and accuracy.

Figure 23:
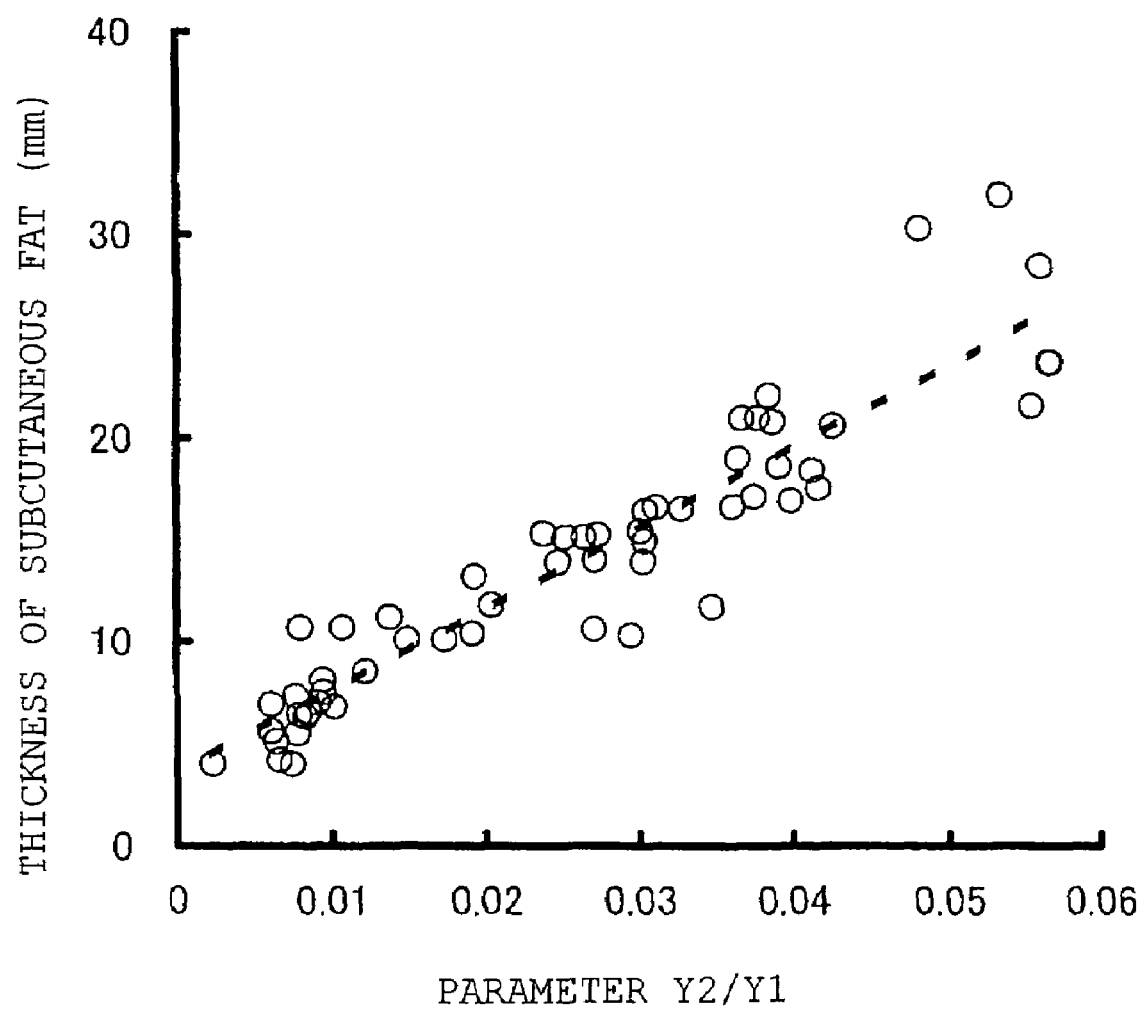
FIG. 23 shows a graph showing a relation between the parameter Y2/Y1 and the thickness of subcutaneous fat determined by the apparatus of measuring the thickness of subcutaneous fat using light in Embodiment 8 of the present invention.

In addition, the correction of influences of the skin 105 will be described. The relation between a parameter of Y2/Y1 with the amount of received light for measurement (amount of received light in the second distance Y2) divided by the amount of received light for correction (amount of received light in the first distance Y1) and the thickness of the subcutaneous fat 106 is shown in FIG. 23. In FIG. 23, the white circle shows the relation between the Y2/Y1 and the thickness of the subcutaneous fat 106, and the dotted line is its primary regression line. Thus, by using a relational expression of this primary regression line and the calculated parameter Y2/Y1, the thickness of subcutaneous fat can be determined. According to this measurement method, influences of the skin 105 can be corrected, thus making it possible to measure the thickness of subcutaneous fat with higher reproducibility and accuracy.

EMBODIMENT 9

Figure 24:
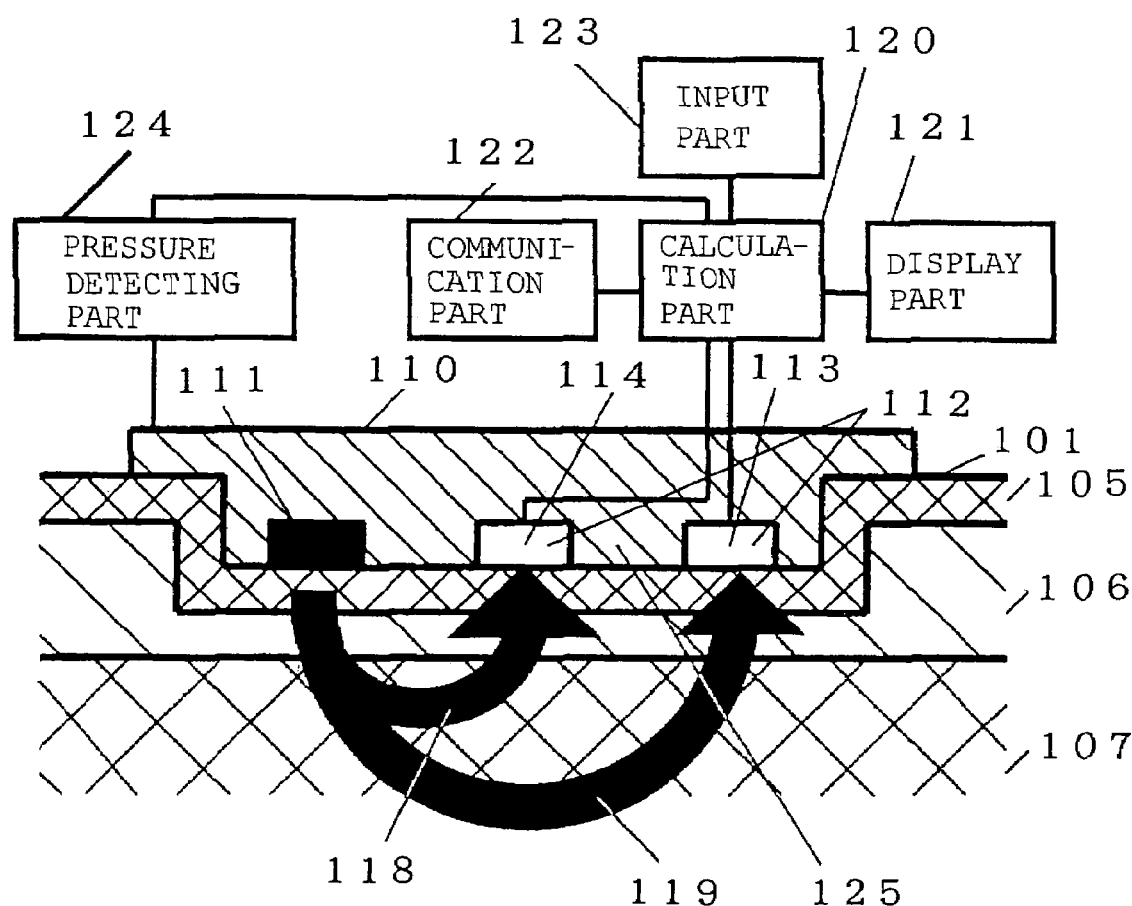
FIG. 24 shows a block diagram of the apparatus of measuring the thickness of subcutaneous fat using light in Embodiment 9 of the present invention.
Figure 25:
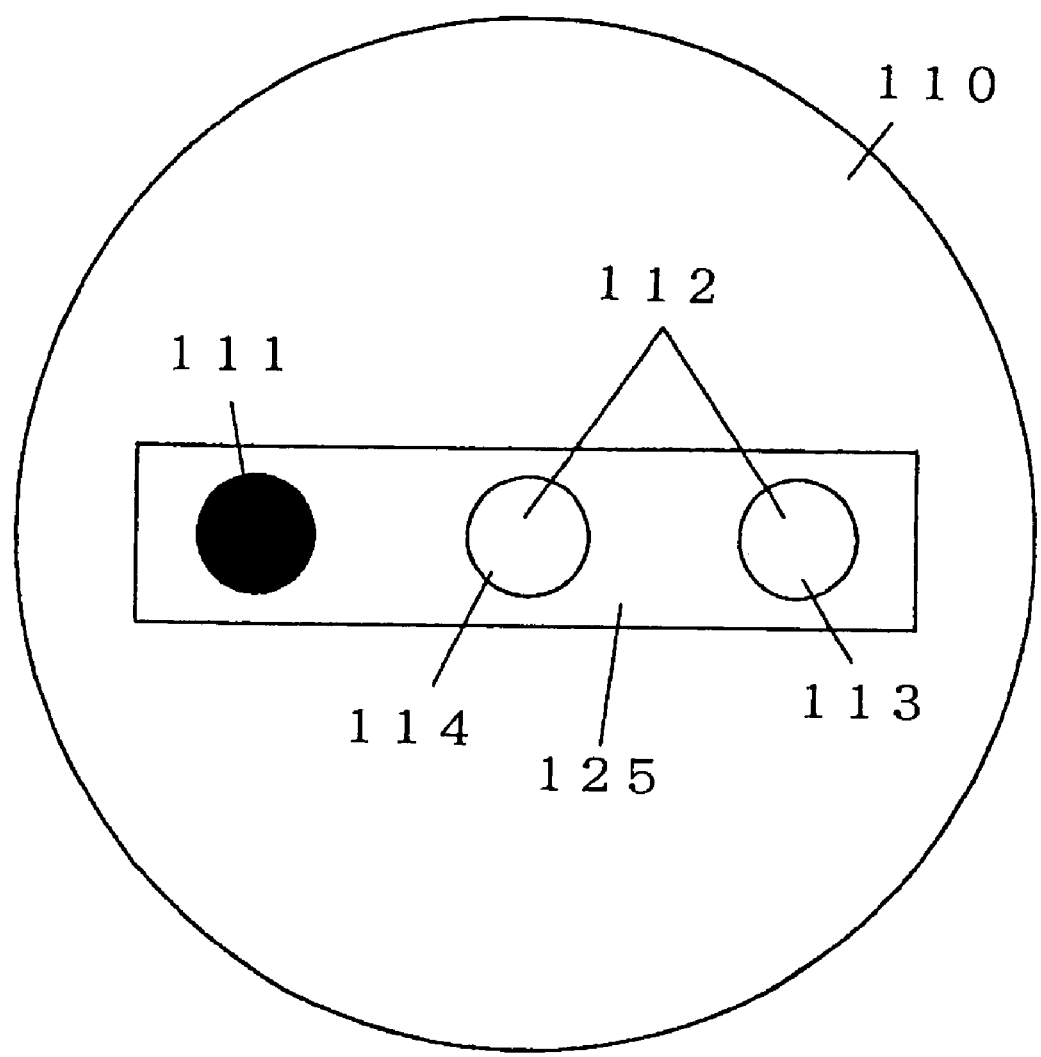
FIG. 25 is a top view of the forming part of the apparatus of measuring the thickness of subcutaneous fat using light in Embodiment 9 of the present invention, seen from the side on which it contacts the surface of the organism.

FIG. 24 is a block diagram of the apparatus of measuring the thickness of subcutaneous fat using light in Embodiment 9 of the present invention, and FIG. 25 is a top view of a forming part 110 of the apparatus of measuring the thickness of subcutaneous fat using light, seen from the side on which the forming part 110 contacts the surface of the organism 101. Aspects identical in configuration to those of Embodiment 7 or 8 are not described. A protrusion part 125 that is about 5 mm wide, 52.5 mm long and 5 mm high is placed at almost the center of the forming part 110, and the light source 111 and the light receiving part 112 are placed in the protrusion part 125.

Figure 27:
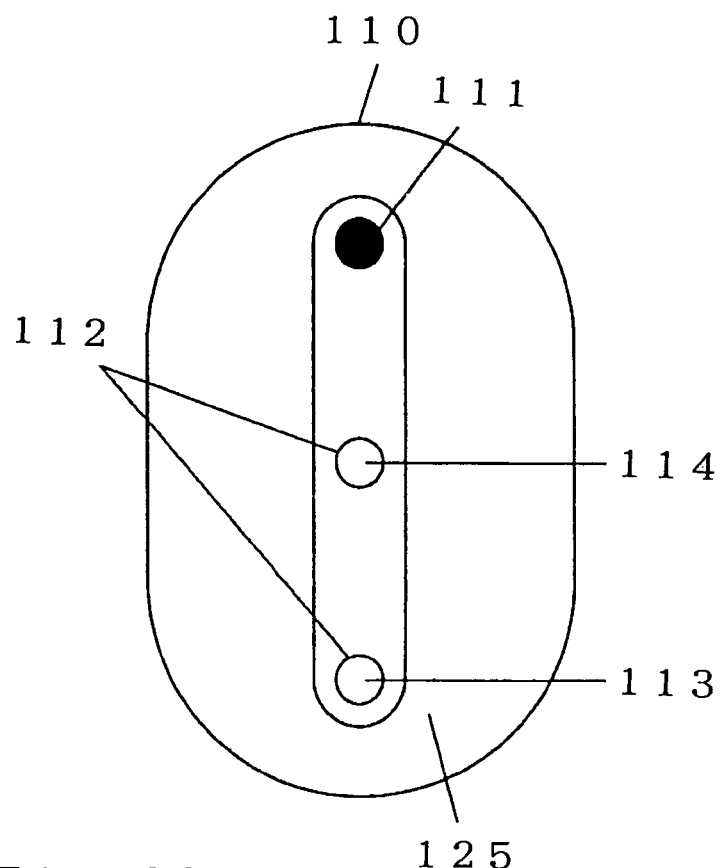
FIG. 27(a) is a top view of the forming part of the apparatus of measuring the thickness of subcutaneous fat using light in which the forming part is different in shape from the protrusion part in, Embodiment 9 of the present invention, seen from the side on which it contacts the surface of the organism.
FIG. 27(b) is a side view of the forming part of the apparatus of measuring the thickness of subcutaneous fat using light in which the forming part is different in shape from the protrusion part in Embodiment 9 of the present invention, seen from the side on which it contacts the surface of the organism.
Figure 27:
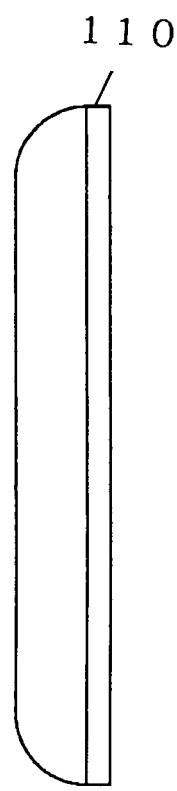

Furthermore, if the protrusion part 125 and the forming part 110 are shaped so that the corners of the protrusion part 125 are not sharp-pointed as shown in the top view of FIG. 26(a) and the side view of FIG. 26(b), a situation in which the organism is pained can advantageously be eliminated. That is, in FIGS. 26(a) and 26(b), a taper is attached so that the corners of the protrusion part 125 are not sharp-pointed. Also, the protrusion part 125 may be formed so that it has a curved face over the entire forming part 110 as shown in the top view of FIG. 27(a) and the side view of FIG. 27(b).

The face on which the protrusion part 125 of the forming part 110 is provided is contacted against the surface of the organism 101, whereby the surface of the organism 101 is locally pushed by the forming part 110 and the protrusion part 125 with stability to reduce the amount of blood in the subcutaneous fat 106 just below the protrusion part 125. Since the area of the pushed surface is small compared to the case where it is pushed only by the forming part 110, the amount of blood in the subcutaneous fat 106 just below the protrusion part 125 further decreases, and thus individual differences in variations associated with the amount of blood are further reduced.

Also, of light received in the receiving part 112, components of light that have propagated through areas other than the area just below the protrusion part 125 in the organism are more significantly attenuated than those that have propagated through the area just below the protrusion part 125 because they have propagated through areas having larger amount of blood than the area just below the protrusion part 125. Therefore, the proportion of components of light that have propagated through the subcutaneous fat 106 just below the protrusion part 125 in the amount of received light to be measured increases, thus making it possible to measure the thickness of subcutaneous fat more locally.

The procedure of measurement will now be described. As a first operation, the forming part 110 is contacted against the surface of the organism 101 while the light source 111 is unlit.

As a second operation, if the amount of light received in the light receiving part 112 is about 100 pW or smaller, and a pressure equal to or greater than about 8.75 kPa is detected in the pressure detecting part 124, the light source 111 is lit up when it is ensured that the entire light receiving part 112 contacts the surface of the organism and the forming part 110 is contacted against the surface of the organism with a sufficient pressure, and in this state, a signal for start of measurement is inputted from the communication part 122 or input part 123.

As a third operation, the amount of received light for correction (amount of received light in the first distance Y1) is determined by measuring light 118 arriving at the correcting light receiving element 114, and the amount of received light for measurement (amount of received light in the second distance Y2) is determined by measuring light 119 arriving at the measuring light receiving element 113.

Figure 28:
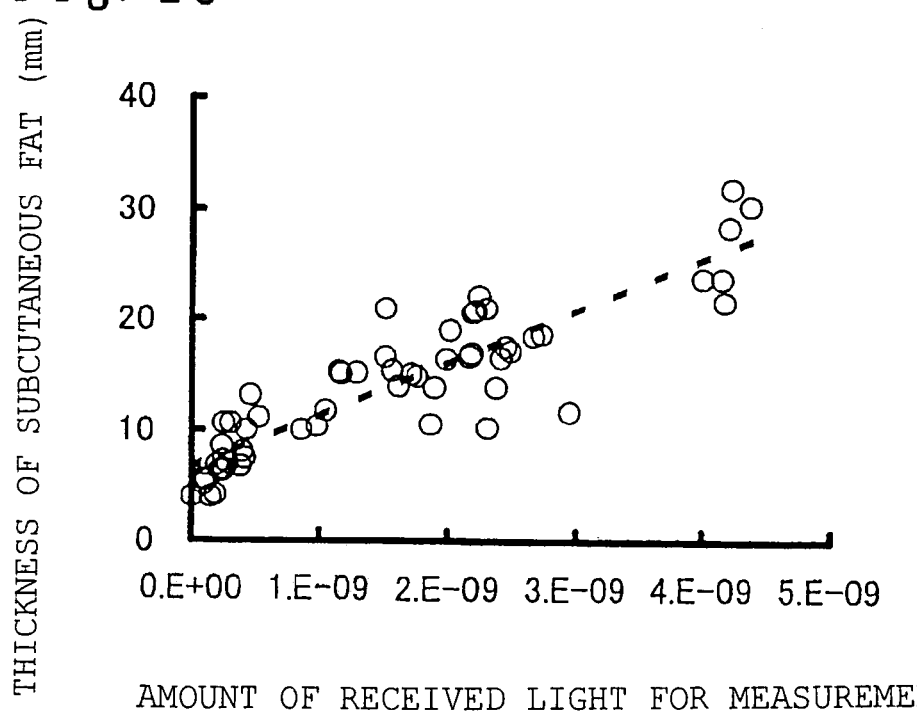
FIG. 28 shows a graph showing a relation between the amount of received light for measurement and the thickness of subcutaneous fat determined by the apparatus of measuring the thickness of subcutaneous fat using light in Embodiment 9 of the present invention.

How the thickness of the subcutaneous fat 106 is calculated in the calculation part 120 will now be described. The relation between the amount of received light for measurement and the thickness of the subcutaneous fat 106 is shown in FIG. 28. In FIG. 28, the white circle shows the relation between the amount of received light for measurement and the thickness of the subcutaneous fat 106, and the dotted line is its primary regression line. Thus, by using a relational expression of this primary regression line and the measured amount of received light for measurement, the thickness of subcutaneous fat can be determined. According to this measurement method, measurements are carried out while the thickness of the subcutaneous fat 106 is kept stable, thus making it possible to measure the thickness of subcutaneous fat with high reproducibility and accuracy.

Figure 29:
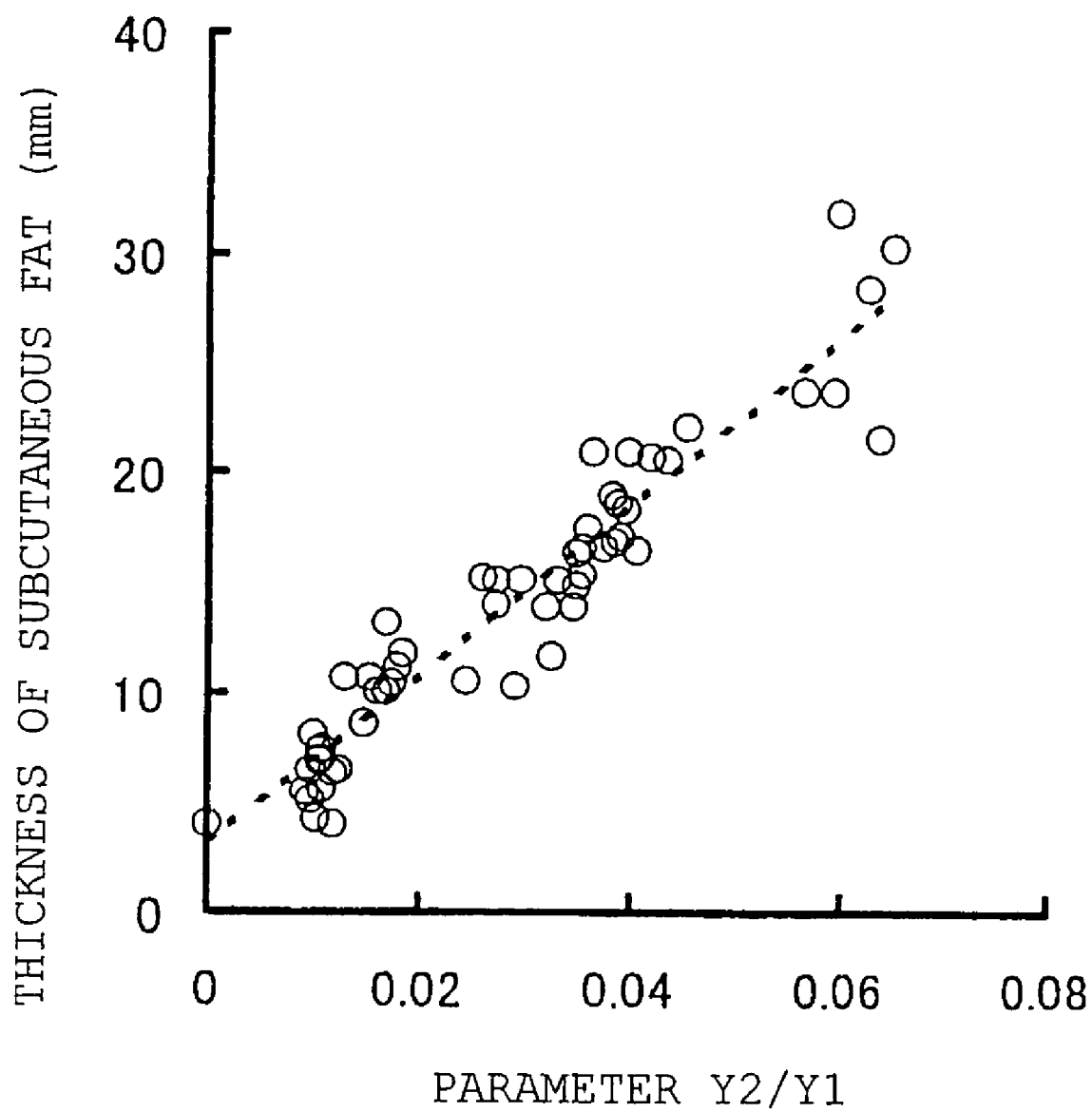
FIG. 29 shows a graph showing a relation between the parameter Y2/Y1 and the thickness of subcutaneous fat determined by the apparatus of measuring the thickness of subcutaneous fat using light in Embodiment 9 of the present invention.

In addition, the correction of influences of the skin 105 will be described. The relation between a parameter of Y2/Y1 with the amount of received light for measurement (amount of received light in the second distance Y2) divided by the amount of received light for correction (amount of received light in the first distance Y1) and the thickness of the subcutaneous fat 106 is shown in FIG. 29. In FIG. 29, the white circle shows the relation between the Y2/Y1 and the thickness of the subcutaneous fat 106, and the dotted line is its primary regression line. Thus, by using a relational expression of this primary regression line and the calculated parameter Y2/Y1, the thickness of subcutaneous fat can be determined. According to this measurement method, influences of the skin 105 can be corrected, thus making it possible to measure the thickness of subcutaneous fat with higher reproducibility and accuracy.

The method of measuring the thickness of subcutaneous fat using light in one embodiment of the present invention comprising:
  a first step of applying a pressure to the surface of an organism;
  a second step of detecting that the pressure reaches a predetermined value;
  a third step of irradiating the organism with light; and
  a fourth step of receiving light propagating through the inside of the organism and outgoing from the surface of the organism,
  and further comprising a fifth step of calculating the thickness of subcutaneous fat of the organism based on the amount of light received in the fourth step at a time when a predetermined amount of time passes after it is detected that the pressure reaches the predetermined value.

As the pressure applied to the surface of the organism increases, the thickness of subcutaneous fat decreases, but the thickness converges at a certain value. The pressure at which the thickness of subcutaneous fat converges is defined as the predefined value, and the thickness of subcutaneous fat is stabilized by applying a pressure equal to or greater than the predefined value to the surface of the organism. Also, just after the pressure is applied, deformation of the subcutaneous fat and the like is in a transient state, since the resistance occurs with which the blood in the pressurized site flows through vessels and the like before it moves to a non-pressurized site. Hence, the thickness of subcutaneous fat is calculated from the amount of received light in the fourth step acquired at a time when a predefined amount of time passes after a pressure equal to or greater than a predefined value is applied, so that the thickness of subcutaneous fat is stabilized, and therefore the thickness of subcutaneous fat can be measured with high reproducibility and accuracy.

Here, the predefined amount of time in the fifth step is preferably about 200 ms or greater.

The method of measuring the thickness of subcutaneous fat using light in one embodiment of the present invention comprising:
  a first step of applying a pressure to the surface of an organism;
  a second step of detecting that the pressure reaches a predetermined value;
  a third step of irradiating the organism with light; and
  a fourth step of receiving light propagating through the inside of the organism and outgoing from the surface of the organism,
  and further comprising a fifth step of monitoring variations in the amount of light received in the fourth step 4 when it is detected that the pressure reaches the predetermined value, and calculating the thickness of subcutaneous fat of the organism based on the amount of received light acquired at the time when the variations in received light are within a predetermined value.

As the pressure applied to the surface of the organism increases, the thickness of subcutaneous fat decreases, but the thickness converges at a certain value. When the pressure at which the thickness of subcutaneous fat converses is defined as the predefined value, the thickness of subcutaneous fat is stabilized by applying a pressure equal to or greater than the predefined value to the surface of the organism. Also, just after the pressure is applied, deformation of the subcutaneous fat and the like is in a transient state, since the resistance occurs with which the blood in the pressurized site flows through vessels and the like before it moves to a non-pressurized site. Hence, the thickness of subcutaneous fat is calculated from the amount of received light in the fourth step after the amount of received light is stably within a predefined value, so that the thickness of subcutaneous fat is stabilized, and therefore the thickness of subcutaneous fat can be measured with high reproducibility and accuracy.

Here, if the variation in the amount of received light is within about ±10%, the thickness of subcutaneous fat is advantageously stabilized.

Here, if the predefined value in the second step is about 7 kPa or greater, the thickness of subcutaneous fat is advantageously stabilized.

Also, if the central wavelength of light applied in the third step is in the range of from about 500 nm to 1000 nm, there are advantageously differences in absorption and scattering characteristics between tissues of skin, muscle and fat.

The apparatus of measuring the thickness of subcutaneous fat using light of one embodiment of the present invention is characterized by comprising:
  a pressure applying part applying a pressure to the surface of an organism;
  a pressure detecting part detecting that the pressure reaches a predetermined value;
  a light source part irradiating the organism with light; and
  a light receiving part receiving the light propagating through the inside of the organism and outgoing from the surface of the organism,
  the apparatus further comprising a calculation part calculating the thickness of subcutaneous fat of the organism based on the amount of light received on the light receiving part acquired at a time when a predetermined amount of time passes after it is detected that the pressure reaches the predetermined value.

As the pressure applied to the surface of the organism increases, the thickness of subcutaneous fat decreases, but the thickness converges at a certain value. When the pressure at which the thickness of subcutaneous fat converges is defined as the predefined value, the thickness of subcutaneous fat is stabilized by applying a pressure equal to or greater than the predefined value to the surface of the organism. Also, just after the pressure is applied, deformation of the subcutaneous fat and the like is in a transient state, since the resistance occurs with which the blood in the pressurized site flows through vessels and the like before it moves to a non-pressurized site. Hence, the thickness of subcutaneous fat is calculated from the amount of received light in the light receiving part acquired at a time when a predefined amount of time passes after a pressure equal to or greater than a predefined value is applied, so that the thickness of subcutaneous fat is stabilized, and therefore the thickness of subcutaneous fat can be measured with high reproducibility and accuracy.

Also, the apparatus of measuring the thickness of subcutaneous fat using light of one embodiment of the present invention comprising:

a pressure applying part applying a pressure to the surface of an organism;

a pressure detecting part detecting that the pressure reaches a predetermined value;

a light source part irradiating the organism with light; and a light receiving part receiving the light propagating through the inside of the organism and outgoing from the surface of the organism, the apparatus further comprising a calculation part monitoring variations in the amount of light received in the light receiving part when it is detected that the pressure reaches the predetermined value, and calculating the thickness of subcutaneous fat of the organism based on the amount of received light acquired at a time when the variations in the amount of received light are within a predetermined value.

As the pressure applied to the surface of the organism increases, the thickness of subcutaneous fat decreases, but the thickness converges at a certain value. When the pressure at which the thickness of subcutaneous fat converges is defined as the predefined value, the thickness of subcutaneous fat is stabilized by applying a pressure equal to or greater than the predefined value to the surface of the organism. Also, just after the pressure is applied, deformation of the subcutaneous fat and the like is in a transient state, since the resistance occurs with which the blood in the pressurized site flows through vessels and the like before it moves to a non-pressurized site. Hence, the thickness of subcutaneous fat is calculated from the amount of received light in the light receiving part acquired after the amount of received light is stably within a predefined value, so that the thickness of subcutaneous fat is stabilized, and therefore the thickness of subcutaneous fat can be measured with high reproducibility and accuracy.

Preferably, a generally planar face in contact with the surface of the organism at the pressurized portion ensures that an even pressure is applied on the surface of the organism to be measured.

Also, a plurality of light sources are preferably provided in the light source part. Also, a plurality of light receiving elements may be provided in the light receiving part.

Also, if there are a light source and a light receiving element provided so that the distance between the light source and the light receiving element is a first distance of about 15 mm to 30 mm, and a light source and a light receiving element provided so that the distance between the light source and the light receiving element is a second distance of about 35 mm to 80 mm, and the amount of received light in the light receiving element with the first distance equals Y1, and the amount of received light in the light receiving element with the second distance equals Y2, the thickness of subcutaneous fat of the organism is calculated using the ratio between Y2 and Y1 in the calculation part. From this way, influences of colors of skin can be eliminated, thus making it possible to measure the thickness of subcutaneous fat with higher reproducibility and accuracy.

The method of measuring the thickness of subcutaneous fat of the present invention and the apparatus for use in the method will be described in detail below using the drawings.

EMBODIMENT 10

Figure 30:
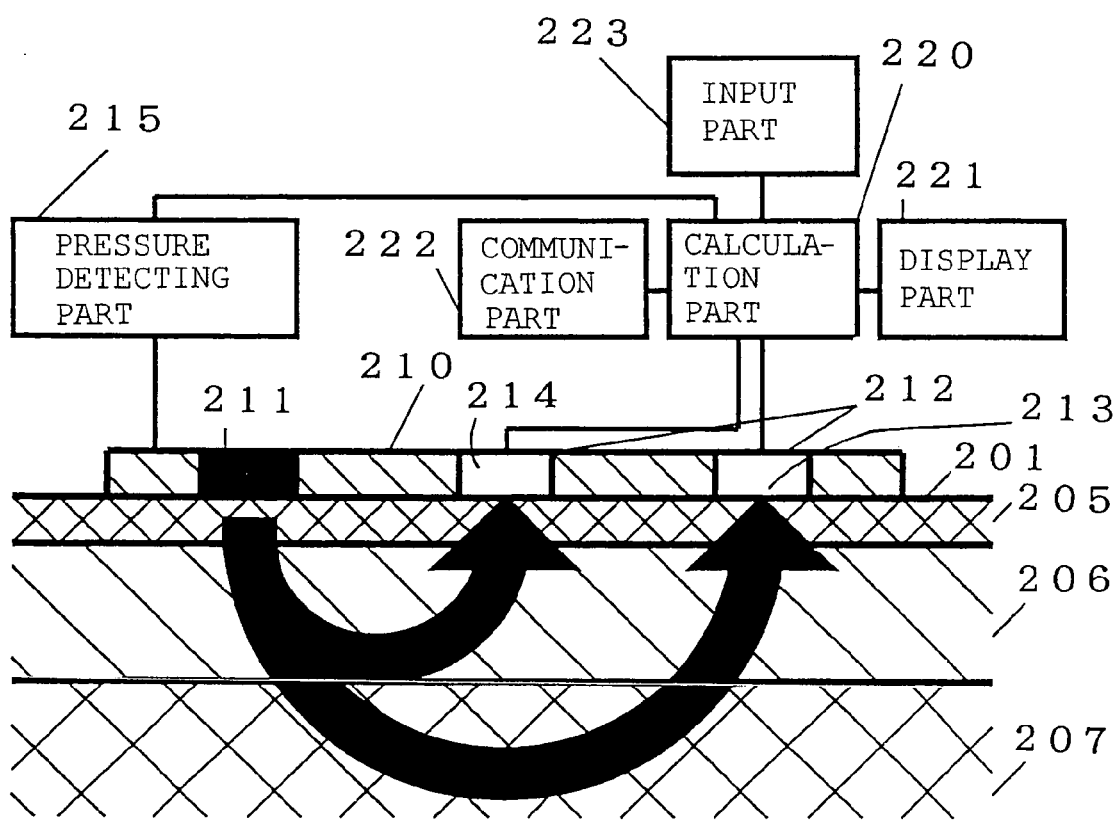
FIG. 30 is a block diagram of the apparatus of measuring the thickness of subcutaneous fat using light in Embodiments 10 and 11 of the present invention.
Figure 31:
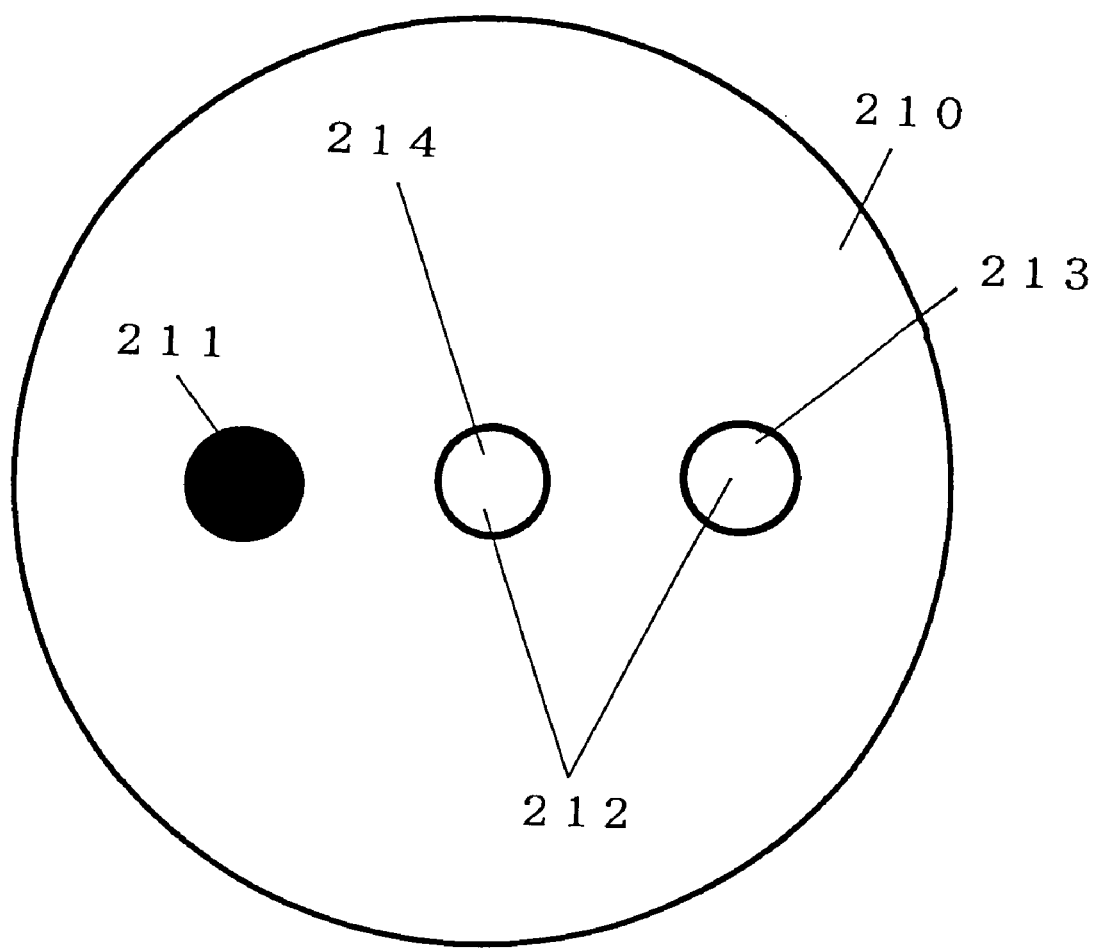
FIG. 31 is a top view of the forming part of the apparatus of measuring the thickness of subcutaneous fat using light in Embodiments 10 and 11 of the present invention, seen from the side on which it contacts the surface of the organism.

FIG. 30 is a block diagram of the apparatus of measuring the thickness of subcutaneous fat using light in Embodiment 10 of the present invention, and FIG. 31 is a top view of a forming part 210 being a pressure applying part of the apparatus of measuring the thickness of subcutaneous fat using light seen from the side on which the forming part 210 contacts the surface of an organism 201.

The forming part 210 forming the surface of the organism 201 into almost a flat shape is provided on the surface of the organism 201 constituted by three layers of a skin 205, a subcutaneous fat 206 and a muscle 207. The forming part 210 has a disk shape with the diameter of about 60 mm, and is made of black ABS. Furthermore, the material of the forming part 210 is not limited as long as it has a low degree of reflection of light from a light source part 211. The forming part 210 has each corner rounded to prevent a situation in which a sharp-pointed portion abuts against the surface of the organism. Furthermore, the forming part 210 may have an oval shape or a shape of a flat plate whose corner is chamfered that is about 40 mm long and 60 mm wide.

The light source part 211 and a light receiving part 212 are provided in the forming part 210. The light receiving part 212 is composed of a measuring light receiving element 213 (second light receiving element) and a correcting light receiving element 214. (first light receiving element). The distance between the measuring light receiving element 213 and the light source 211 is about 45 mm, and the distance between the correcting light receiving element 214 and the light source 211 is about 22.5 mm. The emission orifice of light emitted from the light source part 211 has a diameter of about 1.5 mmφ, and the incident orifice of light of the measuring light receiving element 213 and correcting light receiving element 214 has a diameter of about 1.5 mmφ. Furthermore, the distance between the measuring light receiving element 213 and the light source part 211 is preferably in the range of from about 35 mm to 80 mm (second distance), and the distance between the correcting light receiving element 214 and the light source 211 (first distance) is preferably in the range of from about 15 mm to 30 mm. When the light source 211 is lit up, an amount of received light for correction (Y1) is received in the correcting light receiving element 214, and an amount of received light for measurement (Y2) is received in the measuring light receiving element 213.

Figure 32:
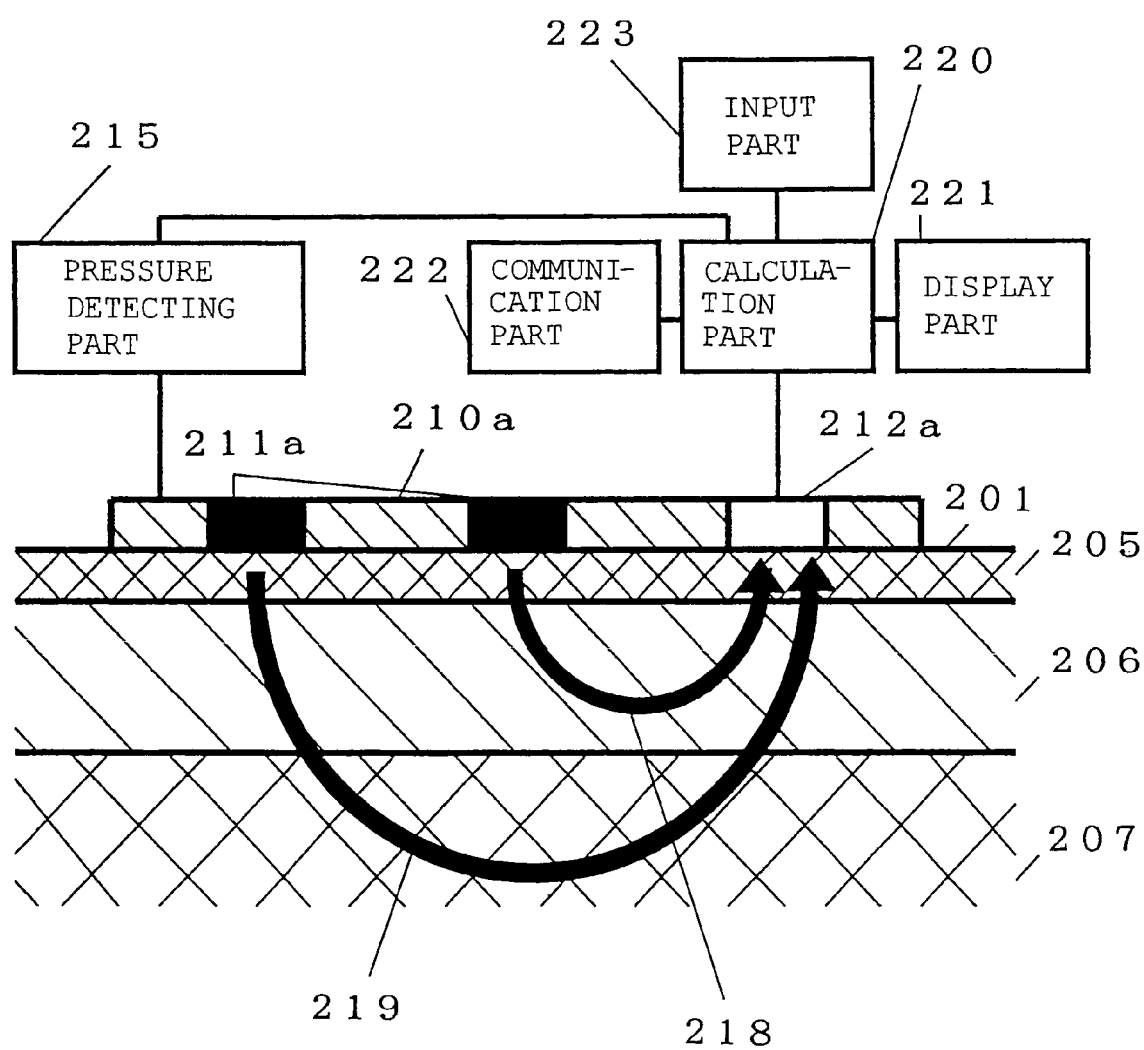
FIG. 32 is a block diagram of the apparatus of measuring the thickness of subcutaneous fat using light in which the light source part is different in configuration from the light receiving part in Embodiment 10 of the present invention.
Figure 33:
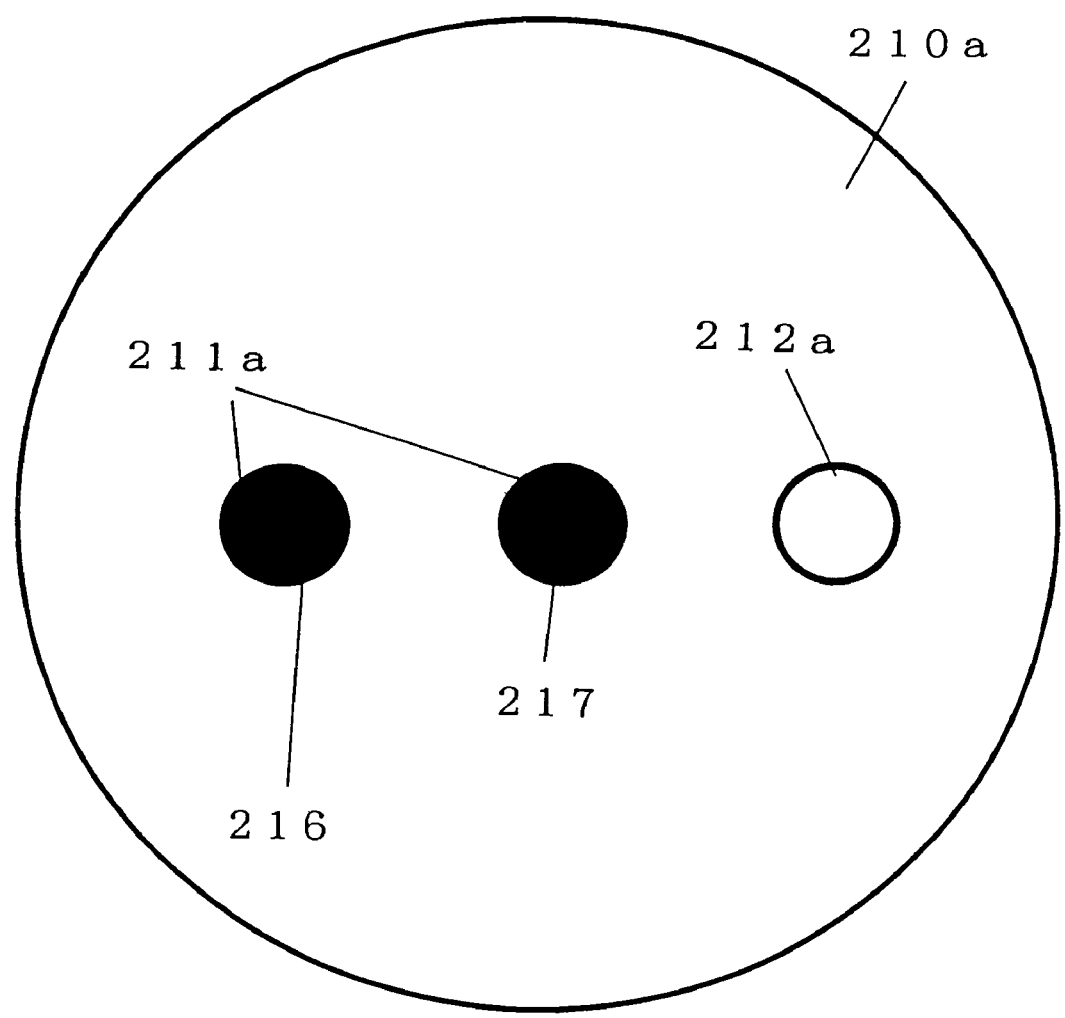
FIG. 33 is a top view of the forming part of the apparatus of measuring the thickness of subcutaneous fat using light in Embodiment 10 of the present invention, seen from the side on which it contacts the surface of the organism.

Here, the light source part is constituted by one light source 211, and the light receiving part 212 is constituted by the measuring light receiving element 213 and the correcting light receiving element 214, but instead thereof, the configuration shown in the block diagram of FIG. 32 and a forming part 210a of FIG. 33 may be used. Specifically, as shown in the block diagram of FIG. 32 and the top view of the forming part 210a of FIG. 33, a light receiving part 212a may be constituted by one light receiving element, and a light source part 211a may be constituted by a measuring light source element 216 and a correcting light source element 217. In this case, the amount of light 218 received in the light receiving part 212a is the amount of received light for correction (amount of received light in the first distance Y1) when the correcting light receiving element 217 is lit and the measuring light receiving element 216 is unlit, and the amount of light 219 received in the light receiving part 212 is the amount of received light for measurement (amount of received light in the second distance Y2) when the correcting light source element 217 is unlit and the measuring light source element 216 is lit.

Here, the light source part 211 uses a laser diode with the central wavelength about 785 nm as a light source element. Furthermore, it is preferable the light source element is a light source element such as a laser diode or LED with the central wavelength of about 500 nm to 1000 nm. In addition, if a light guide component such as optical fibers is used for guiding light from the light source element to the surface of the organism, heat generated in the light source element is advantageously prevented from being transferred to the surface of the organism. Furthermore, the same may hold true for the light source part 211a described with FIGS. 32 and 33.

The light receiving part 212 uses a photodiode as a light receiving element. Furthermore, the light receiving element may be a photoelectric conversion element such as CdS. Also, a light guide component such as optical fibers may be used for guiding light from the surface of the organism to the light receiving element. Furthermore, the same may hold true for the light receiving part 212a described with FIGS. 32 and 33.

In FIG. 30, a pressure detecting part 215 detecting that the pressure applied to the surface of the organism 201 by the forming part 210 reaches a predefined value is connected to the forming part 210. If the pressure applied to the forming part 210 is increased while the forming part 210 is contacted against the surface of the organism, the thickness of the subcutaneous fat 206 is compressed and its thickness is reduced as the pressure is increased, but the thickness converges at a certain value. If the pressure at which the thickness of subcutaneous fat converges is defined as the predefined value, measurements can be carried out while the thickness of the subcutaneous fat 206 is kept stable by applying a pressure equal to or greater than the predefined value to the surface of the organism 201. Also, the subcutaneous fat 206 is compressed and thereby its thickness is reduced, whereby individual differences due to variations in the amount of blood in the subcutaneous fat 206 are reduced.

Figure 34:
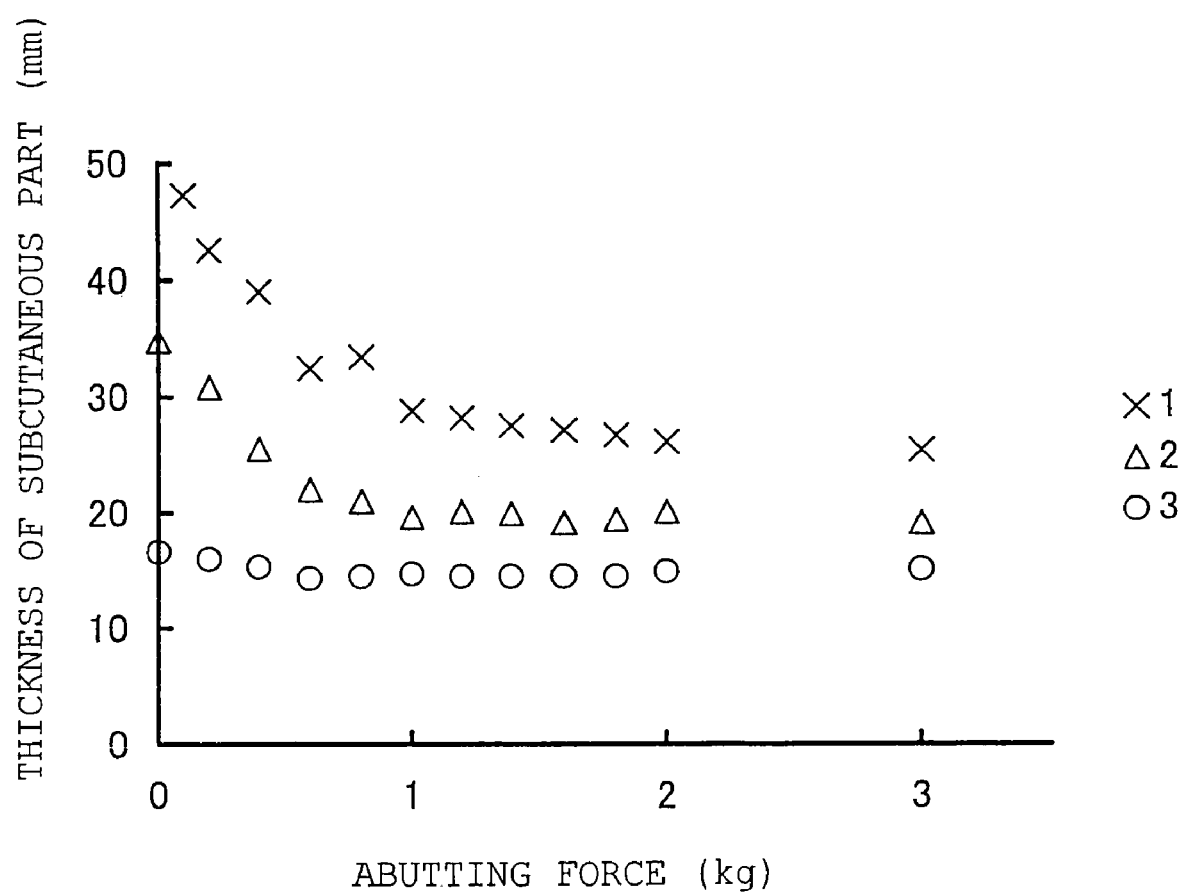
FIG. 34 shows one example of relation between the thickness of subcutaneous fat and a contact force in Embodiment 10 of the present invention.

FIG. 34 shows the relation between the contact force and the thickness of subcutaneous fat when a plate similar in shape to the forming part 210 is contacted against three different organisms. From FIG. 34, it can be said that if a predefined value of contact force is about 2 kg or greater, the thickness of the subcutaneous fat 206 is advantageously stabilized. Here, the area of the forming part 210 is about 28.26 cm$^2$, and therefore the predefined value of pressure is about 7 kPa in this embodiment.

Therefore, as long as a pressure equal to or greater than the predefined value is applied to the surface of the organism 201, the thickness of the subcutaneous fat 206 is kept stable even if there are some variations in pressure. Therefore, the thickness of subcutaneous fat can be measured simply and accurately only by abutting the forming part 210 against the surface of the organism by a human hand with a pressure equal to or greater than a predefined value without using a special measure for abutting the forming part 210 against the surface of the organism 201.

The calculation part 220 calculates the thickness of the subcutaneous fat 206 based on the amount of received light obtained in the light receiving part 212 after a predefined amount of time from a time when the pressure equal to or greater than a predefined value is detected in the pressure detecting part 215. That is, the amount of received light is not stabilized at the moment that the pressure reaches the predefined value because the blood in organic tissues undergoes resistances in blood vessels and the like, and the blood and the like are on the move while the thickness of subcutaneous fat still varies, and therefore the thickness of subcutaneous fat is calculated from the amount of received light acquired after a predefined amount of time during which variations in thickness of subcutaneous fat are eliminated. Here, the predefined amount of time is about 200 ms or greater. The thickness of the subcutaneous fat 206 calculated in the calculation part 220 is displayed on a display part 221, is transmitted through a communication part 222 to other apparatuses as data.

Also, by inputting data such as the height, the weight, the age, the sex and the site to be measured directly from an input part 223 or from other apparatus through the communication part 222, the percent of body fat correlative with the thickness of the subcutaneous fat 206 can be calculated in the calculation part 220 and displayed on the display part 221, and data can be transferred to other apparatuses by the communication part 222.

The procedure of measurement will now be described. As a first operation, the forming part 210 is contacted against the surface of the organism 201 while the light source 211 is unlit.

As a second operation, if the amount of light received in the light receiving part 212 is about 100 pW or smaller, and the value measured in the pressure measuring part 215 is about 7 kg or greater, the light source 211 is lit up when it is ensured that the entire light receiving part 212 contacts the surface of the organism and the forming part 210 is contacted against the surface of the organism with a pressure equal to or greater than a predefined value, and in this state, a signal for start of measurement is inputted from the communication part 222 or input part 223.

As a third operation, the amount of received light for correction (amount of received light in the first distance Y1) is determined by measuring light arriving at the correcting light receiving element 214 after about 200 ms, and the amount of received light for measurement (amount of received light in the second distance Y2) is determined by measuring light arriving at the measuring light receiving element 213.

Furthermore, the first, second and third operations are carried out in this order in the procedure described above, but the first, second and third operations may be carried out in any order. Also, the light source 1 is not lit when the first operation is carried out in the procedure described above, but the light source may be lit up before the first operation is carried out.

Figure 35:
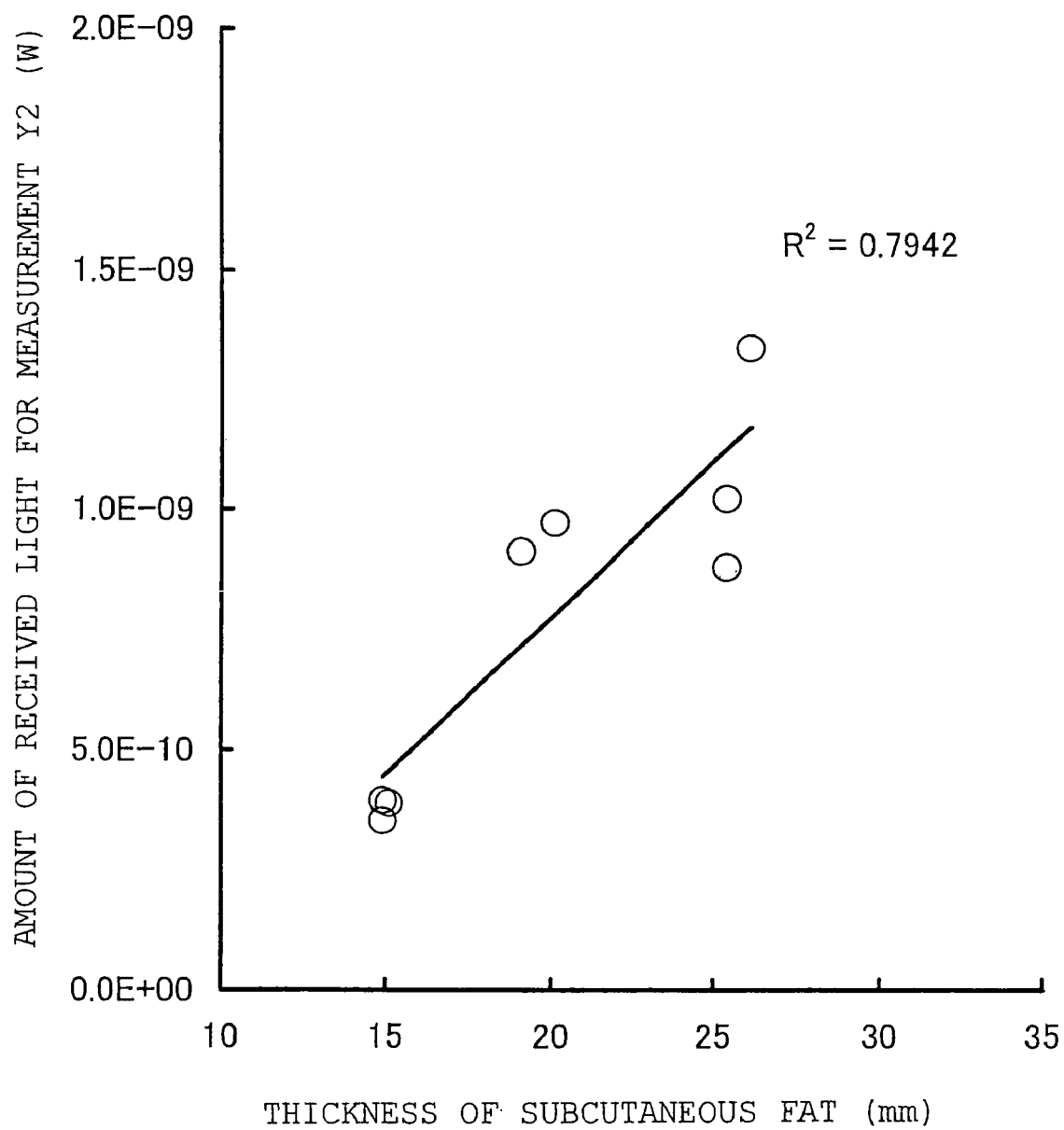
FIG. 35 shows a graph showing one example of relation between the amount of received light for measurement and the thickness of subcutaneous fat determined by the apparatus of measuring the thickness of subcutaneous fat using light in Embodiments 10 and 11 of the present invention.
Figure 36:
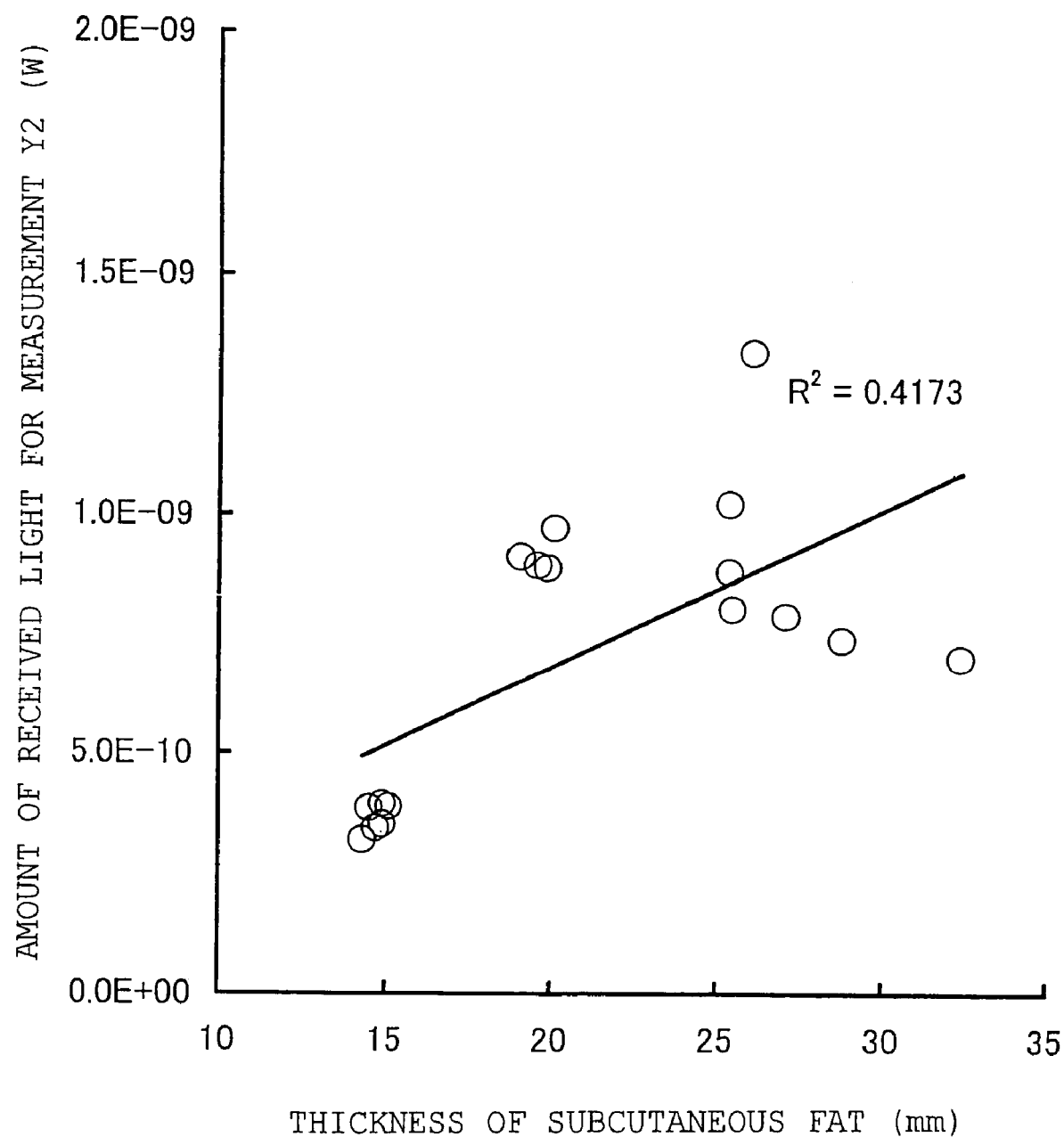
FIG. 36 shows a graph showing one example of relation between the amount of received light for measurement and the thickness of subcutaneous fat when the pressure is not controlled in Embodiment 10 of the present invention.

How the thickness of the subcutaneous fat 206 is calculated in the calculation part 220 will now be described. One example of relation between the amount of received light for measurement and the thickness of the subcutaneous fat 206 is shown in FIG. 35. A plurality of primary regression lines each showing the correlation between the amount of received light for measurement and the thickness of subcutaneous fat are determined in advance, and the primary regression lines and the amount of received light for measurement are used, whereby the thickness of subcutaneous fat can be measured with high reproducibility and accuracy, variations in pressure applied to the surface of the organism and variations in the amount of blood in the organism being alleviated. Here, one example of relation between the amount of received light for measurement and the thickness of subcutaneous fat when the pressure is not controlled is shown in FIG. 36. The example of FIG. 36 has significant variations and is inferior in correlation to the example of FIG. 35 in which the pressure is controlled.

However, influences of colors of the skin 205 and the like are included in the amount of received light for measurement Y2 as error factors. The amount of received light for correction Y1 is used for correcting the influences of colors of the skin 205 and the like.

Figure 37:
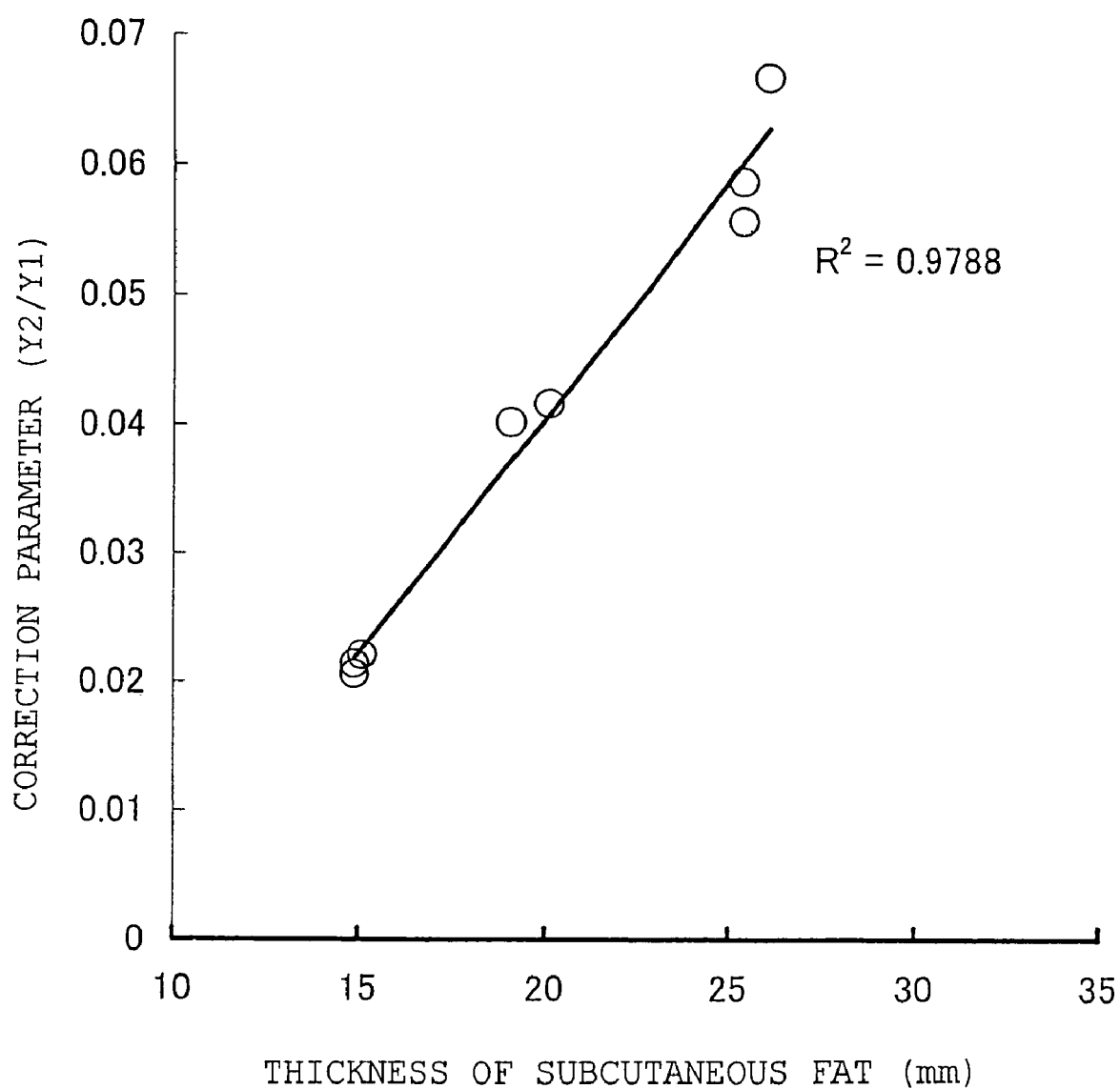
FIG. 37 is a graph showing a relation between the parameter Y2/Y1 and the thickness of subcutaneous fat determined by the apparatus of measuring the thickness of subcutaneous fat using light in Embodiments 10 and 11 of the present invention.
Figure 38:
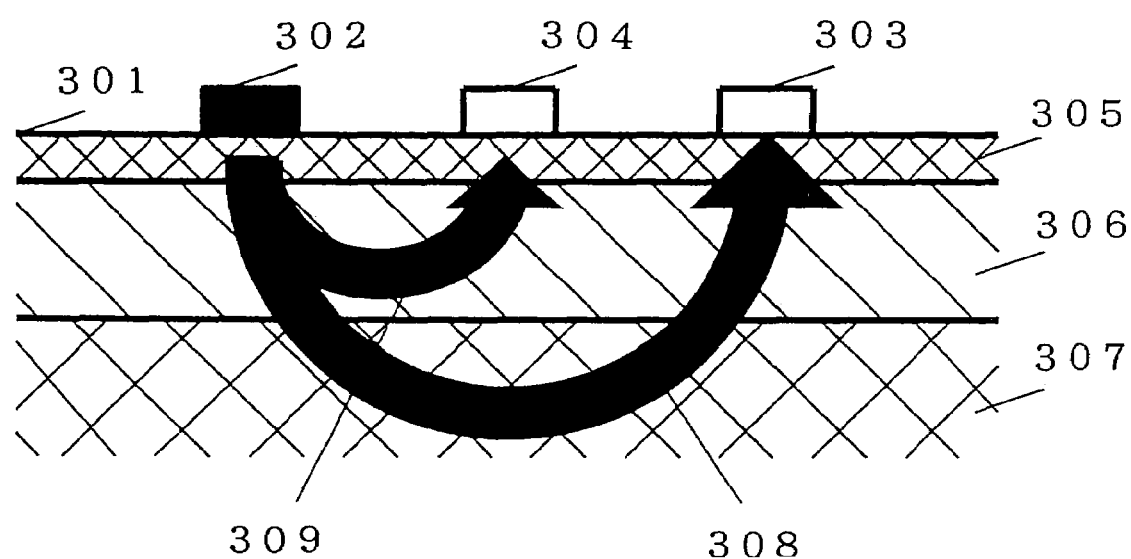
FIG. 38 is a block diagram of the conventional subcutaneous fat thickness measuring apparatus.
Figure 39:
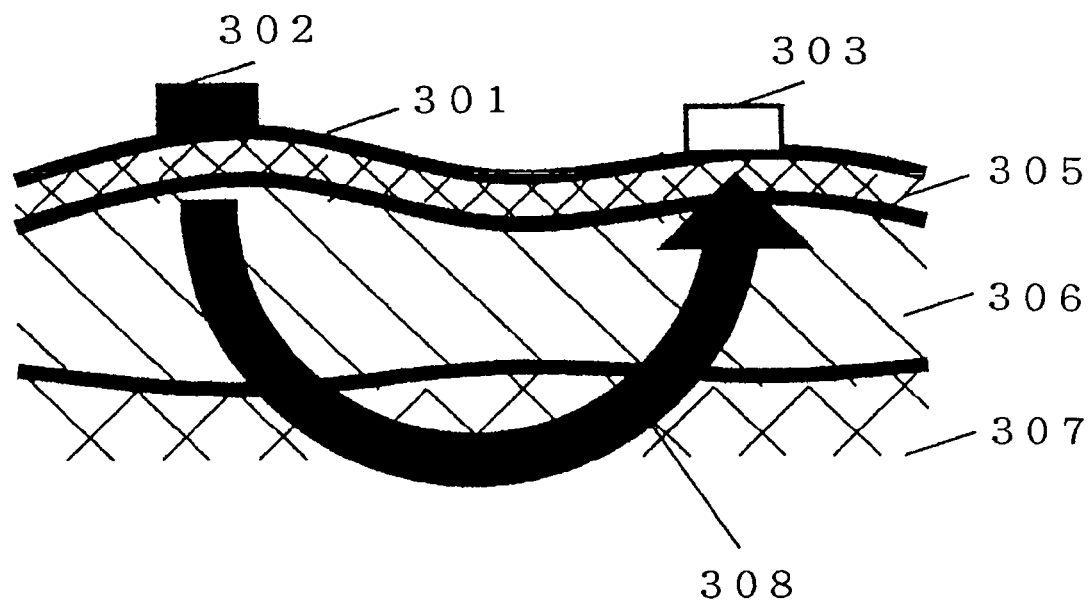
FIG. 39 is a conceptual view showing a problem in the conventional subcutaneous fat thickness measuring apparatus.
Figure 40:
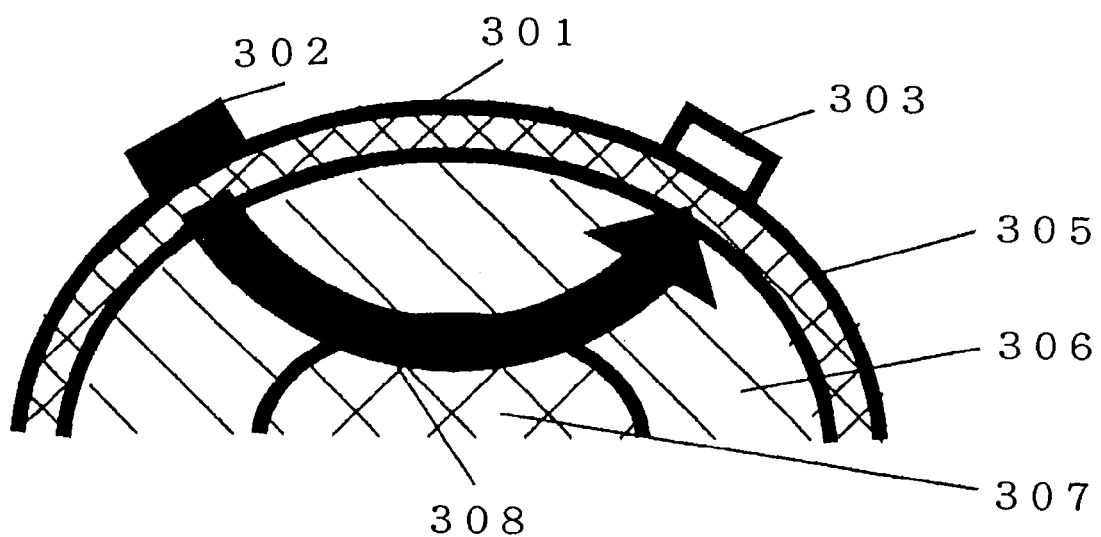
FIG. 40 is a conceptual view showing another problem in the conventional subcutaneous fat thickness measuring apparatus.

The relation between a parameter of Y2/Y1 with the amount of received light for measurement (amount of received light in the second distance Y2) divided by the amount of received light for correction (amount of received light in the first distance Y1) and the thickness of the subcutaneous fat 206 is shown in FIG. 37.

Compared with FIG. 35, variations are apparently alleviated, and it can thus be understood that the amount of received light for correction brings about an effect of correlation. Thus, as in the case of using only the amount of received light for measurement, the primary regression line showing the correlation between Y2/Y1 and the thickness of subcutaneous fat is determined in advance, and the primary regression line and the Y2/Y1 are used, whereby influences of the skin 205 can further be corrected, thus making it possible to measure the thickness of subcutaneous fat with higher reproducibility and accuracy.

EMBODIMENT 11

The block diagram of the apparatus of measuring the thickness of subcutaneous fat using light in Embodiment 11 of the present invention is similar to those of FIGS. 30 and 31. It differs from the apparatus of measuring the thickness of subcutaneous fat using light of Embodiment 10 in that after variations in the amount of received light for measurement and the amount of received light for correction are stably within predefined values in the calculation part after the pressure is detected in the pressure detecting part, the thickness of subcutaneous fat is calculated from the amount of received light for measurement and the amount of received light for correction. Other aspects of configuration are same as those of the apparatus of measuring the thickness of subcutaneous fat using light in Embodiment 10, and therefore the description thereof is not presented here.

The procedure of measurement will now be described. As a first operation, the forming part 210 is contacted against the surface of the organism 201 while the light source 211 is unlit.

As a second operation, if the amount of light received in the light receiving part 212 is about 100 pW or smaller, and a pressure equal to or greater than about 7 kPa is detected in the pressure detecting part 224, the light source element 217 is lit up when it is ensured that the entire light receiving part 212 contacts the surface of the organism and the forming part 210 is contacted against the surface of the organism with a sufficient pressure, and in this state, a signal for start of measurement is inputted from the communication part 222 or input part 223.

As a third operation, the received amount of light 218 propagating from the correcting light source element 217 through the inside of the organism and arriving at the light receiving part 212, namely the amount of received light for correction (amount of received light in the first distance Y1) is measured.

Furthermore, the first, second and third operations are carried out in this order in the procedure described above, but instead thereof, the first, second and third operations may be carried out in any order. Also, the light source 211 is not lit when the first operation is carried out in the procedure described above, but the light source 211 may be lit up before the first operation is carried out.

The calculation part 220 monitors the amount of received light for correction, and determines the average of the amount of received light for correction when the variation in the amount of received light for correction per second reaches to a level within about ±10%.

Then, as a fourth operation, the received amount of light 219 propagating from the measuring light source element 216 through the inside of the organism and arriving at the light receiving part 212, namely the amount of received light for measurement (amount of received light in the second distance Y2) while the correcting light source element 217 is unlit and the measuring light source element 216 is lit. The calculation part 220 monitors the amount of received light for measurement, and determines the average of the amount of received light for measurement when the variation in the amount of received light for measurement per second reaches to a level within about ±10%. Here, the reason why the average of the amount of received light per second is determined is that the amount of received light is also influenced by the pulsating flow of blood flowing through the inside of the organism, and the average over one second or longer is calculated in consideration of the fact that the pulse rate of human being is at one or more per second, whereby data with no influences of the pulse flow can be obtained.

How the thickness of the subcutaneous fat 206 is calculated in the calculation part 220 will now be described. The relation between the amount of received light for measurement and the thickness of the subcutaneous fat is shown in FIG. 35. In FIG. 35, the white circle shows the relation between the amount of received light for measurement and the measured thickness of the subcutaneous fat 206, and the solid line is its primary regression line. Thus, by using a relational expression of this primary regression line and the average of the measured amount of received light for measurement, the thickness of subcutaneous fat can be determined. According to this measurement method, measurements are carried out while the thickness of the subcutaneous fat 206 is kept stable, thus making it possible to measure the thickness of subcutaneous fat with high reproducibility and accuracy.

In addition, the correction of influences of colors of the skin 205 and the like will be described. The relation between a parameter of Y2/Y1 with the average of the amount of received light for measurement (amount of received light in the second distance Y2) divided by the average of the amount of received light for correction (amount of received light in the first distance Y1) and the thickness of the subcutaneous fat 206 is shown in FIG. 37. In FIG. 37, the white circle shows the relation between the Y2/Y1 and the thickness of the subcutaneous fat 206, and the solid line is its primary regression line. Thus, by using a relational expression of this primary regression line and the calculated parameter Y2/Y1, the thickness of subcutaneous fat can be determined. According to this measurement method, influences of colors of the skin 205 and the like can be corrected, thus making it possible to measure the thickness of subcutaneous fat with higher reproducibility and accuracy.

As apparent from the above, according to the present invention, it is possible to provide a compact method of measuring biological information using light and apparatus of measuring biological information using light that can measure biological information such as the thickness of subcutaneous fat, the percent of body fat, the concentration of glucose in an organism and the concentration of oxygen in an organism can be measured with high reproducibility and accuracy.

As apparent from the above, according to the present invention, there is provided a method of measuring the thickness of subcutaneous fat using light and an apparatus of measuring the thickness of subcutaneous fat using light capable of measuring biological information such as the thickness of subcutaneous fat, the percent of body fat, the concentration of glucose in an organism and the concentration of oxygen in an organism with high reproducibility and accuracy.

The invention claimed is:

1. A method of measuring biological information utilizing an apparatus of measuring said biological information using light comprising: a light source part adapted to irradiate an organism; a light receiving part receiving light propagating from said light source part through an inside of said organism and outgoing from a surface of said organism; a forming part adapted to form said surface of said organism into a predetermined shape by applying a pressure thereto; a protrusion part being provided on a face of said forming part contacting said surface of said organism; a pressure detecting part detecting said pressure applied to said surface of said organism by said forming part, said pressure detecting part is connected to said forming part; and a calculation part calculating said biological information of said organism using information of a relation between an amount of said received light and said biological information of said organism previously determined, based on said amount of said light received in said light receiving part, at least one of said light source part and said light receiving part is provided on said protrusion part, said calculation part calculates said biological information of said organism based on said amount of said received light when it is detected that said pressure reaches said level equal to or greater than said predefined value, said method comprising:
  a first step of utilizing said forming part to form said surface of said organism into said predetermined shape by applying said pressure thereto;
  a second step of utilizing said light source part to irradiate said organism with said light;
  a third step of utilizing said light receiving part to receive said light propagating through said inside of said organism and outgoing from said surface of said organism; and
  a fourth step of utilizing said calculation part to calculate said biological information of said organism using said information of said relation between said amount of said received light and said biological information of said organism previously determined, based on said amount of said light received in said third step,
  wherein in said fourth step, said biological information of said organism is calculated using said information of said relation between said amount of said received light, which has been acquired after said pressure reaches a level equal to or greater than a predefined value, and said biological information of said organism previously determined, based on said amount of said received light acquired after said pressure reaches said level equal to or greater than said predefined value.

2. The method of measuring biological information according to claim 1, wherein said predefined value of said pressure is about 7 kPa or greater.

3. A method of measuring biological information utilizing an apparatus of measuring said biological information using light comprising: a light source part adapted to irradiate an organism; a light receiving part receiving light propagating from said light source part through an inside of said organism and outgoing from a surface of said organism; a forming part adapted to form said surface of said organism into a predetermined shape by applying a pressure thereto; a protrusion part being provided on a face of said forming part contacting said surface of said organism; a pressure measuring part measuring said pressure applied to said surface of said organism by said forming part, said pressure measuring part is connected to said forming part; and a calculation part calculating said biological information of said organism using information of a relation at least between an amount of said received light and said biological information of said organism previously determined, based on said amount of said light received in said receiving part and said pressure measured in said pressure measuring part, at least one of said light source part and said light receiving part is provided on said protrusion part, said method comprising:
  a first step of utilizing said forming part to form said surface of said organism into said predetermined shape by applying said pressure thereto;
  a second step of utilizing said light source part to irradiate said organism with said light;
  a third step of utilizing said light receiving part to receive said light propagating through said inside of said organism and outgoing from said surface of said organism;
  a fourth step of utilizing said calculation part to calculate said biological information of said organism using said information of said relation at least between said amount of said received light and said biological information of said organism previously determined, based on said amount of said light received in said third step; and
  a fifth step of utilizing said pressure measuring part to measure said pressure,
  wherein in said fourth step, said biological information of said organism is calculated using said information of said relation between said amount of said received light, said pressure and said biological information of said organism previously determined, based on said amount of said light received in said third step and said pressure measured in said fifth step.

4. The method of measuring biological information according to claim 1 or 3, wherein a central wavelength of said light applied in said second step is a wavelength of about 500 nm to 1000 nm.

5. The method of measuring biological information according to claim 1 or 3, wherein in said fourth step, said biological information of said organism is calculated at a time when a predetermined amount of time passes after said pressure reaches a predefined value.

6. The method of measuring biological information according to claim 5, comprising a further step of detecting that said pressure reaches said predefined value, wherein in said fourth step, said biological information of said organism is calculated based on said amount of said light received in said third step at a time when a predetermined amount of time passes after it is detected that said pressure reaches said predefined value.

7. The method of measuring biological information according to claim 6, wherein said predetermined amount of time is about 200 ms or greater.

8. The method of measuring biological information according to claim 1 or 3, wherein in said fourth step, said biological information of said organism is calculated after said amount of said received light is stabilized.

9. The method of measuring biological information according to claim 8, comprising a further step of detecting that said pressure reaches said predefined value, wherein in said fourth step, variations in said amount of said light received in said third step are monitored when it is detected that said pressure reaches said predefined value, and said biological information of said organism is calculated based on said amount of said received light acquired when said variations in said amount of received light are within a predetermined value.

10. The method of measuring biological information according to claim 9, wherein said variations in said amount of received light being within about ±10%.

11. An apparatus of measuring biological information using light comprising:
a light source part adapted to irradiate an organism;
a light receiving part receiving light propagating from said light source part through an inside of said organism and outgoing from a surface of said organism;
a forming part adapted to form said surface of said organism into a predetermined shape by applying a pressure thereto;
a protrusion part being provided on a face of said forming part contacting said surface of said organism;
a pressure detecting part detecting said pressure applied to said surface of said organism by said forming part, said pressure detecting part is connected to said forming part; and
a calculation part calculating said biological information of said organism using information of a relation between an amount of said received light and previously determined biological information of said organism, based on said amount of said light received in said light receiving part,
wherein at least one of said light source part and said light receiving part is provided on said protrusion part, and
said calculation part calculates said biological information of said organism based on said amount of said received light when it is detected that said pressure reaches a level equal to or greater than a predefined value.

12. An apparatus of measuring biological information using light comprising;
a light source part adapted to irradiate an organism;
a light receiving part receiving light propagating from said light source part through an inside of said organism and outgoing from a surface of said organism;
a forming part adapted to form said surface of said organism into a predetermined shape by applying a pressure thereto;
a protrusion part being provided on a face of said forming part contacting said surface of said organism;
a pressure measuring part measuring said pressure applied to said surface of said organism by said forming part, said pressure measuring part is connected to said forming part; and
a calculation part calculating said biological information of said organism using information of a relation between an amount of said received light, said pressure and previously determined biological information of said organism, based on said amount of said light received in said receiving part and said pressure measured in said pressure measuring part,
wherein at least one of said light source part and said light receiving part is provided on said protrusion part.

13. The apparatus of measuring biological information using light according to claim 11 or 12, wherein said face of said forming part contacting said surface of said organism is substantially flat.

14. The apparatus of measuring biological information using light according to claim 11 or 12, wherein
said light source part and said light receiving part are provided on said protrusion part.

15. The apparatus of measuring biological information using light according to claim 11 or 12, wherein said light source part has a plurality of light sources.

16. The apparatus of measuring biological information using light according to claim 15, wherein said light source part has said light sources provided so that a distance between a first of said light sources and said light receiving part is a first distance of about 15 mm to 30 mm and a distance between a second of said light sources and said light receiving part is a second distance of about 35 mm to 80 mm, and
if said amount of light received in said light receiving part from said light source with said first distance equals Y1, and said amount of light received in said light receiving part from said light source with said second distance equals Y2, said calculation part calculates said biological information of said organism using a ratio between said Y2 and said Y1.

17. The apparatus of measuring biological information using light according to claim 11 or 12, wherein said light receiving part has a plurality of light receiving elements.

18. The apparatus of measuring biological information using light according to claim 17, wherein said light receiving part has said light receiving elements provided so that a distance between said light source part and a first of said light receiving elements is a first distance of about 15 mm to 30 mm and a distance between said light source part and a second of said light receiving elements is a second distance of about 35 mm to 80 mm, and
if said amount of light received in said light receiving element with said first distance equals Y1, and said amount of light received in said light receiving element with said second distance equals Y2, said calculation part calculates said biological information of said organism using a ratio between said Y2 and said Y1.

19. The apparatus of measuring biological information using light according to claim 11 or 12, comprising:
a display part displaying said biological information of said organism calculated in said calculation part;
a communication part communicating said biological information of said organism to and from external apparatuses; and
an input part for inputting measurement conditions of said organism.

* * * * *